US011672816B2

(12) United States Patent
Hernández Ribera et al.

(10) Patent No.: US 11,672,816 B2
(45) Date of Patent: Jun. 13, 2023

(54) ANTISENSE OLIGONUCLEOTIDES AND USES THEREOF

(71) Applicants: FUNDACIÓ CENTRE DE REGULACIÓ GENÒMICA, Barcelona (ES); INSTITUCIÓ CATALANA DE RECERCA I ESTUDIS AVANÇATS, Barcelona (ES); FUNDACIÓN DEL SECTOR PÚBLICO ESTATAL CENTRO NACIONAL DE INVESTIGACIONES ONCOLÓGICAS CARLOS III (F.S.P. CNIO), Madrid (ES)

(72) Inventors: Jordi Hernández Ribera, Barcelona (ES); Juan Alberto Valcárcel Juárez, Barcelona (ES); Elias Bechara, Barcelona (ES); Manuel Serrano Marugán, Tres Cantos (ES); Miguel Rovira Del Olmo, Madrid (ES); Pablo José Fernández Marcos, Las Rozas (ES)

(73) Assignees: INSTITUCIÓ CATALANA DE RECERCA I ESTUDIS AVANÇATS, Barcelona (ES); FUNDACIÓ CENTRE DE REGULACIÓ GENÒMICA, Barcelona (ES); FUNDACIÓN DEL SECTOR PÚBLICO ESTATAL CENTRO NACION, Barcelona (ES)

( * ) Notice: Subject to any disclaimer, the term of this patent is extended or adjusted under 35 U.S.C. 154(b) by 0 days.

(21) Appl. No.: 16/982,167

(22) PCT Filed: Mar. 19, 2019

(86) PCT No.: PCT/EP2019/056889

§ 371 (c)(1),
(2) Date: Sep. 18, 2020

(87) PCT Pub. No.: WO2019/180046

PCT Pub. Date: Sep. 26, 2019

(65) Prior Publication Data

US 2022/0079969 A1 Mar. 17, 2022

(30) Foreign Application Priority Data

Mar. 19, 2018 (EP) .................................... 18162571

(51) Int. Cl.

| | |
|---|---|
| ***C07H 21/04*** | (2006.01) |
| ***A61K 31/712*** | (2006.01) |
| ***A61P 35/00*** | (2006.01) |
| ***A61K 9/00*** | (2006.01) |
| ***A61K 31/7125*** | (2006.01) |
| ***C12N 15/113*** | (2010.01) |

(52) U.S. Cl.
CPC .......... *A61K 31/712* (2013.01); *A61K 9/0019* (2013.01); *A61K 31/7125* (2013.01); *A61P 35/00* (2018.01); *C12N 15/113* (2013.01)

(58) Field of Classification Search
None
See application file for complete search history.

(56) References Cited

U.S. PATENT DOCUMENTS

2014/0154783 A1 6/2014 Rossomando et al.

FOREIGN PATENT DOCUMENTS

| | | | |
|---|---|---|---|
| EP | 2311530 | A2 | 4/2011 |
| EP | 3029149 | A1 | 6/2016 |
| WO | 2002085308 | A2 | 10/2002 |
| WO | 2010011642 | A2 | 1/2010 |
| WO | 2013086639 | A1 | 6/2013 |

OTHER PUBLICATIONS

Cieply, Benjamin, and Russ P. Carstens. "Functional roles of alternative splicing factors in human disease." Wiley Interdisciplinary Reviews: RNA 6.3 (2015): 311-326.*

Elias G. Bechara et al, RBM5, 6, and 10 Differentially Regulate NUMB Alternative Splicing to Control Cancer Cell Proliferation; Molecular Cell, vol. 52, No. 5, Dec. 12, 2013; pp. 720-733.

Benjamin Cieply et al, Functional roles of alternative splicing factors in human disease; Wiley Interdisciplinary Reviews: RNA, vol. 6, No. 3, Jan. 28, 2015, pp. 311-326.

Jordi Hernandez et al, Tumor suppressor properties of the splicing regulatory factor RBM10; RNA Biology, vol. 13, No. 4, Feb. 6, 2016, pp. 466-472.

Jing Lin et al, Induced-Decay of Glycine Decarboxylase Transcripts as an Anticancer Therapeutic Strategy for Non-Small-Cell Lung Carcinoma; Molecular Therapy—Nucleic Acids, vol. 9, Oct. 7, 2017, pp. 263-273.

C.M. Misquitta-Ali et al, Global Profiling and Molecular Characterization of Alternative Splicing Events Misregulated in Lung Cancer; Molecular and Cellular Biology, vol. 31, No. 1, Nov. 1, 2010; pp. 138-150.

D. Rajendran et al, Regulation of NUMB Isoform expression by activated ERK signaling; Oncogene, vol. 35, No. 39, Apr. 4, 2016; pp. 5202-5213.

(Continued)

*Primary Examiner* — Kimberly Chong
(74) *Attorney, Agent, or Firm* — Dinsmore & Shohl LLP

(57) ABSTRACT

Disclosed herein are novel compounds comprising antisense oligonucleotides that regulate the splicing of NUMB. In particular, an antisense oligonucleotide for reducing inclusion of NUMB exon 9 in a population of mature NUMB transcripts is provided. The antisense oligonucleotide comprises a sequence of at least 7 nucleotides that is complementary to a target region within exon 9 of a NUMB transcript. Pharmaceutical compositions comprising the antisense oligonucleotide and methods of treating a proliferative disease using the compounds or compositions of the invention are also described.

18 Claims, 20 Drawing Sheets

Specification includes a Sequence Listing.

(56) References Cited

OTHER PUBLICATIONS

Kavitha Siva et al, Exon-Skipping Antisense Oligonucleotides to Correct Missplicing in Neurogenetic Diseases; Nucleic Acid Therapeutics, vol. 24, No. 1, Feb. 7, 2014, pp. 69-86.

Jiawei Zhao et al, Functional analysis reveals that RBM10 mutations contribute to lung adenocarcinoma pathogenesis by deregulating splicing; Scientific Reports, vol. 7, No. 1, Jan. 16, 2017.

European Examination Report dated Apr. 3, 2023 in reference to EP19717230.7.

* cited by examiner

| | H1395 | H1666 | pc3 | QGP1 | Capan2 |
|---|---|---|---|---|---|
| DPSI | -0.212 | -0.189 | -0.406 | NA | -0.833 |
| [nM] | 10 | 10 | 50 | 100 | 50 |

SEQUENCE LISTING

<160> NUMBER OF SEQ ID NOS: 372

<210> SEQ ID NO 1
<211> LENGTH: 147
<212> TYPE: DNA
<213> ORGANISM: Mus Musculus
<220> FEATURE:
<223> OTHER INFORMATION: NM_001136075.2 - Numb mRNA transcript variant
1 - 1115..1261

<400> SEQUENCE: 1
ctaatggcac tgactcagcc tcccatgtgc ttactgctaa gccagccaat actgctctag 60
cacacgtagc aatgcctgtc cgtgaaacca acccctgggc ccatgtccct gatgctgcta 120
acaaggaaat tgcagccata catccgg 147

<210> SEQ ID NO 2
<211> LENGTH: 144
<212> TYPE: DNA
<213> ORGANISM: Homo sapiens

```
<220> FEATURE:
<223> OTHER INFORMATION: NM_001005743 - Numb mRNA transcript variant
      1-1417..1560

<400> SEQUENCE: 2

ctaatggcac tgactcagcc ttccatgtgc ttgctaagcc agcccatact gctctagcac      60

ccgtagcaat gcctgtgcgt gaaaccaacc cttgggccca tgcccctgat gctgctaaca     120

aggaaattgc agccacatgt tcgg                                            144


<210> SEQ ID NO 3
<211> LENGTH: 21
<212> TYPE: RNA
<213> ORGANISM: Homo sapiens
<220> FEATURE:
<223> OTHER INFORMATION: Region 2 of Homo sapiens Numb exon 9 (targeted
      by AON2 - SEQ ID NO: 13)

<400> SEQUENCE: 3

ccuuccaugu gcuugcuaag c                                                21


<210> SEQ ID NO 4
<211> LENGTH: 21
<212> TYPE: RNA
<213> ORGANISM: Homo sapiens
<220> FEATURE:
<223> OTHER INFORMATION: Region 3 of Homo sapiens Numb exon 9 (targeted
      by AON3 - SEQ ID NO: 14)

<400> SEQUENCE: 4

cagcccauac ugcucuagca c                                                21


<210> SEQ ID NO 5
<211> LENGTH: 21
<212> TYPE: RNA
<213> ORGANISM: Homo sapiens
<220> FEATURE:
<223> OTHER INFORMATION: Region 4 of Homo sapiens Numb exon 9 (targeted
      by AON4 - SEQ ID NO: 15)

<400> SEQUENCE: 5

ccguagcaau gccugugcgu g                                                21


<210> SEQ ID NO 6
<211> LENGTH: 21
<212> TYPE: RNA
<213> ORGANISM: Homo sapiens
<220> FEATURE:
<223> OTHER INFORMATION: Region 5 of Homo sapiens Numb exon 9 (targeted
      by AON5 - SEQ ID NO: 16)

<400> SEQUENCE: 6

aaaccaaccc uugggcccau g                                                21


<210> SEQ ID NO 7
<211> LENGTH: 21
<212> TYPE: RNA
<213> ORGANISM: Homo sapiens
<220> FEATURE:
<223> OTHER INFORMATION: Region 6 of Homo sapiens Numb exon 9 (targeted
      by AON6 - SEQ ID NO: 17)

<400> SEQUENCE: 7

ccccugaugc ugcuaacaag g                                                21


<210> SEQ ID NO 8
```

<211> LENGTH: 21
<212> TYPE: RNA
<213> ORGANISM: Homo sapiens
<220> FEATURE:
<223> OTHER INFORMATION: Region 7 of Homo sapiens Numb exon 9 (targeted by AON7 - SEQ ID NO: 18)

<400> SEQUENCE: 8
aaauugcagc cacauguucg g 21

<210> SEQ ID NO 9
<211> LENGTH: 39
<212> TYPE: RNA
<213> ORGANISM: Homo sapiens
<220> FEATURE:
<223> OTHER INFORMATION: Region 1+2 of Homo sapiens Numb exon 9 (targeted by AON1 - SEQ ID NO: 12 ; AON2 - SEQ ID NO: 13; and AON1-2 - SEQ ID NO: 19)

<400> SEQUENCE: 9
cuaauggcac ugacucagcc uuccaugugc uugcuaagc 39

<210> SEQ ID NO 10
<211> LENGTH: 42
<212> TYPE: RNA
<213> ORGANISM: Homo sapiens
<220> FEATURE:
<223> OTHER INFORMATION: Region 4+5 of Homo sapiens Numb exon 9 (targeted by AON4 - SEQ ID NO: 15; AON5 - SEQ ID NO:16; and AON4-5 - SEQ ID NO: 22)

<400> SEQUENCE: 10
ccguagcaau gccugugcgu gaaaccaacc cuugggccca ug 42

<210> SEQ ID NO 11
<211> LENGTH: 42
<212> TYPE: RNA
<213> ORGANISM: Homo sapiens
<220> FEATURE:
<223> OTHER INFORMATION: Region 6+7 of Homo sapiens Numb exon 9 (targeted by AON6 - SEQ ID NO: 17; AON7 - SEQ ID NO: 18 and AON6-7 - SEQ ID NO: 24)

<400> SEQUENCE: 11
ccccugaugc ugcuaacaag gaaauugcag ccacauguuc gg 42

<210> SEQ ID NO 12
<211> LENGTH: 21
<212> TYPE: RNA
<213> ORGANISM: Artificial sequence
<220> FEATURE:
<223> OTHER INFORMATION: Antisense oligonucleotide targeting region 1 of Homo sapiens Numb exon 9 (AON1)

<400> SEQUENCE: 12
aggcugaguc agugccauua g 21

<210> SEQ ID NO 13
<211> LENGTH: 21
<212> TYPE: RNA
<213> ORGANISM: Artificial sequence
<220> FEATURE:
<223> OTHER INFORMATION: Antisense oligonucleotide targeting region 2 of Homo sapiens Numb exon 9 (AON2)

<400> SEQUENCE: 13
gcuuagcaag cacauggaag g 21

-continued

<210> SEQ ID NO 14
<211> LENGTH: 21
<212> TYPE: RNA
<213> ORGANISM: Artificial sequence
<220> FEATURE:
<223> OTHER INFORMATION: Antisense oligonucleotide targeting region 3 of Homo sapiens Numb exon 9 (AON3)

<400> SEQUENCE: 14
gugcuagagc aguaugggcu g 21

<210> SEQ ID NO 15
<211> LENGTH: 21
<212> TYPE: RNA
<213> ORGANISM: Artificial sequence
<220> FEATURE:
<223> OTHER INFORMATION: Antisense oligonucleotide targeting region 4 of Homo sapiens Numb exon 9 (AON4)

<400> SEQUENCE: 15
cacgcacagg cauugcuacg g 21

<210> SEQ ID NO 16
<211> LENGTH: 21
<212> TYPE: RNA
<213> ORGANISM: Artificial sequence
<220> FEATURE:
<223> OTHER INFORMATION: Antisense oligonucleotide targeting region 5 of Homo sapiens Numb exon 9 (AON5)

<400> SEQUENCE: 16
caugggccca aggguugguu u 21

<210> SEQ ID NO 17
<211> LENGTH: 21
<212> TYPE: RNA
<213> ORGANISM: Artificial sequence
<220> FEATURE:
<223> OTHER INFORMATION: Antisense oligonucleotide targeting region 6 of Homo sapiens Numb exon 9 (AON6)

<400> SEQUENCE: 17
ccuuguuagc agcaucaggg g 21

<210> SEQ ID NO 18
<211> LENGTH: 21
<212> TYPE: RNA
<213> ORGANISM: Artificial sequence
<220> FEATURE:
<223> OTHER INFORMATION: Antisense oligonucleotide targeting region 7 of Homo sapiens Numb exon 9 (AON7)

<400> SEQUENCE: 18
ccgaacaugu ggcugcaauu u 21

<210> SEQ ID NO 19
<211> LENGTH: 21
<212> TYPE: RNA
<213> ORGANISM: Artificial sequence
<220> FEATURE:
<223> OTHER INFORMATION: Antisense oligonucleotide targeting region 1-2 of Homo sapiens Numb exon 9 (AON1-2)

<400> SEQUENCE: 19
cacauggaag gcugagucag u 21

-continued

<210> SEQ ID NO 20
<211> LENGTH: 21
<212> TYPE: RNA
<213> ORGANISM: Artificial sequence
<220> FEATURE:
<223> OTHER INFORMATION: Antisense oligonucleotide targeting region 2-3 of Homo sapiens Numb exon 9 (AON2-3)

<400> SEQUENCE: 20
aguaugggcu ggcuuagcaa g 21

<210> SEQ ID NO 21
<211> LENGTH: 21
<212> TYPE: RNA
<213> ORGANISM: Artificial sequence
<220> FEATURE:
<223> OTHER INFORMATION: Antisense oligonucleotide targeting region 3-4 of Homo sapiens Numb exon 9 (AON3-4)

<400> SEQUENCE: 21
cauugcuacg ggugcuagag c 21

<210> SEQ ID NO 22
<211> LENGTH: 21
<212> TYPE: RNA
<213> ORGANISM: Artificial sequence
<220> FEATURE:
<223> OTHER INFORMATION: Antisense oligonucleotide targeting region 4-5 of Homo sapiens Numb exon 9 (AON4-5)

<400> SEQUENCE: 22
aggguugguu ucacgcacag g 21

<210> SEQ ID NO 23
<211> LENGTH: 21
<212> TYPE: RNA
<213> ORGANISM: Artificial sequence
<220> FEATURE:
<223> OTHER INFORMATION: Antisense oligonucleotide targeting region 5-6 of Homo sapiens Numb exon 9 (AON5-6)

<400> SEQUENCE: 23
agcaucaggg gcaugggccc a 21

<210> SEQ ID NO 24
<211> LENGTH: 21
<212> TYPE: RNA
<213> ORGANISM: Artificial sequence
<220> FEATURE:
<223> OTHER INFORMATION: Antisense oligonucleotide targeting region 6-7 of Homo sapiens Numb exon 9 (AON6-7)

<400> SEQUENCE: 24
ggcugcaauu uccuuguuag c 21

<210> SEQ ID NO 25
<211> LENGTH: 21
<212> TYPE: RNA
<213> ORGANISM: Artificial sequence
<220> FEATURE:
<223> OTHER INFORMATION: Antisense oligonucleotide targeting the 5' splice site of Numb exon 9

<400> SEQUENCE: 25
aucuguggcc accuuacccg a 21

<210> SEQ ID NO 26

<211> LENGTH: 21
<212> TYPE: RNA
<213> ORGANISM: Artificial sequence
<220> FEATURE:
<223> OTHER INFORMATION: Antisense oligonucleotide targeting the 3' splice site of Homo sapiens Numb exon 9

<400> SEQUENCE: 26
uuagcuacaa cgggagcaga c 21

<210> SEQ ID NO 27
<211> LENGTH: 21
<212> TYPE: RNA
<213> ORGANISM: Homo sapiens
<220> FEATURE:
<223> OTHER INFORMATION: Homo sapiens Numb exon 9 sequence targeted by antisense oligonucleotide of SEQ. ID NO: 25

<400> SEQUENCE: 27
ucggguaagg uggccacagau 21

<210> SEQ ID NO 28
<211> LENGTH: 21
<212> TYPE: RNA
<213> ORGANISM: Homo sapiens
<220> FEATURE:
<223> OTHER INFORMATION: Homo sapiens Numb exon 9 sequence targeted by antisense oligonucleotide of SEQ. ID NO: 26

<400> SEQUENCE: 28
gtctgctccc gttgtagcta a 21

<210> SEQ ID NO 29
<211> LENGTH: 23
<212> TYPE: RNA
<213> ORGANISM: Artificial sequence
<220> FEATURE:
<223> OTHER INFORMATION: Antisense oligonucleotide targeting the branching point of Homo sapiens Numb exon 9

<400> SEQUENCE: 29
caacaucaau ggaguuaauu cau 23

<210> SEQ ID NO 30
<211> LENGTH: 21
<212> TYPE: RNA
<213> ORGANISM: Homo sapiens
<220> FEATURE:
<223> OTHER INFORMATION: Region of Homo sapiens Numb exon 9 targeted by SEQ.ID NO: 19 (AON1-2)

<400> SEQUENCE: 30
acugacucag ccuuccaugu g 21

<210> SEQ ID NO 31
<211> LENGTH: 21
<212> TYPE: RNA
<213> ORGANISM: Homo sapiens
<220> FEATURE:
<223> OTHER INFORMATION: Region of Homo sapiens Numb exon 9 targeted by SEQ.ID NO: 22 (AON4-5)

<400> SEQUENCE: 31
ccugugcgug aaaccaaccc u 21

<210> SEQ ID NO 32
<211> LENGTH: 21

```
<212> TYPE: RNA
<213> ORGANISM: Homo sapiens
<220> FEATURE:
<223> OTHER INFORMATION: Region of Homo sapiens Numb exon 9 targeted by
      SEQ.ID NO: 24 (AON6-7)

<400> SEQUENCE: 32

gcuaacaagg aaauugcagc c                                              21


<210> SEQ ID NO 33
<211> LENGTH: 21
<212> TYPE: RNA
<213> ORGANISM: Homo sapiens
<220> FEATURE:
<223> OTHER INFORMATION: Region of Homo sapiens Numb exon 9 targeted by
      SEQ.ID NO: 20 (AON2-3)

<400> SEQUENCE: 33

cuugcuaagc cagcccauac u                                              21


<210> SEQ ID NO 34
<211> LENGTH: 21
<212> TYPE: RNA
<213> ORGANISM: Homo sapiens
<220> FEATURE:
<223> OTHER INFORMATION: Region of Homo sapiens Numb exon 9 targeted by
      SEQ.ID NO: 21 (AON3-4)

<400> SEQUENCE: 34

gcucuagcac ccguagcaau g                                              21


<210> SEQ ID NO 35
<211> LENGTH: 21
<212> TYPE: RNA
<213> ORGANISM: Homo sapiens
<220> FEATURE:
<223> OTHER INFORMATION: Region of Homo sapiens Numb exon 9 targeted by
      SEQ.ID NO: 23 (AON5-6)

<400> SEQUENCE: 35

ugggcccaug ccccugaugc u                                              21


<210> SEQ ID NO 36
<211> LENGTH: 7
<212> TYPE: RNA
<213> ORGANISM: Artificial sequence
<220> FEATURE:
<223> OTHER INFORMATION: Antisense oligonucleotide targeting region 1 of
      Homo sapiens Numb exon 9

<400> SEQUENCE: 36

aggcuga                                                               7


<210> SEQ ID NO 37
<211> LENGTH: 7
<212> TYPE: RNA
<213> ORGANISM: Artificial sequence
<220> FEATURE:
<223> OTHER INFORMATION: 37: Antisense oligonucleotide targeting region
      1 of Homo sapiens Numb exon 9

<400> SEQUENCE: 37

gucagug                                                               7


<210> SEQ ID NO 38
<211> LENGTH: 7
<212> TYPE: RNA
```

<213> ORGANISM: Artificial sequence
<220> FEATURE:
<223> OTHER INFORMATION: 38: Antisense oligonucleotide targeting region 1 of Homo sapiens Numb exon 9

<400> SEQUENCE: 38 ccauuag 7

<210> SEQ ID NO 39
<211> LENGTH: 7
<212> TYPE: RNA
<213> ORGANISM: Artificial sequence
<220> FEATURE:
<223> OTHER INFORMATION: 39: Antisense oligonucleotide targeting region 1-2 of Homo sapiens Numb exon 9

<400> SEQUENCE: 39 cugaguc 7

<210> SEQ ID NO 40
<211> LENGTH: 7
<212> TYPE: RNA
<213> ORGANISM: Artificial sequence
<220> FEATURE:
<223> OTHER INFORMATION: 40: Antisense oligonucleotide targeting region 2-3 of Homo sapiens Numb exon 9

<400> SEQUENCE: 40 agugcca 7

<210> SEQ ID NO 41
<211> LENGTH: 14
<212> TYPE: RNA
<213> ORGANISM: Artificial sequence
<220> FEATURE:
<223> OTHER INFORMATION: 41: Antisense oligonucleotide targeting region 1 of Homo sapiens Numb exon 9

<400> SEQUENCE: 41
aggcugaguc agug 14

<210> SEQ ID NO 42
<211> LENGTH: 14
<212> TYPE: RNA
<213> ORGANISM: Artificial sequence
<220> FEATURE:
<223> OTHER INFORMATION: 42: Antisense oligonucleotide targeting region 1 of Homo sapiens Numb exon 9

<400> SEQUENCE: 42
gucagugcca uuag 14

<210> SEQ ID NO 43
<211> LENGTH: 21
<212> TYPE: RNA
<213> ORGANISM: Artificial sequence
<220> FEATURE:
<223> OTHER INFORMATION: 43: Antisense oligonucleotide targeting region 1 of Homo sapiens Numb exon 9
<220> FEATURE:
<221> NAME/KEY: cm
<222> LOCATION: 4
<220> FEATURE:
<221> NAME/KEY: cm
<222> LOCATION: 10
<220> FEATURE:
<221> NAME/KEY: cm
<222> LOCATION: 15
<220> FEATURE:

<221> NAME/KEY: cm
<222> LOCATION: 16

<400> SEQUENCE: 43
aggcugaguc agugccauua g 21

<210> SEQ ID NO 44
<211> LENGTH: 21
<212> TYPE: RNA
<213> ORGANISM: Homo sapiens
<220> FEATURE:
<223> OTHER INFORMATION: 44: Region 1 of Homo sapiens Numb exon 9
(targeted by AON1 - SEQ ID NO:12)

<400> SEQUENCE: 44
cuaauggcac ugacucagcc u 21

<210> SEQ ID NO 45
<211> LENGTH: 7
<212> TYPE: RNA
<213> ORGANISM: Homo sapiens
<220> FEATURE:
<223> OTHER INFORMATION: 45: Target regions in region 1+2 of Homo
sapiens Numb exon 9

<400> SEQUENCE: 45 cuaaugg 7

<210> SEQ ID NO 46
<211> LENGTH: 7
<212> TYPE: RNA
<213> ORGANISM: Homo sapiens
<220> FEATURE:
<223> OTHER INFORMATION: 46: Target regions in region 1+2 of Homo
sapiens Numb exon 9

<400> SEQUENCE: 46 uaauggc 7

<210> SEQ ID NO 47
<211> LENGTH: 7
<212> TYPE: RNA
<213> ORGANISM: Homo sapiens
<220> FEATURE:
<223> OTHER INFORMATION: 47: target regions in region 1+2 of homo
sapiens numb exon 9

<400> SEQUENCE: 47 aauggca 7

<210> SEQ ID NO 48
<211> LENGTH: 7
<212> TYPE: RNA
<213> ORGANISM: Homo sapiens
<220> FEATURE:
<223> OTHER INFORMATION: 48: target regions in region 1+2 of homo
sapiens numb exon 9

<400> SEQUENCE: 48 auggcac 7

<210> SEQ ID NO 49
<211> LENGTH: 7
<212> TYPE: RNA
<213> ORGANISM: Homo sapiens
<220> FEATURE:
<223> OTHER INFORMATION: 49: target regions in region 1+2 of homo sapiens numb exon 9

<400> SEQUENCE: 49 uggcacu 7

<210> SEQ ID NO 50
<211> LENGTH: 7
<212> TYPE: RNA
<213> ORGANISM: Homo sapiens
<220> FEATURE:
<223> OTHER INFORMATION: 50: target regions in region 1+2 of homo sapiens numb exon 9

<400> SEQUENCE: 50 ggcacug 7

<210> SEQ ID NO 51
<211> LENGTH: 7
<212> TYPE: RNA
<213> ORGANISM: Homo sapiens
<220> FEATURE:
<223> OTHER INFORMATION: 51: target regions in region 1+2 of homo sapiens numb exon 9

<400> SEQUENCE: 51 gcacuga 7

<210> SEQ ID NO 52
<211> LENGTH: 7
<212> TYPE: RNA
<213> ORGANISM: Homo sapiens
<220> FEATURE:
<223> OTHER INFORMATION: 52: target regions in region 1+2 of homo s apiens numb exon 9

<400> SEQUENCE: 52 cacugac 7

<210> SEQ ID NO 53
<211> LENGTH: 7
<212> TYPE: RNA
<213> ORGANISM: Homo sapiens
<220> FEATURE:
<223> OTHER INFORMATION: 53: target regions in region 1+2 of homo sapiens numb exon 9

<400> SEQUENCE: 53 acugacu 7

<210> SEQ ID NO 54
<211> LENGTH: 7
<212> TYPE: RNA
<213> ORGANISM: Homo sapiens
<220> FEATURE:
<223> OTHER INFORMATION: 54: target regions in region 1+2 of homo sapiens numb exon 9

<400> SEQUENCE: 54 cugacuc 7

<210> SEQ ID NO 55
<211> LENGTH: 7
<212> TYPE: RNA
<213> ORGANISM: Homo sapiens
<220> FEATURE:
<223> OTHER INFORMATION: 55: target regions in region 1+2 of homo sapiens numb exon 9

<400> SEQUENCE: 55 ugacuca 7

<210> SEQ ID NO 56
<211> LENGTH: 7
<212> TYPE: RNA
<213> ORGANISM: Homo sapiens
<220> FEATURE:
<223> OTHER INFORMATION: 56: target regions in region 1+2 of homo
sapiens numb exon 9

<400> SEQUENCE: 56 gacucag 7

<210> SEQ ID NO 57
<211> LENGTH: 7
<212> TYPE: RNA
<213> ORGANISM: Homo sapiens
<220> FEATURE:
<223> OTHER INFORMATION: 57: target regions in region 1+2 of homo
sapiens numb exon 9

<400> SEQUENCE: 57 acucagc 7

<210> SEQ ID NO 58
<211> LENGTH: 7
<212> TYPE: RNA
<213> ORGANISM: Homo sapiens
<220> FEATURE:
<223> OTHER INFORMATION: 58: target regions in region 1+2 of homo
sapiens numb exon 9

<400> SEQUENCE: 58 cucagcc 7

<210> SEQ ID NO 59
<211> LENGTH: 7
<212> TYPE: RNA
<213> ORGANISM: Homo sapiens
<220> FEATURE:
<223> OTHER INFORMATION: 59: target regions in region 1+2 of homo
sapiens numb exon 9

<400> SEQUENCE: 59 ucagccu 7

<210> SEQ ID NO 60
<211> LENGTH: 7
<212> TYPE: RNA
<213> ORGANISM: Homo sapiens
<220> FEATURE:
<223> OTHER INFORMATION: 60: target regions in region 1+2 of homo
sapiens numb exon 9

<400> SEQUENCE: 60 cagccuu 7

<210> SEQ ID NO 61
<211> LENGTH: 7
<212> TYPE: RNA
<213> ORGANISM: Homo sapiens
<220> FEATURE:
<223> OTHER INFORMATION: 61: target regions in region 1+2 of homo
sapiens numb exon 9

<400> SEQUENCE: 61 agccuuc 7

<210> SEQ ID NO 62
<211> LENGTH: 7
<212> TYPE: RNA
<213> ORGANISM: Homo sapiens
<220> FEATURE:
<223> OTHER INFORMATION: 62: target regions in region 1+2 of homo sapiens numb exon 9

<400> SEQUENCE: 62 gccuucc 7

<210> SEQ ID NO 63
<211> LENGTH: 7
<212> TYPE: RNA
<213> ORGANISM: Homo sapiens
<220> FEATURE:
<223> OTHER INFORMATION: 63: target regions in region 1+2 of homo sapiens numb exon 9

<400> SEQUENCE: 63 ccuucca 7

<210> SEQ ID NO 64
<211> LENGTH: 7
<212> TYPE: RNA
<213> ORGANISM: Homo sapiens
<220> FEATURE:
<223> OTHER INFORMATION: 64: target regions in region 1+2 of homo sapiens numb exon 9

<400> SEQUENCE: 64 cuuccau 7

<210> SEQ ID NO 65
<211> LENGTH: 7
<212> TYPE: RNA
<213> ORGANISM: Homo sapiens
<220> FEATURE:
<223> OTHER INFORMATION: 65: target regions in region 1+2 of homo sapiens numb exon 9

<400> SEQUENCE: 65 uuccaug 7

<210> SEQ ID NO 66
<211> LENGTH: 7
<212> TYPE: RNA
<213> ORGANISM: Homo sapiens
<220> FEATURE:
<223> OTHER INFORMATION: 66: target regions in region 1+2 of homo sapiens numb exon 9

<400> SEQUENCE: 66 uccaugu 7

<210> SEQ ID NO 67
<211> LENGTH: 7
<212> TYPE: RNA
<213> ORGANISM: Homo sapiens
<220> FEATURE:
<223> OTHER INFORMATION: 67: target regions in region 1+2 of homo sapiens numb exon 9

<400> SEQUENCE: 67 ccaugug 7

<210> SEQ ID NO 68
<211> LENGTH: 7
<212> TYPE: RNA
<213> ORGANISM: Homo sapiens
<220> FEATURE:
<223> OTHER INFORMATION: 68: target regions in region 1+2 of homo
sapiens numb exon 9

<400> SEQUENCE: 68 caugugc 7

<210> SEQ ID NO 69
<211> LENGTH: 7
<212> TYPE: RNA
<213> ORGANISM: Homo sapiens
<220> FEATURE:
<223> OTHER INFORMATION: 69: target regions in region 1+2 of homo
sapiens numb exon 9

<400> SEQUENCE: 69 augugcu 7

<210> SEQ ID NO 70
<211> LENGTH: 7
<212> TYPE: RNA
<213> ORGANISM: Homo sapiens
<220> FEATURE:
<223> OTHER INFORMATION: 70: target regions in region 1+2 of homo
sapiens numb exon 9

<400> SEQUENCE: 70 ugugcuu 7

<210> SEQ ID NO 71
<211> LENGTH: 7
<212> TYPE: RNA
<213> ORGANISM: Homo sapiens
<220> FEATURE:
<223> OTHER INFORMATION: 71: target regions in region 1+2 of homo
sapiens numb exon 9

<400> SEQUENCE: 71 gugcuug 7

<210> SEQ ID NO 72
<211> LENGTH: 7
<212> TYPE: RNA
<213> ORGANISM: Homo sapiens
<220> FEATURE:
<223> OTHER INFORMATION: 72: target regions in region 1+2 of homo
sapiens numb exon 9

<400> SEQUENCE: 72 ugcuugc 7

<210> SEQ ID NO 73
<211> LENGTH: 7
<212> TYPE: RNA
<213> ORGANISM: Homo sapiens
<220> FEATURE:
<223> OTHER INFORMATION: 73: target regions in region 1+2 of homo
sapiens numb exon 9

<400> SEQUENCE: 73 gcuugcu 7

<210> SEQ ID NO 74
<211> LENGTH: 7
<212> TYPE: RNA
<213> ORGANISM: Homo sapiens
<220> FEATURE:
<223> OTHER INFORMATION: 74: target regions in region 1+2 of homo sapiens numb exon 9

<400> SEQUENCE: 74 cuugcua 7

<210> SEQ ID NO 75
<211> LENGTH: 7
<212> TYPE: RNA
<213> ORGANISM: Homo sapiens
<220> FEATURE:
<223> OTHER INFORMATION: 75: target regions in region 1+2 of homo sapiens numb exon 9

<400> SEQUENCE: 75 uugcuaa 7

<210> SEQ ID NO 76
<211> LENGTH: 7
<212> TYPE: RNA
<213> ORGANISM: Homo sapiens
<220> FEATURE:
<223> OTHER INFORMATION: 76: target regions in region 1+2 of homo sapiens numb exon 9

<400> SEQUENCE: 76 ugcuaag 7

<210> SEQ ID NO 77
<211> LENGTH: 7
<212> TYPE: RNA
<213> ORGANISM: Homo sapiens
<220> FEATURE:
<223> OTHER INFORMATION: 77: target regions in region 1+2 of homo sapiens numb exon 9

<400> SEQUENCE: 77 gcuaagc 7

<210> SEQ ID NO 78
<211> LENGTH: 13
<212> TYPE: RNA
<213> ORGANISM: Homo sapiens
<220> FEATURE:
<223> OTHER INFORMATION: 78: target regions in region 1+2 of homo sapiens numb exon 9

<400> SEQUENCE: 78
cuaauggcac uga 13

<210> SEQ ID NO 79
<211> LENGTH: 13
<212> TYPE: RNA
<213> ORGANISM: Homo sapiens
<220> FEATURE:
<223> OTHER INFORMATION: 79: target regions in region 1+2 of homo sapiens numb exon 9

<400> SEQUENCE: 79
uaauggcacu gac 13

<210> SEQ ID NO 80
<211> LENGTH: 13
<212> TYPE: RNA
<213> ORGANISM: Homo sapiens
<220> FEATURE:
<223> OTHER INFORMATION: 80: target regions in region 1+2 of homo sapiens numb exon 9

<400> SEQUENCE: 80
aauggcacug acu 13

<210> SEQ ID NO 81
<211> LENGTH: 13
<212> TYPE: RNA
<213> ORGANISM: Homo sapiens
<220> FEATURE:
<223> OTHER INFORMATION: 81: target regions in region 1+2 of homo sapiens numb exon 9

<400> SEQUENCE: 81
auggcacuga cuc 13

<210> SEQ ID NO 82
<211> LENGTH: 13
<212> TYPE: RNA
<213> ORGANISM: Homo sapiens
<220> FEATURE:
<223> OTHER INFORMATION: 82: target regions in region 1+2 of homo sapiens numb exon 9

<400> SEQUENCE: 82
uggcacugac uca 13

<210> SEQ ID NO 83
<211> LENGTH: 13
<212> TYPE: RNA
<213> ORGANISM: Homo sapiens
<220> FEATURE:
<223> OTHER INFORMATION: 83: target regions in region 1+2 of homo sapiens numb exon 9

<400> SEQUENCE: 83
ggcacugacu cag 13

<210> SEQ ID NO 84
<211> LENGTH: 13
<212> TYPE: RNA
<213> ORGANISM: Homo sapiens
<220> FEATURE:
<223> OTHER INFORMATION: 84: target regions in region 1+2 of homo sapiens numb exon 9

<400> SEQUENCE: 84
gcacugacuc agc 13

<210> SEQ ID NO 85
<211> LENGTH: 13
<212> TYPE: RNA
<213> ORGANISM: Homo sapiens
<220> FEATURE:
<223> OTHER INFORMATION: 85: target regions in region 1+2 of homo sapiens numb exon 9

<400> SEQUENCE: 85
cacugacuca gcc 13

```
<210> SEQ ID NO 86
<211> LENGTH: 13
<212> TYPE: RNA
<213> ORGANISM: Homo sapiens
<220> FEATURE:
<223> OTHER INFORMATION: 86: target regions in region 1+2 of homo
      sapiens numb exon 9

<400> SEQUENCE: 86

acugacucag ccu                                                        13


<210> SEQ ID NO 87
<211> LENGTH: 13
<212> TYPE: RNA
<213> ORGANISM: Homo sapiens
<220> FEATURE:
<223> OTHER INFORMATION: 87: target regions in region 1+2 of homo
      sapiens numb exon 9

<400> SEQUENCE: 87

cugacucagc cuu                                                        13


<210> SEQ ID NO 88
<211> LENGTH: 13
<212> TYPE: RNA
<213> ORGANISM: Homo sapiens
<220> FEATURE:
<223> OTHER INFORMATION: 88: target regions in region 1+2 of homo
      sapiens numb exon 9

<400> SEQUENCE: 88

ugacucagcc uuc                                                        13


<210> SEQ ID NO 89
<211> LENGTH: 13
<212> TYPE: RNA
<213> ORGANISM: Homo sapiens
<220> FEATURE:
<223> OTHER INFORMATION: 89: target regions in region 1+2 of homo
      sapiens numb exon 9

<400> SEQUENCE: 89

gacucagccu ucc                                                        13


<210> SEQ ID NO 90
<211> LENGTH: 13
<212> TYPE: RNA
<213> ORGANISM: Homo sapiens
<220> FEATURE:
<223> OTHER INFORMATION: 90: target regions in region 1+2 of homo
      sapiens numb exon 9

<400> SEQUENCE: 90

acucagccuu cca                                                        13


<210> SEQ ID NO 91
<211> LENGTH: 13
<212> TYPE: RNA
<213> ORGANISM: Homo sapiens
<220> FEATURE:
<223> OTHER INFORMATION: 91: target regions in region 1+2 of homo
      sapiens numb exon 9

<400> SEQUENCE: 91

cucagccuuc cau                                                        13
```

<210> SEQ ID NO 92
<211> LENGTH: 13
<212> TYPE: RNA
<213> ORGANISM: Homo sapiens
<220> FEATURE:
<223> OTHER INFORMATION: 92: target regions in region 1+2 of homo sapiens numb exon 9

<400> SEQUENCE: 92
ucagccuucc aug 13

<210> SEQ ID NO 93
<211> LENGTH: 13
<212> TYPE: RNA
<213> ORGANISM: Homo sapiens
<220> FEATURE:
<223> OTHER INFORMATION: 93: target regions in region 1+2 of homo sapiens numb exon 9

<400> SEQUENCE: 93
cagccuucca ugu 13

<210> SEQ ID NO 94
<211> LENGTH: 13
<212> TYPE: RNA
<213> ORGANISM: Homo sapiens
<220> FEATURE:
<223> OTHER INFORMATION: 94: target regions in region 1+2 of homo sapiens numb exon 9

<400> SEQUENCE: 94
agccuuccau gug 13

<210> SEQ ID NO 95
<211> LENGTH: 13
<212> TYPE: RNA
<213> ORGANISM: Homo sapiens
<220> FEATURE:
<223> OTHER INFORMATION: 95: target regions in region 1+2 of homo sapiens numb exon 9

<400> SEQUENCE: 95
gccuuccaug ugc 13

<210> SEQ ID NO 96
<211> LENGTH: 13
<212> TYPE: RNA
<213> ORGANISM: Homo sapiens
<220> FEATURE:
<223> OTHER INFORMATION: 96: target regions in region 1+2 of homo sapiens numb exon 9

<400> SEQUENCE: 96
ccuuccaugu gcu 13

<210> SEQ ID NO 97
<211> LENGTH: 13
<212> TYPE: RNA
<213> ORGANISM: Homo sapiens
<220> FEATURE:
<223> OTHER INFORMATION: 97: target regions in region 1+2 of homo sapiens numb exon 9

<400> SEQUENCE: 97
cuuccaugug cuu 13

<210> SEQ ID NO 98

<211> LENGTH: 13
<212> TYPE: RNA
<213> ORGANISM: Homo sapiens
<220> FEATURE:
<223> OTHER INFORMATION: 98: target regions in region 1+2 of homo sapiens numb exon 9

<400> SEQUENCE: 98
uuccaugugc uug 13

<210> SEQ ID NO 99
<211> LENGTH: 13
<212> TYPE: RNA
<213> ORGANISM: Homo sapiens
<220> FEATURE:
<223> OTHER INFORMATION: 99: target regions in region 1+2 of homo sapiens numb exon 9

<400> SEQUENCE: 99
uccaugugcu ugc 13

<210> SEQ ID NO 100
<211> LENGTH: 13
<212> TYPE: RNA
<213> ORGANISM: Homo sapiens
<220> FEATURE:
<223> OTHER INFORMATION: 100: target regions in region 1+2 of homo sapiens numb exon 9

<400> SEQUENCE: 100
ccaugugcuu gcu 13

<210> SEQ ID NO 101
<211> LENGTH: 13
<212> TYPE: RNA
<213> ORGANISM: Homo sapiens
<220> FEATURE:
<223> OTHER INFORMATION: 101: target regions in region 1+2 of homo sapiens numb exon 9

<400> SEQUENCE: 101
caugugcuug cua 13

<210> SEQ ID NO 102
<211> LENGTH: 13
<212> TYPE: RNA
<213> ORGANISM: Homo sapiens
<220> FEATURE:
<223> OTHER INFORMATION: 102: target regions in region 1+2 of homo sapiens numb exon 9

<400> SEQUENCE: 102
augugcuugc uaa 13

<210> SEQ ID NO 103
<211> LENGTH: 13
<212> TYPE: RNA
<213> ORGANISM: Homo sapiens
<220> FEATURE:
<223> OTHER INFORMATION: 103: target regions in region 1+2 of homo sapiens numb exon 9

<400> SEQUENCE: 103
ugugcuugcu aag 13

<210> SEQ ID NO 104
<211> LENGTH: 13

<212> TYPE: RNA
<213> ORGANISM: Homo sapiens
<220> FEATURE:
<223> OTHER INFORMATION: 104: target regions in region 1+2 of homo sapiens numb exon 9

<400> SEQUENCE: 104
gugcuugcua agc 13

<210> SEQ ID NO 105
<211> LENGTH: 21
<212> TYPE: RNA
<213> ORGANISM: Homo sapiens
<220> FEATURE:
<223> OTHER INFORMATION: 105: target regions in region 1+2 of homo sapiens numb exon 9

<400> SEQUENCE: 105
cuaauggcac ugacucagcc u 21

<210> SEQ ID NO 106
<211> LENGTH: 21
<212> TYPE: RNA
<213> ORGANISM: Homo sapiens
<220> FEATURE:
<223> OTHER INFORMATION: 106: target regions in region 1+2 of homo sapiens numb exon 9

<400> SEQUENCE: 106
uaauggcacu gacucagccu u 21

<210> SEQ ID NO 107
<211> LENGTH: 21
<212> TYPE: RNA
<213> ORGANISM: Homo sapiens
<220> FEATURE:
<223> OTHER INFORMATION: 107: target regions in region 1+2 of homo sapiens numb exon 9

<400> SEQUENCE: 107
aauggcacug acucagccuu c 21

<210> SEQ ID NO 108
<211> LENGTH: 21
<212> TYPE: RNA
<213> ORGANISM: Homo sapiens
<220> FEATURE:
<223> OTHER INFORMATION: 108: target regions in region 1+2 of homo sapiens numb exon 9

<400> SEQUENCE: 108
auggcacuga cucagccuuc c 21

<210> SEQ ID NO 109
<211> LENGTH: 21
<212> TYPE: RNA
<213> ORGANISM: Homo sapiens
<220> FEATURE:
<223> OTHER INFORMATION: 109: target regions in region 1+2 of homo sapiens numb exon 9

<400> SEQUENCE: 109
uggcacugac ucagccuucc a 21

<210> SEQ ID NO 110
<211> LENGTH: 21
<212> TYPE: RNA

<213> ORGANISM: Homo sapiens
<220> FEATURE:
<223> OTHER INFORMATION: 110: target regions in region 1+2 of homo
sapiens numb exon 9

<400> SEQUENCE: 110
ggcacugacu cagccuucca u 21

<210> SEQ ID NO 111
<211> LENGTH: 21
<212> TYPE: RNA
<213> ORGANISM: Homo sapiens
<220> FEATURE:
<223> OTHER INFORMATION: 111: target regions in region 1+2 of homo
sapiens numb exon 9

<400> SEQUENCE: 111
gcacugacuc agccuuccau g 21

<210> SEQ ID NO 112
<211> LENGTH: 21
<212> TYPE: RNA
<213> ORGANISM: Homo sapiens
<220> FEATURE:
<223> OTHER INFORMATION: 112: target regions in region 1+2 of homo
sapiens numb exon 9

<400> SEQUENCE: 112
cacugacuca gccuuccaug u 21

<210> SEQ ID NO 113
<211> LENGTH: 21
<212> TYPE: RNA
<213> ORGANISM: Homo sapiens
<220> FEATURE:
<223> OTHER INFORMATION: 113: target regions in region 1+2 of homo
sapiens numb exon 9

<400> SEQUENCE: 113
acugacucag ccuuccaugu g 21

<210> SEQ ID NO 114
<211> LENGTH: 21
<212> TYPE: RNA
<213> ORGANISM: Homo sapiens
<220> FEATURE:
<223> OTHER INFORMATION: 114: target regions in region 1+2 of homo
sapiens numb exon 9

<400> SEQUENCE: 114
cugacucagc cuuccaugug c 21

<210> SEQ ID NO 115
<211> LENGTH: 21
<212> TYPE: RNA
<213> ORGANISM: Homo sapiens
<220> FEATURE:
<223> OTHER INFORMATION: 115: target regions in region 1+2 of homo
sapiens numb exon 9

<400> SEQUENCE: 115
ugacucagcc uuccaugugc u 21

<210> SEQ ID NO 116
<211> LENGTH: 21
<212> TYPE: RNA
<213> ORGANISM: Homo sapiens
<220> FEATURE:
<223> OTHER INFORMATION: 116: target regions in region 1+2 of homo sapiens numb exon 9

<400> SEQUENCE: 116
gacucagccu uccaugugcu u 21

<210> SEQ ID NO 117
<211> LENGTH: 21
<212> TYPE: RNA
<213> ORGANISM: Homo sapiens
<220> FEATURE:
<223> OTHER INFORMATION: 117: target regions in region 1+2 of homo sapiens numb exon 9

<400> SEQUENCE: 117
acucagccuu ccaugugcuu g 21

<210> SEQ ID NO 118
<211> LENGTH: 21
<212> TYPE: RNA
<213> ORGANISM: Homo sapiens
<220> FEATURE:
<223> OTHER INFORMATION: 118: target regions in region 1+2 of homo sapiens numb exon 9

<400> SEQUENCE: 118
cucagccuuc caugugcuug c 21

<210> SEQ ID NO 119
<211> LENGTH: 21
<212> TYPE: RNA
<213> ORGANISM: Homo sapiens
<220> FEATURE:
<223> OTHER INFORMATION: 119: target regions in region 1+2 of homo sapiens numb exon 9

<400> SEQUENCE: 119
ucagccuucc augugcuugc u 21

<210> SEQ ID NO 120
<211> LENGTH: 21
<212> TYPE: RNA
<213> ORGANISM: Homo sapiens
<220> FEATURE:
<223> OTHER INFORMATION: 120: target regions in region 1+2 of homo sapiens numb exon 9

<400> SEQUENCE: 120
cagccuucca ugugcuugcu a 21

<210> SEQ ID NO 121
<211> LENGTH: 21
<212> TYPE: RNA
<213> ORGANISM: Homo sapiens
<220> FEATURE:
<223> OTHER INFORMATION: 121: target regions in region 1+2 of homo sapiens numb exon 9

<400> SEQUENCE: 121
agccuuccau gugcuugcua a 21

<210> SEQ ID NO 122
<211> LENGTH: 21
<212> TYPE: RNA
<213> ORGANISM: Homo sapiens
<220> FEATURE:

```
<223> OTHER INFORMATION: 122: target regions in region 1+2 of homo
      sapiens numb exon 9

<400> SEQUENCE: 122

gccuuccaug ugcuugcuaa g                                               21


<210> SEQ ID NO 123
<211> LENGTH: 21
<212> TYPE: RNA
<213> ORGANISM: Homo sapiens
<220> FEATURE:
<223> OTHER INFORMATION: 123: target regions in region 1+2 of homo
      sapiens numb exon 9

<400> SEQUENCE: 123

ccuuccaugu gcuugcuaag c                                               21


<210> SEQ ID NO 124
<211> LENGTH: 7
<212> TYPE: RNA
<213> ORGANISM: Homo sapiens
<220> FEATURE:
<223> OTHER INFORMATION: 124: Target regions in region 4+5 of Homo
      sapiens Numb exon 9

<400> SEQUENCE: 124

ccguagc                                                                7


<210> SEQ ID NO 125
<211> LENGTH: 7
<212> TYPE: RNA
<213> ORGANISM: Homo sapiens
<220> FEATURE:
<223> OTHER INFORMATION: 125: target regions in region 4+5 of homo
      sapiens numb exon 9

<400> SEQUENCE: 125

cguagca                                                                7


<210> SEQ ID NO 126
<211> LENGTH: 7
<212> TYPE: RNA
<213> ORGANISM: Homo sapiens
<220> FEATURE:
<223> OTHER INFORMATION: 126: target regions in region 4+5 of homo
      sapiens numb exon 9

<400> SEQUENCE: 126

guagcaa                                                                7


<210> SEQ ID NO 127
<211> LENGTH: 7
<212> TYPE: RNA
<213> ORGANISM: Homo sapiens
<220> FEATURE:
<223> OTHER INFORMATION: 127: target regions in region 4+5 of homo
      sapiens numb exon 9

<400> SEQUENCE: 127

uagcaau                                                                7


<210> SEQ ID NO 128
<211> LENGTH: 7
<212> TYPE: RNA
<213> ORGANISM: Homo sapiens
<220> FEATURE:
<223> OTHER INFORMATION: 128: target regions in region 4+5 of homo
```

sapiens numb exon 9

<400> SEQUENCE: 128 agcaaug 7

<210> SEQ ID NO 129
<211> LENGTH: 7
<212> TYPE: RNA
<213> ORGANISM: Homo sapiens
<220> FEATURE:
<223> OTHER INFORMATION: 129: target regions in region 4+5 of homo
sapiens numb exon 9

<400> SEQUENCE: 129 gcaaugc 7

<210> SEQ ID NO 130
<211> LENGTH: 7
<212> TYPE: RNA
<213> ORGANISM: Homo sapiens
<220> FEATURE:
<223> OTHER INFORMATION: 130: target regions in region 4+5 of homo
sapiens numb exon 9

<400> SEQUENCE: 130 caaugcc 7

<210> SEQ ID NO 131
<211> LENGTH: 7
<212> TYPE: RNA
<213> ORGANISM: Homo sapiens
<220> FEATURE:
<223> OTHER INFORMATION: 131: target regions in region 4+5 of homo
sapiens numb exon 9

<400> SEQUENCE: 131 aaugccu 7

<210> SEQ ID NO 132
<211> LENGTH: 7
<212> TYPE: RNA
<213> ORGANISM: Homo sapiens
<220> FEATURE:
<223> OTHER INFORMATION: 132: target regions in region 4+5 of homo
sapiens numb exon 9

<400> SEQUENCE: 132 augccug 7

<210> SEQ ID NO 133
<211> LENGTH: 7
<212> TYPE: RNA
<213> ORGANISM: Homo sapiens
<220> FEATURE:
<223> OTHER INFORMATION: 133: target regions in region 4+5 of homo
sapiens numb exon 9

<400> SEQUENCE: 133 ugccugu 7

<210> SEQ ID NO 134
<211> LENGTH: 7
<212> TYPE: RNA
<213> ORGANISM: Homo sapiens
<220> FEATURE:
<223> OTHER INFORMATION: 134: target regions in region 4+5 of homo
sapiens numb exon 9

<400> SEQUENCE: 134 gccugug 7

<210> SEQ ID NO 135
<211> LENGTH: 7
<212> TYPE: RNA
<213> ORGANISM: Homo sapiens
<220> FEATURE:
<223> OTHER INFORMATION: 135: target regions in region 4+5 of homo sapiens numb exon 9

<400> SEQUENCE: 135 ccugugc 7

<210> SEQ ID NO 136
<211> LENGTH: 7
<212> TYPE: RNA
<213> ORGANISM: Homo sapiens
<220> FEATURE:
<223> OTHER INFORMATION: 136: target regions in region 4+5 of homo sapiens numb exon 9

<400> SEQUENCE: 136 cugugcg 7

<210> SEQ ID NO 137
<211> LENGTH: 7
<212> TYPE: RNA
<213> ORGANISM: Homo sapiens
<220> FEATURE:
<223> OTHER INFORMATION: 137: target regions in region 4+5 of homo sapiens numb exon 9

<400> SEQUENCE: 137 ugugcgu 7

<210> SEQ ID NO 138
<211> LENGTH: 7
<212> TYPE: RNA
<213> ORGANISM: Homo sapiens
<220> FEATURE:
<223> OTHER INFORMATION: 138: target regions in region 4+5 of homo sapiens numb exon 9

<400> SEQUENCE: 138 gugcgug 7

<210> SEQ ID NO 139
<211> LENGTH: 7
<212> TYPE: RNA
<213> ORGANISM: Homo sapiens
<220> FEATURE:
<223> OTHER INFORMATION: 139: target regions in region 4+5 of homo sapiens numb exon 9

<400> SEQUENCE: 139 ugcguga 7

<210> SEQ ID NO 140
<211> LENGTH: 7
<212> TYPE: RNA
<213> ORGANISM: Homo sapiens
<220> FEATURE:
<223> OTHER INFORMATION: 140: target regions in region 4+5 of homo sapiens numb exon 9

<400> SEQUENCE: 140 gcgugaa 7

<210> SEQ ID NO 141
<211> LENGTH: 7
<212> TYPE: RNA
<213> ORGANISM: Homo sapiens
<220> FEATURE:
<223> OTHER INFORMATION: 141: target regions in region 4+5 of homo sapiens numb exon 9

<400> SEQUENCE: 141 cgugaaa 7

<210> SEQ ID NO 142
<211> LENGTH: 7
<212> TYPE: RNA
<213> ORGANISM: Homo sapiens
<220> FEATURE:
<223> OTHER INFORMATION: 142: target regions in region 4+5 of homo sapiens numb exon 9

<400> SEQUENCE: 142 gugaaac 7

<210> SEQ ID NO 143
<211> LENGTH: 7
<212> TYPE: RNA
<213> ORGANISM: Homo sapiens
<220> FEATURE:
<223> OTHER INFORMATION: 143: target regions in region 4+5 of homo sapiens numb exon 9

<400> SEQUENCE: 143 ugaaacc 7

<210> SEQ ID NO 144
<211> LENGTH: 7
<212> TYPE: RNA
<213> ORGANISM: Homo sapiens
<220> FEATURE:
<223> OTHER INFORMATION: 144: target regions in region 4+5 of homo sapiens numb exon 9

<400> SEQUENCE: 144 gaaacca 7

<210> SEQ ID NO 145
<211> LENGTH: 7
<212> TYPE: RNA
<213> ORGANISM: Homo sapiens
<220> FEATURE:
<223> OTHER INFORMATION: 145: target regions in region 4+5 of homo sapiens numb exon 9

<400> SEQUENCE: 145 aaaccaa 7

<210> SEQ ID NO 146
<211> LENGTH: 7
<212> TYPE: RNA
<213> ORGANISM: Homo sapiens
<220> FEATURE:
<223> OTHER INFORMATION: 146: target regions in region 4+5 of homo sapiens numb exon 9

<400> SEQUENCE: 146 aaccaac 7

<210> SEQ ID NO 147
<211> LENGTH: 7
<212> TYPE: RNA
<213> ORGANISM: Homo sapiens
<220> FEATURE:
<223> OTHER INFORMATION: 147: target regions in region 4+5 of homo sapiens numb exon 9

<400> SEQUENCE: 147 accaacc 7

<210> SEQ ID NO 148
<211> LENGTH: 7
<212> TYPE: RNA
<213> ORGANISM: Homo sapiens
<220> FEATURE:
<223> OTHER INFORMATION: 148: target regions in region 4+5 of homo sapiens numb exon 9

<400> SEQUENCE: 148 ccaaccc 7

<210> SEQ ID NO 149
<211> LENGTH: 7
<212> TYPE: RNA
<213> ORGANISM: Homo sapiens
<220> FEATURE:
<223> OTHER INFORMATION: 149: target regions in region 4+5 of homo sapiens numb exon 9

<400> SEQUENCE: 149 caacccu 7

<210> SEQ ID NO 150
<211> LENGTH: 7
<212> TYPE: RNA
<213> ORGANISM: Homo sapiens
<220> FEATURE:
<223> OTHER INFORMATION: 150: target regions in region 4+5 of homo sapiens numb exon 9

<400> SEQUENCE: 150 aacccuu 7

<210> SEQ ID NO 151
<211> LENGTH: 7
<212> TYPE: RNA
<213> ORGANISM: Homo sapiens
<220> FEATURE:
<223> OTHER INFORMATION: 151: target regions in region 4+5 of homo sapiens numb exon 9

<400> SEQUENCE: 151 acccuug 7

<210> SEQ ID NO 152
<211> LENGTH: 7
<212> TYPE: RNA
<213> ORGANISM: Homo sapiens
<220> FEATURE:
<223> OTHER INFORMATION: 152: target regions in region 4+5 of homo sapiens numb exon 9

<400> SEQUENCE: 152 cccuugg 7

<210> SEQ ID NO 153
<211> LENGTH: 7
<212> TYPE: RNA
<213> ORGANISM: Homo sapiens
<220> FEATURE:
<223> OTHER INFORMATION: 153: target regions in region 4+5 of homo sapiens numb exon 9

<400> SEQUENCE: 153 ccuuggg 7

<210> SEQ ID NO 154
<211> LENGTH: 7
<212> TYPE: RNA
<213> ORGANISM: Homo sapiens
<220> FEATURE:
<223> OTHER INFORMATION: 154: target regions in region 4+5 of homo sapiens numb exon 9

<400> SEQUENCE: 154 cuugggc 7

<210> SEQ ID NO 155
<211> LENGTH: 7
<212> TYPE: RNA
<213> ORGANISM: Homo sapiens
<220> FEATURE:
<223> OTHER INFORMATION: 155: target regions in region 4+5 of homo sapiens numb exon 9

<400> SEQUENCE: 155 uugggcc 7

<210> SEQ ID NO 156
<211> LENGTH: 7
<212> TYPE: RNA
<213> ORGANISM: Homo sapiens
<220> FEATURE:
<223> OTHER INFORMATION: 156: target regions in region 4+5 of homo sapiens numb exon 9

<400> SEQUENCE: 156 ugggccc 7

<210> SEQ ID NO 157
<211> LENGTH: 7
<212> TYPE: RNA
<213> ORGANISM: Homo sapiens
<220> FEATURE:
<223> OTHER INFORMATION: 157: target regions in region 4+5 of homo sapiens numb exon 9

<400> SEQUENCE: 157 gggccca 7

<210> SEQ ID NO 158
<211> LENGTH: 7
<212> TYPE: RNA
<213> ORGANISM: Homo sapiens
<220> FEATURE:
<223> OTHER INFORMATION: 158: target regions in region 4+5 of homo sapiens numb exon 9

<400> SEQUENCE: 158 ggcccau 7

<210> SEQ ID NO 159
<211> LENGTH: 7
<212> TYPE: RNA
<213> ORGANISM: Homo sapiens
<220> FEATURE:
<223> OTHER INFORMATION: 159: target regions in region 4+5 of homo sapiens numb exon 9

<400> SEQUENCE: 159 gcccaug 7

<210> SEQ ID NO 160
<211> LENGTH: 13
<212> TYPE: RNA
<213> ORGANISM: Homo sapiens
<220> FEATURE:
<223> OTHER INFORMATION: 160: target regions in region 4+5 of homo sapiens numb exon 9

<400> SEQUENCE: 160
ccguagcaau gcc 13

<210> SEQ ID NO 161
<211> LENGTH: 13
<212> TYPE: RNA
<213> ORGANISM: Homo sapiens
<220> FEATURE:
<223> OTHER INFORMATION: 161: target regions in region 4+5 of homo sapiens numb exon 9

<400> SEQUENCE: 161
cguagcaaug ccu 13

<210> SEQ ID NO 162
<211> LENGTH: 13
<212> TYPE: RNA
<213> ORGANISM: Homo sapiens
<220> FEATURE:
<223> OTHER INFORMATION: 162: target regions in region 4+5 of homo sapiens numb exon 9

<400> SEQUENCE: 162
guagcaaugc cug 13

<210> SEQ ID NO 163
<211> LENGTH: 13
<212> TYPE: RNA
<213> ORGANISM: Homo sapiens
<220> FEATURE:
<223> OTHER INFORMATION: 163: target regions in region 4+5 of homo sapiens numb exon 9

<400> SEQUENCE: 163
uagcaaugcc ugu 13

<210> SEQ ID NO 164
<211> LENGTH: 13
<212> TYPE: RNA
<213> ORGANISM: Homo sapiens
<220> FEATURE:
<223> OTHER INFORMATION: 164: target regions in region 4+5 of homo sapiens numb exon 9

<400> SEQUENCE: 164
agcaaugccu gug 13

<210> SEQ ID NO 165
<211> LENGTH: 13
<212> TYPE: RNA
<213> ORGANISM: Homo sapiens
<220> FEATURE:
<223> OTHER INFORMATION: 165: target regions in region 4+5 of homo sapiens numb exon 9

<400> SEQUENCE: 165
gcaaugccug ugc 13

<210> SEQ ID NO 166
<211> LENGTH: 13
<212> TYPE: RNA
<213> ORGANISM: Homo sapiens
<220> FEATURE:
<223> OTHER INFORMATION: 166: target regions in region 4+5 of homo sapiens numb exon 9

<400> SEQUENCE: 166
caaugccugu gcg 13

<210> SEQ ID NO 167
<211> LENGTH: 13
<212> TYPE: RNA
<213> ORGANISM: Homo sapiens
<220> FEATURE:
<223> OTHER INFORMATION: 167: target regions in region 4+5 of homo sapiens numb exon 9

<400> SEQUENCE: 167
aaugccugug cgu 13

<210> SEQ ID NO 168
<211> LENGTH: 13
<212> TYPE: RNA
<213> ORGANISM: Homo sapiens
<220> FEATURE:
<223> OTHER INFORMATION: 168: target regions in region 4+5 of homo sapiens numb exon 9

<400> SEQUENCE: 168 augccugugcgug 13

<210> SEQ ID NO 169
<211> LENGTH: 13
<212> TYPE: RNA
<213> ORGANISM: Homo sapiens
<220> FEATURE:
<223> OTHER INFORMATION: 169: target regions in region 4+5 of homo sapiens numb exon 9

<400> SEQUENCE: 169
ugccugugcg uga 13

<210> SEQ ID NO 170
<211> LENGTH: 13
<212> TYPE: RNA
<213> ORGANISM: Homo sapiens
<220> FEATURE:
<223> OTHER INFORMATION: 170: target regions in region 4+5 of homo sapiens numb exon 9

<400> SEQUENCE: 170
gccugugcgu gaa 13

<210> SEQ ID NO 171
<211> LENGTH: 13
<212> TYPE: RNA
<213> ORGANISM: Homo sapiens
<220> FEATURE:
<223> OTHER INFORMATION: 171: target regions in region 4+5 of homo sapiens numb exon 9

<400> SEQUENCE: 171
ccugugcgug aaa 13

<210> SEQ ID NO 172
<211> LENGTH: 13
<212> TYPE: RNA
<213> ORGANISM: Homo sapiens
<220> FEATURE:
<223> OTHER INFORMATION: 172: target regions in region 4+5 of homo sapiens numb exon 9

<400> SEQUENCE: 172
cugugcguga aac 13

<210> SEQ ID NO 173
<211> LENGTH: 13
<212> TYPE: RNA
<213> ORGANISM: Homo sapiens
<220> FEATURE:
<223> OTHER INFORMATION: 173: target regions in region 4+5 of homo sapiens numb exon 9

<400> SEQUENCE: 173
ugugcgugaa acc 13

<210> SEQ ID NO 174
<211> LENGTH: 13
<212> TYPE: RNA
<213> ORGANISM: Homo sapiens
<220> FEATURE:
<223> OTHER INFORMATION: 174: target regions in region 4+5 of homo sapiens numb exon 9

<400> SEQUENCE: 174
gugcgugaaa cca 13

<210> SEQ ID NO 175
<211> LENGTH: 13
<212> TYPE: RNA
<213> ORGANISM: Homo sapiens
<220> FEATURE:
<223> OTHER INFORMATION: 175: target regions in region 4+5 of homo sapiens numb exon 9

<400> SEQUENCE: 175
ugcgugaaac caa 13

<210> SEQ ID NO 176
<211> LENGTH: 13
<212> TYPE: RNA
<213> ORGANISM: Homo sapiens
<220> FEATURE:
<223> OTHER INFORMATION: 176: target regions in region 4+5 of homo sapiens numb exon 9

<400> SEQUENCE: 176
gcgugaaacc aac 13

<210> SEQ ID NO 177

<211> LENGTH: 13
<212> TYPE: RNA
<213> ORGANISM: Homo sapiens
<220> FEATURE:
<223> OTHER INFORMATION: 177: target regions in region 4+5 of homo sapiens numb exon 9

<400> SEQUENCE: 177
cgugaaacca acc 13

<210> SEQ ID NO 178
<211> LENGTH: 13
<212> TYPE: RNA
<213> ORGANISM: Homo sapiens
<220> FEATURE:
<223> OTHER INFORMATION: 178: target regions in region 4+5 of homo sapiens numb exon 9

<400> SEQUENCE: 178
gugaaaccaa ccc 13

<210> SEQ ID NO 179
<211> LENGTH: 13
<212> TYPE: RNA
<213> ORGANISM: Homo sapiens
<220> FEATURE:
<223> OTHER INFORMATION: 179: target regions in region 4+5 of homo sapiens numb exon 9

<400> SEQUENCE: 179
ugaaaccaac ccu 13

<210> SEQ ID NO 180
<211> LENGTH: 13
<212> TYPE: RNA
<213> ORGANISM: Homo sapiens
<220> FEATURE:
<223> OTHER INFORMATION: 180: target regions in region 4+5 of homo sapiens numb exon 9

<400> SEQUENCE: 180
gaaaccaacc cuu 13

<210> SEQ ID NO 181
<211> LENGTH: 13
<212> TYPE: RNA
<213> ORGANISM: Homo sapiens
<220> FEATURE:
<223> OTHER INFORMATION: 181: target regions in region 4+5 of homo sapiens numb exon 9

<400> SEQUENCE: 181
aaaccaaccc uug 13

<210> SEQ ID NO 182
<211> LENGTH: 13
<212> TYPE: RNA
<213> ORGANISM: Homo sapiens
<220> FEATURE:
<223> OTHER INFORMATION: 182: target regions in region 4+5 of homo sapiens numb exon 9

<400> SEQUENCE: 182
aaccaacccu ugg 13

<210> SEQ ID NO 183
<211> LENGTH: 13

```
<212> TYPE: RNA
<213> ORGANISM: Homo sapiens
<220> FEATURE:
<223> OTHER INFORMATION: 183: target regions in region 4+5 of homo
      sapiens numb exon 9

<400> SEQUENCE: 183

accaacccuu ggg                                                    13


<210> SEQ ID NO 184
<211> LENGTH: 13
<212> TYPE: RNA
<213> ORGANISM: Homo sapiens
<220> FEATURE:
<223> OTHER INFORMATION: 184: target regions in region 4+5 of homo
      sapiens numb exon 9

<400> SEQUENCE: 184

ccaacccuug ggc                                                    13


<210> SEQ ID NO 185
<211> LENGTH: 13
<212> TYPE: RNA
<213> ORGANISM: Homo sapiens
<220> FEATURE:
<223> OTHER INFORMATION: 185: target regions in region 4+5 of homo
      sapiens numb exon 9

<400> SEQUENCE: 185

caacccuugg gcc                                                    13


<210> SEQ ID NO 186
<211> LENGTH: 13
<212> TYPE: RNA
<213> ORGANISM: Homo sapiens
<220> FEATURE:
<223> OTHER INFORMATION: 186: target regions in region 4+5 of homo
      sapiens numb exon 9

<400> SEQUENCE: 186

aacccuuggg ccc                                                    13


<210> SEQ ID NO 187
<211> LENGTH: 13
<212> TYPE: RNA
<213> ORGANISM: Homo sapiens
<220> FEATURE:
<223> OTHER INFORMATION: 187: target regions in region 4+5 of homo
      sapiens numb exon 9

<400> SEQUENCE: 187

acccuugggc cca                                                    13


<210> SEQ ID NO 188
<211> LENGTH: 13
<212> TYPE: RNA
<213> ORGANISM: Homo sapiens
<220> FEATURE:
<223> OTHER INFORMATION: 188: target regions in region 4+5 of homo
      sapiens numb exon 9

<400> SEQUENCE: 188

cccuugggcc cau                                                    13


<210> SEQ ID NO 189
<211> LENGTH: 13
<212> TYPE: RNA
```

```
<213> ORGANISM: Homo sapiens
<220> FEATURE:
<223> OTHER INFORMATION: 189: target regions in region 4+5 of homo
      sapiens numb exon 9

<400> SEQUENCE: 189

ccuugggccc aug                                                     13


<210> SEQ ID NO 190
<211> LENGTH: 21
<212> TYPE: RNA
<213> ORGANISM: Homo sapiens
<220> FEATURE:
<223> OTHER INFORMATION: 190: target regions in region 4+5 of homo
      sapiens numb exon 9

<400> SEQUENCE: 190

ccguagcaau gccugugcgu g                                            21


<210> SEQ ID NO 191
<211> LENGTH: 21
<212> TYPE: RNA
<213> ORGANISM: Homo sapiens
<220> FEATURE:
<223> OTHER INFORMATION: 191: target regions in region 4+5 of homo
      sapiens numb exon 9

<400> SEQUENCE: 191

cguagcaaug ccugugcgug a                                            21


<210> SEQ ID NO 192
<211> LENGTH: 21
<212> TYPE: RNA
<213> ORGANISM: Homo sapiens
<220> FEATURE:
<223> OTHER INFORMATION: 192: target regions in region 4+5 of homo
      sapiens numb exon 9

<400> SEQUENCE: 192

guagcaaugc cugugcguga a                                            21


<210> SEQ ID NO 193
<211> LENGTH: 21
<212> TYPE: RNA
<213> ORGANISM: Homo sapiens
<220> FEATURE:
<223> OTHER INFORMATION: 193: target regions in region 4+5 of homo
      sapiens numb exon 9

<400> SEQUENCE: 193

uagcaaugcc ugugcgugaa a                                            21


<210> SEQ ID NO 194
<211> LENGTH: 21
<212> TYPE: RNA
<213> ORGANISM: Homo sapiens
<220> FEATURE:
<223> OTHER INFORMATION: 194: target regions in region 4+5 of homo
      sapiens numb exon 9

<400> SEQUENCE: 194

agcaaugccu gugcgugaaa c                                            21


<210> SEQ ID NO 195
<211> LENGTH: 21
<212> TYPE: RNA
<213> ORGANISM: Homo sapiens
```

<220> FEATURE:
<223> OTHER INFORMATION: 195: target regions in region 4+5 of homo sapiens numb exon 9

<400> SEQUENCE: 195
gcaaugccug ugcgugaaac c 21

<210> SEQ ID NO 196
<211> LENGTH: 21
<212> TYPE: RNA
<213> ORGANISM: Homo sapiens
<220> FEATURE:
<223> OTHER INFORMATION: 196: target regions in region 4+5 of homo sapiens numb exon 9

<400> SEQUENCE: 196
caaugccugu gcgugaaacc a 21

<210> SEQ ID NO 197
<211> LENGTH: 21
<212> TYPE: RNA
<213> ORGANISM: Homo sapiens
<220> FEATURE:
<223> OTHER INFORMATION: 197: target regions in region 4+5 of homo sapiens numb exon 9

<400> SEQUENCE: 197
aaugccugug cgugaaacca a 21

<210> SEQ ID NO 198
<211> LENGTH: 21
<212> TYPE: RNA
<213> ORGANISM: Homo sapiens
<220> FEATURE:
<223> OTHER INFORMATION: 198: target regions in region 4+5 of homo sapiens numb exon 9

<400> SEQUENCE: 198
augccugugc gugaaaccaa c 21

<210> SEQ ID NO 199
<211> LENGTH: 21
<212> TYPE: RNA
<213> ORGANISM: Homo sapiens
<220> FEATURE:
<223> OTHER INFORMATION: 199: target regions in region 4+5 of homo sapiens numb exon 9

<400> SEQUENCE: 199
ugccugugcg ugaaaccaac c 21

<210> SEQ ID NO 200
<211> LENGTH: 21
<212> TYPE: RNA
<213> ORGANISM: Homo sapiens
<220> FEATURE:
<223> OTHER INFORMATION: 200: target regions in region 4+5 of homo sapiens numb exon 9

<400> SEQUENCE: 200
gccugugcgu gaaaccaacc c 21

<210> SEQ ID NO 201
<211> LENGTH: 21
<212> TYPE: RNA
<213> ORGANISM: Homo sapiens
<220> FEATURE:

<223> OTHER INFORMATION: 201: target regions in region 4+5 of homo sapiens numb exon 9

<400> SEQUENCE: 201
ccugugcgug aaaccaaccc u 21

<210> SEQ ID NO 202
<211> LENGTH: 21
<212> TYPE: RNA
<213> ORGANISM: Homo sapiens
<220> FEATURE:
<223> OTHER INFORMATION: 202: target regions in region 4+5 of homo sapiens numb exon 9

<400> SEQUENCE: 202
cugugcguga aaccaacccu u 21

<210> SEQ ID NO 203
<211> LENGTH: 21
<212> TYPE: RNA
<213> ORGANISM: Homo sapiens
<220> FEATURE:
<223> OTHER INFORMATION: 203: target regions in region 4+5 of homo sapiens numb exon 9

<400> SEQUENCE: 203
ugugcgugaa accaacccuu g 21

<210> SEQ ID NO 204
<211> LENGTH: 21
<212> TYPE: RNA
<213> ORGANISM: Homo sapiens
<220> FEATURE:
<223> OTHER INFORMATION: 204: target regions in region 4+5 of homo sapiens numb exon 9

<400> SEQUENCE: 204
gugcgugaaa ccaacccuug g 21

<210> SEQ ID NO 205
<211> LENGTH: 21
<212> TYPE: RNA
<213> ORGANISM: Homo sapiens
<220> FEATURE:
<223> OTHER INFORMATION: 205: target regions in region 4+5 of homo sapiens numb exon 9

<400> SEQUENCE: 205
ugcgugaaac caacccuugg g 21

<210> SEQ ID NO 206
<211> LENGTH: 21
<212> TYPE: RNA
<213> ORGANISM: Homo sapiens
<220> FEATURE:
<223> OTHER INFORMATION: 206: target regions in region 4+5 of homo sapiens numb exon 9

<400> SEQUENCE: 206
gcgugaaacc aacccuuggg c 21

<210> SEQ ID NO 207
<211> LENGTH: 21
<212> TYPE: RNA
<213> ORGANISM: Homo sapiens
<220> FEATURE:
<223> OTHER INFORMATION: 207: target regions in region 4+5 of homo sapiens numb exon 9

<400> SEQUENCE: 207
cgugaaacca acccuugggc c 21

<210> SEQ ID NO 208
<211> LENGTH: 21
<212> TYPE: RNA
<213> ORGANISM: Homo sapiens
<220> FEATURE:
<223> OTHER INFORMATION: 208: target regions in region 4+5 of homo sapiens numb exon 9

<400> SEQUENCE: 208
gugaaaccaa cccuugggcc c 21

<210> SEQ ID NO 209
<211> LENGTH: 21
<212> TYPE: RNA
<213> ORGANISM: Homo sapiens
<220> FEATURE:
<223> OTHER INFORMATION: 209: target regions in region 4+5 of homo sapiens numb exon 9

<400> SEQUENCE: 209
ugaaaccaac ccuugggccc a 21

<210> SEQ ID NO 210
<211> LENGTH: 21
<212> TYPE: RNA
<213> ORGANISM: Homo sapiens
<220> FEATURE:
<223> OTHER INFORMATION: 210: target regions in region 4+5 of homo sapiens numb exon 9

<400> SEQUENCE: 210
gaaaccaacc cuugggccca u 21

<210> SEQ ID NO 211
<211> LENGTH: 21
<212> TYPE: RNA
<213> ORGANISM: Homo sapiens
<220> FEATURE:
<223> OTHER INFORMATION: 211: target regions in region 4+5 of homo sapiens numb exon 9

<400> SEQUENCE: 211
aaaccaaccc uugggcccau g 21

<210> SEQ ID NO 212
<211> LENGTH: 7
<212> TYPE: RNA
<213> ORGANISM: Homo sapiens
<220> FEATURE:
<223> OTHER INFORMATION: 212: target regions in region 6+7 of homo sapiens numb exon 9

<400> SEQUENCE: 212 ccccuga 7

<210> SEQ ID NO 213
<211> LENGTH: 7
<212> TYPE: RNA
<213> ORGANISM: Homo sapiens
<220> FEATURE:
<223> OTHER INFORMATION: 213: target regions in region 6+7 of homo sapiens numb exon 9

<400> SEQUENCE: 213 cccugau 7

<210> SEQ ID NO 214
<211> LENGTH: 7
<212> TYPE: RNA
<213> ORGANISM: Homo sapiens
<220> FEATURE:
<223> OTHER INFORMATION: 214: target regions in region 6+7 of homo sapiens numb exon 9

<400> SEQUENCE: 214 ccugaug 7

<210> SEQ ID NO 215
<211> LENGTH: 7
<212> TYPE: RNA
<213> ORGANISM: Homo sapiens
<220> FEATURE:
<223> OTHER INFORMATION: 215: target regions in region 6+7 of homo sapiens numb exon 9

<400> SEQUENCE: 215 cugaugc 7

<210> SEQ ID NO 216
<211> LENGTH: 7
<212> TYPE: RNA
<213> ORGANISM: Homo sapiens
<220> FEATURE:
<223> OTHER INFORMATION: 216: target regions in region 6+7 of homo sapiens numb exon 9

<400> SEQUENCE: 216 ugaugcu 7

<210> SEQ ID NO 217
<211> LENGTH: 7
<212> TYPE: RNA
<213> ORGANISM: Homo sapiens
<220> FEATURE:
<223> OTHER INFORMATION: 217: target regions in region 6+7 of homo sapiens numb exon 9

<400> SEQUENCE: 217 gaugcug 7

<210> SEQ ID NO 218
<211> LENGTH: 7
<212> TYPE: RNA
<213> ORGANISM: Homo sapiens
<220> FEATURE:
<223> OTHER INFORMATION: 218: target regions in region 6+7 of homo sapiens numb exon 9

<400> SEQUENCE: 218 augcugc 7

<210> SEQ ID NO 219
<211> LENGTH: 7
<212> TYPE: RNA
<213> ORGANISM: Homo sapiens
<220> FEATURE:
<223> OTHER INFORMATION: 219: target regions in region 6+7 of homo sapiens numb exon 9

<400> SEQUENCE: 219 ugcugcu 7

<210> SEQ ID NO 220
<211> LENGTH: 7
<212> TYPE: RNA
<213> ORGANISM: Homo sapiens
<220> FEATURE:
<223> OTHER INFORMATION: 220: target regions in region 6+7 of homo sapiens numb exon 9

<400> SEQUENCE: 220 gcugcua 7

<210> SEQ ID NO 221
<211> LENGTH: 7
<212> TYPE: RNA
<213> ORGANISM: Homo sapiens
<220> FEATURE:
<223> OTHER INFORMATION: 221: target regions in region 6+7 of homo sapiens numb exon 9

<400> SEQUENCE: 221 cugcuaa 7

<210> SEQ ID NO 222
<211> LENGTH: 7
<212> TYPE: RNA
<213> ORGANISM: Homo sapiens
<220> FEATURE:
<223> OTHER INFORMATION: 222: target regions in region 6+7 of homo sapiens numb exon 9

<400> SEQUENCE: 222 ugcuaac 7

<210> SEQ ID NO 223
<211> LENGTH: 7
<212> TYPE: RNA
<213> ORGANISM: Homo sapiens
<220> FEATURE:
<223> OTHER INFORMATION: 223: target regions in region 6+7 of homo sapiens numb exon 9

<400> SEQUENCE: 223 gcuaaca 7

<210> SEQ ID NO 224
<211> LENGTH: 7
<212> TYPE: RNA
<213> ORGANISM: Homo sapiens
<220> FEATURE:
<223> OTHER INFORMATION: 224: target regions in region 6+7 of homo sapiens numb exon 9

<400> SEQUENCE: 224 cuaacaa 7

<210> SEQ ID NO 225
<211> LENGTH: 7
<212> TYPE: RNA
<213> ORGANISM: Homo sapiens
<220> FEATURE:
<223> OTHER INFORMATION: 225: target regions in region 6+7 of homo sapiens numb exon 9

<400> SEQUENCE: 225 uaacaag 7

<210> SEQ ID NO 226
<211> LENGTH: 7
<212> TYPE: RNA
<213> ORGANISM: Homo sapiens
<220> FEATURE:
<223> OTHER INFORMATION: 226: target regions in region 6+7 of homo sapiens numb exon 9

<400> SEQUENCE: 226 aacaagg 7

<210> SEQ ID NO 227
<211> LENGTH: 7
<212> TYPE: RNA
<213> ORGANISM: Homo sapiens
<220> FEATURE:
<223> OTHER INFORMATION: 227: target regions in region 6+7 of homo sapiens numb exon 9

<400> SEQUENCE: 227 acaagga 7

<210> SEQ ID NO 228
<211> LENGTH: 7
<212> TYPE: RNA
<213> ORGANISM: Homo sapiens
<220> FEATURE:
<223> OTHER INFORMATION: 228: target regions in region 6+7 of homo sapiens numb exon 9

<400> SEQUENCE: 228 caaggaa 7

<210> SEQ ID NO 229
<211> LENGTH: 7
<212> TYPE: RNA
<213> ORGANISM: Homo sapiens
<220> FEATURE:
<223> OTHER INFORMATION: 229: target regions in region 6+7 of homo sapiens numb exon 9

<400> SEQUENCE: 229 aaggaaa 7

<210> SEQ ID NO 230
<211> LENGTH: 7
<212> TYPE: RNA
<213> ORGANISM: Homo sapiens
<220> FEATURE:
<223> OTHER INFORMATION: 230: target regions in region 6+7 of homo sapiens numb exon 9

<400> SEQUENCE: 230 aggaaau 7

<210> SEQ ID NO 231
<211> LENGTH: 7
<212> TYPE: RNA
<213> ORGANISM: Homo sapiens
<220> FEATURE:
<223> OTHER INFORMATION: 231: target regions in region 6+7 of homo sapiens numb exon 9

<400> SEQUENCE: 231 ggaaauu 7

<210> SEQ ID NO 232
<211> LENGTH: 7
<212> TYPE: RNA
<213> ORGANISM: Homo sapiens
<220> FEATURE:
<223> OTHER INFORMATION: 232: target regions in region 6+7 of homo sapiens numb exon 9

<400> SEQUENCE: 232 gaaauug 7

<210> SEQ ID NO 233
<211> LENGTH: 7
<212> TYPE: RNA
<213> ORGANISM: Homo sapiens
<220> FEATURE:
<223> OTHER INFORMATION: 233: target regions in region 6+7 of homo sapiens numb exon 9

<400> SEQUENCE: 233 aaauugc 7

<210> SEQ ID NO 234
<211> LENGTH: 7
<212> TYPE: RNA
<213> ORGANISM: Homo sapiens
<220> FEATURE:
<223> OTHER INFORMATION: 234: target regions in region 6+7 of homo sapiens numb exon 9

<400> SEQUENCE: 234 aauugca 7

<210> SEQ ID NO 235
<211> LENGTH: 7
<212> TYPE: RNA
<213> ORGANISM: Homo sapiens
<220> FEATURE:
<223> OTHER INFORMATION: 235: target regions in region 6+7 of homo sapiens numb exon 9

<400> SEQUENCE: 235 auugcag 7

<210> SEQ ID NO 236
<211> LENGTH: 7
<212> TYPE: RNA
<213> ORGANISM: Homo sapiens
<220> FEATURE:
<223> OTHER INFORMATION: 236: target regions in region 6+7 of homo sapiens numb exon 9

<400> SEQUENCE: 236 uugcagc 7

<210> SEQ ID NO 237
<211> LENGTH: 7
<212> TYPE: RNA
<213> ORGANISM: Homo sapiens
<220> FEATURE:
<223> OTHER INFORMATION: 237: target regions in region 6+7 of homo sapiens numb exon 9

<400> SEQUENCE: 237 ugcagcc 7

<210> SEQ ID NO 238
<211> LENGTH: 7
<212> TYPE: RNA
<213> ORGANISM: Homo sapiens
<220> FEATURE:
<223> OTHER INFORMATION: 238: target regions in region 6+7 of homo sapiens numb exon 9

<400> SEQUENCE: 238 gcagcca 7

<210> SEQ ID NO 239
<211> LENGTH: 7
<212> TYPE: RNA
<213> ORGANISM: Homo sapiens
<220> FEATURE:
<223> OTHER INFORMATION: 239: target regions in region 6+7 of homo sapiens numb exon 9

<400> SEQUENCE: 239 cagccac 7

<210> SEQ ID NO 240
<211> LENGTH: 7
<212> TYPE: RNA
<213> ORGANISM: Homo sapiens
<220> FEATURE:
<223> OTHER INFORMATION: 240: target regions in region 6+7 of homo sapiens numb exon 9

<400> SEQUENCE: 240 agccaca 7

<210> SEQ ID NO 241
<211> LENGTH: 7
<212> TYPE: RNA
<213> ORGANISM: Homo sapiens
<220> FEATURE:
<223> OTHER INFORMATION: 241: target regions in region 6+7 of homo sapiens numb exon 9

<400> SEQUENCE: 241 gccacau 7

<210> SEQ ID NO 242
<211> LENGTH: 7
<212> TYPE: RNA
<213> ORGANISM: Homo sapiens
<220> FEATURE:
<223> OTHER INFORMATION: 242: target regions in region 6+7 of homo sapiens numb exon 9

<400> SEQUENCE: 242 ccacaug 7

<210> SEQ ID NO 243
<211> LENGTH: 7
<212> TYPE: RNA
<213> ORGANISM: Homo sapiens
<220> FEATURE:
<223> OTHER INFORMATION: 243: target regions in region 6+7 of homo sapiens numb exon 9

<400> SEQUENCE: 243 cacaugu 7

<210> SEQ ID NO 244
<211> LENGTH: 7
<212> TYPE: RNA
<213> ORGANISM: Homo sapiens
<220> FEATURE:
<223> OTHER INFORMATION: 244: target regions in region 6+7 of homo sapiens numb exon 9

<400> SEQUENCE: 244 acauguu 7

<210> SEQ ID NO 245
<211> LENGTH: 7
<212> TYPE: RNA
<213> ORGANISM: Homo sapiens
<220> FEATURE:
<223> OTHER INFORMATION: 245: target regions in region 6+7 of homo sapiens numb exon 9

<400> SEQUENCE: 245 cauguuc 7

<210> SEQ ID NO 246
<211> LENGTH: 7
<212> TYPE: RNA
<213> ORGANISM: Homo sapiens
<220> FEATURE:
<223> OTHER INFORMATION: 246: target regions in region 6+7 of homo sapiens numb exon 9

<400> SEQUENCE: 246 auguucg 7

<210> SEQ ID NO 247
<211> LENGTH: 7
<212> TYPE: RNA
<213> ORGANISM: Homo sapiens
<220> FEATURE:
<223> OTHER INFORMATION: 247: target regions in region 6+7 of homo sapiens numb exon 9

<400> SEQUENCE: 247 uguucgg 7

<210> SEQ ID NO 248
<211> LENGTH: 13
<212> TYPE: RNA
<213> ORGANISM: Homo sapiens
<220> FEATURE:
<223> OTHER INFORMATION: 248: target regions in region 6+7 of homo sapiens numb exon 9

<400> SEQUENCE: 248
ccccugaugc ugc 13

<210> SEQ ID NO 249
<211> LENGTH: 13
<212> TYPE: RNA
<213> ORGANISM: Homo sapiens
<220> FEATURE:
<223> OTHER INFORMATION: 249: target regions in region 6+7 of homo sapiens numb exon 9

<400> SEQUENCE: 249
cccugaugcu gcu 13

<210> SEQ ID NO 250
<211> LENGTH: 13
<212> TYPE: RNA
<213> ORGANISM: Homo sapiens
<220> FEATURE:
<223> OTHER INFORMATION: 250: target regions in region 6+7 of homo sapiens numb exon 9

<400> SEQUENCE: 250
ccugaugcug cua 13

<210> SEQ ID NO 251
<211> LENGTH: 13
<212> TYPE: RNA
<213> ORGANISM: Homo sapiens
<220> FEATURE:
<223> OTHER INFORMATION: 251: target regions in region 6+7 of homo sapiens numb exon 9

<400> SEQUENCE: 251
cugaugcugc uaa 13

<210> SEQ ID NO 252
<211> LENGTH: 13
<212> TYPE: RNA
<213> ORGANISM: Homo sapiens
<220> FEATURE:
<223> OTHER INFORMATION: 252: target regions in region 6+7 of homo sapiens numb exon 9

<400> SEQUENCE: 252
ugaugcugcu aac 13

<210> SEQ ID NO 253
<211> LENGTH: 13
<212> TYPE: RNA
<213> ORGANISM: Homo sapiens
<220> FEATURE:
<223> OTHER INFORMATION: 253: target regions in region 6+7 of homo sapiens numb exon 9

<400> SEQUENCE: 253
gaugcugcua aca 13

<210> SEQ ID NO 254
<211> LENGTH: 13
<212> TYPE: RNA
<213> ORGANISM: Homo sapiens
<220> FEATURE:
<223> OTHER INFORMATION: 254: target regions in region 6+7 of homo sapiens numb exon 9

<400> SEQUENCE: 254
augcugcuaa caa 13

<210> SEQ ID NO 255
<211> LENGTH: 13
<212> TYPE: RNA
<213> ORGANISM: Homo sapiens
<220> FEATURE:
<223> OTHER INFORMATION: 255: target regions in region 6+7 of homo sapiens numb exon 9

<400> SEQUENCE: 255
ugcugcuaac aag 13

<210> SEQ ID NO 256

<211> LENGTH: 13
<212> TYPE: RNA
<213> ORGANISM: Homo sapiens
<220> FEATURE:
<223> OTHER INFORMATION: 256: target regions in region 6+7 of homo sapiens numb exon 9

<400> SEQUENCE: 256
gcugcuaaca agg 13

<210> SEQ ID NO 257
<211> LENGTH: 13
<212> TYPE: RNA
<213> ORGANISM: Homo sapiens
<220> FEATURE:
<223> OTHER INFORMATION: 257: target regions in region 6+7 of homo sapiens numb exon 9

<400> SEQUENCE: 257
cugcuaacaa gga 13

<210> SEQ ID NO 258
<211> LENGTH: 13
<212> TYPE: RNA
<213> ORGANISM: Homo sapiens
<220> FEATURE:
<223> OTHER INFORMATION: 258: target regions in region 6+7 of homo sapiens numb exon 9

<400> SEQUENCE: 258
ugcuaacaag gaa 13

<210> SEQ ID NO 259
<211> LENGTH: 13
<212> TYPE: RNA
<213> ORGANISM: Homo sapiens
<220> FEATURE:
<223> OTHER INFORMATION: 259: target regions in region 6+7 of homo sapiens numb exon 9

<400> SEQUENCE: 259
gcuaacaagg aaa 13

<210> SEQ ID NO 260
<211> LENGTH: 13
<212> TYPE: RNA
<213> ORGANISM: Homo sapiens
<220> FEATURE:
<223> OTHER INFORMATION: 260: target regions in region 6+7 of homo sapiens numb exon 9

<400> SEQUENCE: 260
cuaacaagga aau 13

<210> SEQ ID NO 261
<211> LENGTH: 13
<212> TYPE: RNA
<213> ORGANISM: Homo sapiens
<220> FEATURE:
<223> OTHER INFORMATION: 261: target regions in region 6+7 of homo sapiens numb exon 9

<400> SEQUENCE: 261
uaacaaggaa auu 13

<210> SEQ ID NO 262
<211> LENGTH: 13

<212> TYPE: RNA
<213> ORGANISM: Homo sapiens
<220> FEATURE:
<223> OTHER INFORMATION: 262: target regions in region 6+7 of homo sapiens numb exon 9

<400> SEQUENCE: 262
aacaaggaaa uug 13

<210> SEQ ID NO 263
<211> LENGTH: 13
<212> TYPE: RNA
<213> ORGANISM: Homo sapiens
<220> FEATURE:
<223> OTHER INFORMATION: 263: target regions in region 6+7 of homo sapiens numb exon 9

<400> SEQUENCE: 263
acaaggaaau ugc 13

<210> SEQ ID NO 264
<211> LENGTH: 13
<212> TYPE: RNA
<213> ORGANISM: Homo sapiens
<220> FEATURE:
<223> OTHER INFORMATION: 264: target regions in region 6+7 of homo sapiens numb exon 9

<400> SEQUENCE: 264
caaggaaauu gca 13

<210> SEQ ID NO 265
<211> LENGTH: 13
<212> TYPE: RNA
<213> ORGANISM: Homo sapiens
<220> FEATURE:
<223> OTHER INFORMATION: 265: target regions in region 6+7 of homo sapiens numb exon 9

<400> SEQUENCE: 265
aaggaaauug cag 13

<210> SEQ ID NO 266
<211> LENGTH: 13
<212> TYPE: RNA
<213> ORGANISM: Homo sapiens
<220> FEATURE:
<223> OTHER INFORMATION: 266: target regions in region 6+7 of homo sapiens numb exon 9

<400> SEQUENCE: 266
aggaaauugc agc 13

<210> SEQ ID NO 267
<211> LENGTH: 13
<212> TYPE: RNA
<213> ORGANISM: Homo sapiens
<220> FEATURE:
<223> OTHER INFORMATION: 267: target regions in region 6+7 of homo sapiens numb exon 9

<400> SEQUENCE: 267
ggaaauugca gcc 13

<210> SEQ ID NO 268
<211> LENGTH: 13
<212> TYPE: RNA

<213> ORGANISM: Homo sapiens
<220> FEATURE:
<223> OTHER INFORMATION: 268: target regions in region 6+7 of homo sapiens numb exon 9

<400> SEQUENCE: 268
gaaauugcag cca 13

<210> SEQ ID NO 269
<211> LENGTH: 13
<212> TYPE: RNA
<213> ORGANISM: Homo sapiens
<220> FEATURE:
<223> OTHER INFORMATION: 269: target regions in region 6+7 of homo sapiens numb exon 9

<400> SEQUENCE: 269
aaauugcagc cac 13

<210> SEQ ID NO 270
<211> LENGTH: 13
<212> TYPE: RNA
<213> ORGANISM: Homo sapiens
<220> FEATURE:
<223> OTHER INFORMATION: 270: target regions in region 6+7 of homo sapiens numb exon 9

<400> SEQUENCE: 270
aauugcagcc aca 13

<210> SEQ ID NO 271
<211> LENGTH: 13
<212> TYPE: RNA
<213> ORGANISM: Homo sapiens
<220> FEATURE:
<223> OTHER INFORMATION: 271: target regions in region 6+7 of homo sapiens numb exon 9

<400> SEQUENCE: 271
auugcagcca cau 13

<210> SEQ ID NO 272
<211> LENGTH: 13
<212> TYPE: RNA
<213> ORGANISM: Homo sapiens
<220> FEATURE:
<223> OTHER INFORMATION: 272: target regions in region 6+7 of homo sapiens numb exon 9

<400> SEQUENCE: 272
uugcagccac aug 13

<210> SEQ ID NO 273
<211> LENGTH: 13
<212> TYPE: RNA
<213> ORGANISM: Homo sapiens
<220> FEATURE:
<223> OTHER INFORMATION: 273: target regions in region 6+7 of homo sapiens numb exon 9

<400> SEQUENCE: 273
ugcagccaca ugu 13

<210> SEQ ID NO 274
<211> LENGTH: 13
<212> TYPE: RNA
<213> ORGANISM: Homo sapiens
<220> FEATURE:
<223> OTHER INFORMATION: 274: target regions in region 6+7 of homo sapiens numb exon 9

<400> SEQUENCE: 274
gcagccacau guu 13

<210> SEQ ID NO 275
<211> LENGTH: 13
<212> TYPE: RNA
<213> ORGANISM: Homo sapiens
<220> FEATURE:
<223> OTHER INFORMATION: 275: target regions in region 6+7 of homo sapiens numb exon 9

<400> SEQUENCE: 275
cagccacaug uuc 13

<210> SEQ ID NO 276
<211> LENGTH: 13
<212> TYPE: RNA
<213> ORGANISM: Homo sapiens
<220> FEATURE:
<223> OTHER INFORMATION: 276: target regions in region 6+7 of homo sapiens numb exon 9

<400> SEQUENCE: 276
agccacaugu ucg 13

<210> SEQ ID NO 277
<211> LENGTH: 13
<212> TYPE: RNA
<213> ORGANISM: Homo sapiens
<220> FEATURE:
<223> OTHER INFORMATION: 277: target regions in region 6+7 of homo sapiens numb exon 9

<400> SEQUENCE: 277
gccacauguu cgg 13

<210> SEQ ID NO 278
<211> LENGTH: 21
<212> TYPE: RNA
<213> ORGANISM: Homo sapiens
<220> FEATURE:
<223> OTHER INFORMATION: 278: target regions in region 6+7 of homo sapiens numb exon 9

<400> SEQUENCE: 278
ccccugaugc ugcuaacaag g 21

<210> SEQ ID NO 279
<211> LENGTH: 21
<212> TYPE: RNA
<213> ORGANISM: Homo sapiens
<220> FEATURE:
<223> OTHER INFORMATION: 279: target regions in region 6+7 of homo sapiens numb exon 9

<400> SEQUENCE: 279
cccugaugcu gcuaacaagg a 21

<210> SEQ ID NO 280
<211> LENGTH: 21
<212> TYPE: RNA
<213> ORGANISM: Homo sapiens
<220> FEATURE:

<223> OTHER INFORMATION: 280: target regions in region 6+7 of homo sapiens numb exon 9

<400> SEQUENCE: 280
ccugaugcug cuaacaagga a 21

<210> SEQ ID NO 281
<211> LENGTH: 21
<212> TYPE: RNA
<213> ORGANISM: Homo sapiens
<220> FEATURE:
<223> OTHER INFORMATION: 281: target regions in region 6+7 of homo sapiens numb exon 9

<400> SEQUENCE: 281
cugaugcugc uaacaaggaa a 21

<210> SEQ ID NO 282
<211> LENGTH: 21
<212> TYPE: RNA
<213> ORGANISM: Homo sapiens
<220> FEATURE:
<223> OTHER INFORMATION: 282: target regions in region 6+7 of homo sapiens numb exon 9

<400> SEQUENCE: 282
ugaugcugcu aacaaggaaa u 21

<210> SEQ ID NO 283
<211> LENGTH: 21
<212> TYPE: RNA
<213> ORGANISM: Homo sapiens
<220> FEATURE:
<223> OTHER INFORMATION: 283: target regions in region 6+7 of homo sapiens numb exon 9

<400> SEQUENCE: 283
gaugcugcua acaaggaaau u 21

<210> SEQ ID NO 284
<211> LENGTH: 21
<212> TYPE: RNA
<213> ORGANISM: Homo sapiens
<220> FEATURE:
<223> OTHER INFORMATION: 284: target regions in region 6+7 of homo sapiens numb exon 9

<400> SEQUENCE: 284
augcugcuaa caaggaaauu g 21

<210> SEQ ID NO 285
<211> LENGTH: 21
<212> TYPE: RNA
<213> ORGANISM: Homo sapiens
<220> FEATURE:
<223> OTHER INFORMATION: 285: target regions in region 6+7 of homo sapiens numb exon 9

<400> SEQUENCE: 285
ugcugcuaac aaggaaauug c 21

<210> SEQ ID NO 286
<211> LENGTH: 21
<212> TYPE: RNA
<213> ORGANISM: Homo sapiens
<220> FEATURE:
<223> OTHER INFORMATION: 286: target regions in region 6+7 of homo sapiens numb exon 9

<400> SEQUENCE: 286
gcugcuaaca aggaaauugc a 21

<210> SEQ ID NO 287
<211> LENGTH: 21
<212> TYPE: RNA
<213> ORGANISM: Homo sapiens
<220> FEATURE:
<223> OTHER INFORMATION: 287: target regions in region 6+7 of homo sapiens numb exon 9

<400> SEQUENCE: 287
cugcuaacaa ggaaauugca g 21

<210> SEQ ID NO 288
<211> LENGTH: 21
<212> TYPE: RNA
<213> ORGANISM: Homo sapiens
<220> FEATURE:
<223> OTHER INFORMATION: 288: target regions in region 6+7 of homo sapiens numb exon 9

<400> SEQUENCE: 288
ugcuaacaag gaaauugcag c 21

<210> SEQ ID NO 289
<211> LENGTH: 21
<212> TYPE: RNA
<213> ORGANISM: Homo sapiens
<220> FEATURE:
<223> OTHER INFORMATION: 289: target regions in region 6+7 of homo sapiens numb exon 9

<400> SEQUENCE: 289
gcuaacaagg aaauugcagc c 21

<210> SEQ ID NO 290
<211> LENGTH: 21
<212> TYPE: RNA
<213> ORGANISM: Homo sapiens
<220> FEATURE:
<223> OTHER INFORMATION: 290: target regions in region 6+7 of homo sapiens numb exon 9

<400> SEQUENCE: 290
cuaacaagga aauugcagcc a 21

<210> SEQ ID NO 291
<211> LENGTH: 21
<212> TYPE: RNA
<213> ORGANISM: Homo sapiens
<220> FEATURE:
<223> OTHER INFORMATION: 291: target regions in region 6+7 of homo sapiens numb exon 9

<400> SEQUENCE: 291
uaacaaggaa auugcagcca c 21

<210> SEQ ID NO 292
<211> LENGTH: 21
<212> TYPE: RNA
<213> ORGANISM: Homo sapiens
<220> FEATURE:
<223> OTHER INFORMATION: 292: target regions in region 6+7 of homo sapiens numb exon 9

<400> SEQUENCE: 292
aacaaggaaa uugcagccac a 21

<210> SEQ ID NO 293
<211> LENGTH: 21
<212> TYPE: RNA
<213> ORGANISM: Homo sapiens
<220> FEATURE:
<223> OTHER INFORMATION: 293: target regions in region 6+7 of homo sapiens numb exon 9

<400> SEQUENCE: 293
acaaggaaau ugcagccaca u 21

<210> SEQ ID NO 294
<211> LENGTH: 21
<212> TYPE: RNA
<213> ORGANISM: Homo sapiens
<220> FEATURE:
<223> OTHER INFORMATION: 294: target regions in region 6+7 of homo sapiens numb exon 9

<400> SEQUENCE: 294 caaggaaau ugcagccacau g 21

<210> SEQ ID NO 295
<211> LENGTH: 21
<212> TYPE: RNA
<213> ORGANISM: Homo sapiens
<220> FEATURE:
<223> OTHER INFORMATION: 295: target regions in region 6+7 of homo sapiens numb exon 9

<400> SEQUENCE: 295 aaggaaauu gcagccacaug u 21

<210> SEQ ID NO 296
<211> LENGTH: 21
<212> TYPE: RNA
<213> ORGANISM: Homo sapiens
<220> FEATURE:
<223> OTHER INFORMATION: 296: target regions in region 6+7 of homo sapiens numb exon 9

<400> SEQUENCE: 296 aggaaauug cagccacaugu u 21

<210> SEQ ID NO 297
<211> LENGTH: 21
<212> TYPE: RNA
<213> ORGANISM: Homo sapiens
<220> FEATURE:
<223> OTHER INFORMATION: 297: target regions in region 6+7 of homo sapiens numb exon 9

<400> SEQUENCE: 297 ggaaauugc agccacauguu c 21

<210> SEQ ID NO 298
<211> LENGTH: 21
<212> TYPE: RNA
<213> ORGANISM: Homo sapiens
<220> FEATURE:
<223> OTHER INFORMATION: 298: target regions in region 6+7 of homo sapiens numb exon 9

<400> SEQUENCE: 298
gaaauugcag ccacauguuc g 21

<210> SEQ ID NO 299
<211> LENGTH: 21
<212> TYPE: RNA
<213> ORGANISM: Homo sapiens
<220> FEATURE:
<223> OTHER INFORMATION: 299: target regions in region 6+7 of homo sapiens numb exon 9

<400> SEQUENCE: 299
aaauugcagc cacauguucg g 21

<210> SEQ ID NO 300
<211> LENGTH: 11
<212> TYPE: DNA
<213> ORGANISM: Homo sapiens
<220> FEATURE:
<223> OTHER INFORMATION: Potential binding site of SF1/BBP in NUMB exon 9

<400> SEQUENCE: 300
ggcactgact c 11

<210> SEQ ID NO 301
<211> LENGTH: 11
<212> TYPE: DNA
<213> ORGANISM: Artificial Sequence
<220> FEATURE:
<223> OTHER INFORMATION: RG6-NUMB minigene WT

<400> SEQUENCE: 301
ggcactgact c 11

<210> SEQ ID NO 302
<211> LENGTH: 12
<212> TYPE: DNA
<213> ORGANISM: Artificial Sequence
<220> FEATURE:
<223> OTHER INFORMATION: RG6-NUMB minigene Mut3

<400> SEQUENCE: 302
ggcactcacc tc 12

<210> SEQ ID NO 303
<211> LENGTH: 11
<212> TYPE: DNA
<213> ORGANISM: Artificial Sequence
<220> FEATURE:
<223> OTHER INFORMATION: RG6-NUMB minigene Mut 4

<400> SEQUENCE: 303
ggcaccgact c 11

<210> SEQ ID NO 304
<211> LENGTH: 12
<212> TYPE: DNA
<213> ORGANISM: Artificial Sequence
<220> FEATURE:
<223> OTHER INFORMATION: RG6-NUMB minigene Mut 1

<400> SEQUENCE: 304
ggtactgacc tc 12

<210> SEQ ID NO 305
<211> LENGTH: 50
<212> TYPE: RNA
<213> ORGANISM: Homo sapiens
<220> FEATURE:
<223> OTHER INFORMATION: Region 1+2+2-3 of Homo sapiens Numb exon 9 (targeted by by AON1 - SEQ ID NO: 12; AON2 SEQ ID NO: 13; AON1-2 - SEQ ID NO: 19; and AON2-3 - SEQ ID NO:20)

<400> SEQUENCE: 305
cuaauggcac ugacucagcc uuccaugugc uugcuaagcc agcccauacu 50

<210> SEQ ID NO 306
<211> LENGTH: 7
<212> TYPE: RNA
<213> ORGANISM: Homo sapiens
<220> FEATURE:
<223> OTHER INFORMATION: 306: Target regions in region 1+2+2-3 of Homo sapiens Numb exon 9

<400> SEQUENCE: 306 cuaagcc 7

<210> SEQ ID NO 307
<211> LENGTH: 7
<212> TYPE: RNA
<213> ORGANISM: Homo sapiens
<220> FEATURE:
<223> OTHER INFORMATION: 307: Target regions in region 1+2+2-3 of Homo sapiens Numb exon 9

<400> SEQUENCE: 307 uaagcca 7

<210> SEQ ID NO 308
<211> LENGTH: 7
<212> TYPE: RNA
<213> ORGANISM: Homo sapiens
<220> FEATURE:
<223> OTHER INFORMATION: 308: target regions in region 1+2+2-3 of homo sapiens numb exon 9

<400> SEQUENCE: 308 aagccag 7

<210> SEQ ID NO 309
<211> LENGTH: 7
<212> TYPE: RNA
<213> ORGANISM: Homo sapiens
<220> FEATURE:
<223> OTHER INFORMATION: 309: target regions in region 1+2+2-3 of homo sapiens numb exon 9

<400> SEQUENCE: 309 agccagc 7

<210> SEQ ID NO 310
<211> LENGTH: 7
<212> TYPE: RNA
<213> ORGANISM: Homo sapiens
<220> FEATURE:
<223> OTHER INFORMATION: 310: target regions in region 1+2+2-3 of homo sapiens numb exon 9

<400> SEQUENCE: 310 gccagcc 7

<210> SEQ ID NO 311
<211> LENGTH: 7
<212> TYPE: RNA
<213> ORGANISM: Homo sapiens
<220> FEATURE:
<223> OTHER INFORMATION: 311: target regions in region 1+2+2-3 of homo sapiens numb exon 9

<400> SEQUENCE: 311 ccagccc 7

<210> SEQ ID NO 312
<211> LENGTH: 7
<212> TYPE: RNA
<213> ORGANISM: Homo sapiens
<220> FEATURE:
<223> OTHER INFORMATION: 312: target regions in region 1+2+2-3 of homo sapiens numb exon 9

<400> SEQUENCE: 312 cagccca 7

<210> SEQ ID NO 313
<211> LENGTH: 7
<212> TYPE: RNA
<213> ORGANISM: Homo sapiens
<220> FEATURE:
<223> OTHER INFORMATION: 313: target regions in region 1+2+2-3 of homo sapiens numb exon 9

<400> SEQUENCE: 313 agcccau 7

<210> SEQ ID NO 314
<211> LENGTH: 7
<212> TYPE: RNA
<213> ORGANISM: Homo sapiens
<220> FEATURE:
<223> OTHER INFORMATION: 314: target regions in region 1+2+2-3 of homo sapiens numb exon 9

<400> SEQUENCE: 314 gcccaua 7

<210> SEQ ID NO 315
<211> LENGTH: 7
<212> TYPE: RNA
<213> ORGANISM: Homo sapiens
<220> FEATURE:
<223> OTHER INFORMATION: 315: target regions in region 1+2+2-3 of homo sapiens numb exon 9

<400> SEQUENCE: 315 cccauac 7

<210> SEQ ID NO 316
<211> LENGTH: 7
<212> TYPE: RNA
<213> ORGANISM: Homo sapiens
<220> FEATURE:
<223> OTHER INFORMATION: 316: target regions in region 1+2+2-3 of homo sapiens numb exon 9

<400> SEQUENCE: 316 ccauacu 7

<210> SEQ ID NO 317
<211> LENGTH: 13
<212> TYPE: RNA
<213> ORGANISM: Homo sapiens
<220> FEATURE:

<223> OTHER INFORMATION: 317: target regions in region 1+2+2-3 of homo sapiens numb exon 9

<400> SEQUENCE: 317
ugcuugcuaa gcc 13

<210> SEQ ID NO 318
<211> LENGTH: 13
<212> TYPE: RNA
<213> ORGANISM: Homo sapiens
<220> FEATURE:
<223> OTHER INFORMATION: 318: target regions in region 1+2+2-3 of homo sapiens numb exon 9

<400> SEQUENCE: 318
gcuugcuaag cca 13

<210> SEQ ID NO 319
<211> LENGTH: 13
<212> TYPE: RNA
<213> ORGANISM: Homo sapiens
<220> FEATURE:
<223> OTHER INFORMATION: 319: target regions in region 1+2+2-3 of homo sapiens numb exon 9

<400> SEQUENCE: 319
cuugcuaagc cag 13

<210> SEQ ID NO 320
<211> LENGTH: 13
<212> TYPE: RNA
<213> ORGANISM: Homo sapiens
<220> FEATURE:
<223> OTHER INFORMATION: 320: target regions in region 1+2+2-3 of homo sapiens numb exon 9

<400> SEQUENCE: 320
uugcuaagcc agc 13

<210> SEQ ID NO 321
<211> LENGTH: 13
<212> TYPE: RNA
<213> ORGANISM: Homo sapiens
<220> FEATURE:
<223> OTHER INFORMATION: 321: target regions in region 1+2+2-3 of homo sapiens numb exon 9

<400> SEQUENCE: 321
ugcuaagcca gcc 13

<210> SEQ ID NO 322
<211> LENGTH: 13
<212> TYPE: RNA
<213> ORGANISM: Homo sapiens
<220> FEATURE:
<223> OTHER INFORMATION: 322: target regions in region 1+2+2-3 of homo sapiens numb exon 9

<400> SEQUENCE: 322
gcuaagccag ccc 13

<210> SEQ ID NO 323
<211> LENGTH: 13
<212> TYPE: RNA
<213> ORGANISM: Homo sapiens
<220> FEATURE:
<223> OTHER INFORMATION: 323: target regions in region 1+2+2-3 of homo sapiens numb exon 9

<400> SEQUENCE: 323
cuaagccagc cca 13

<210> SEQ ID NO 324
<211> LENGTH: 13
<212> TYPE: RNA
<213> ORGANISM: Homo sapiens
<220> FEATURE:
<223> OTHER INFORMATION: 324: target regions in region 1+2+2-3 of homo
sapiens numb exon 9

<400> SEQUENCE: 324
uaagccagcc cau 13

<210> SEQ ID NO 325
<211> LENGTH: 13
<212> TYPE: RNA
<213> ORGANISM: Homo sapiens
<220> FEATURE:
<223> OTHER INFORMATION: 325: target regions in region 1+2+2-3 of homo
sapiens numb exon 9

<400> SEQUENCE: 325
aagccagccc aua 13

<210> SEQ ID NO 326
<211> LENGTH: 13
<212> TYPE: RNA
<213> ORGANISM: Homo sapiens
<220> FEATURE:
<223> OTHER INFORMATION: 326: target regions in region 1+2+2-3 of homo
sapiens numb exon 9

<400> SEQUENCE: 326
agccagccca uac 13

<210> SEQ ID NO 327
<211> LENGTH: 13
<212> TYPE: RNA
<213> ORGANISM: Homo sapiens
<220> FEATURE:
<223> OTHER INFORMATION: 327: target regions in region 1+2+2-3 of homo
sapiens numb exon 9

<400> SEQUENCE: 327
gccagcccau acu 13

<210> SEQ ID NO 328
<211> LENGTH: 21
<212> TYPE: RNA
<213> ORGANISM: Homo sapiens
<220> FEATURE:
<223> OTHER INFORMATION: 328: target regions in region 1+2+2-3 of homo
sapiens numb exon 9

<400> SEQUENCE: 328
cuuccaugug cuugcuaagc c 21

<210> SEQ ID NO 329
<211> LENGTH: 21
<212> TYPE: RNA
<213> ORGANISM: Homo sapiens
<220> FEATURE:
<223> OTHER INFORMATION: 329: target regions in region 1+2+2-3 of homo
sapiens numb exon 9

<400> SEQUENCE: 329
uuccaugugc uugcuaagcc a 21

<210> SEQ ID NO 330
<211> LENGTH: 21
<212> TYPE: RNA
<213> ORGANISM: Homo sapiens
<220> FEATURE:
<223> OTHER INFORMATION: 330: target regions in region 1+2+2-3 of homo sapiens numb exon 9

<400> SEQUENCE: 330
uccaugugcu ugcuaagcca g 21

<210> SEQ ID NO 331
<211> LENGTH: 21
<212> TYPE: RNA
<213> ORGANISM: Homo sapiens
<220> FEATURE:
<223> OTHER INFORMATION: 331: target regions in region 1+2+2-3 of homo sapiens numb exon 9

<400> SEQUENCE: 331
ccaugugcuu gcuaagccag c 21

<210> SEQ ID NO 332
<211> LENGTH: 21
<212> TYPE: RNA
<213> ORGANISM: Homo sapiens
<220> FEATURE:
<223> OTHER INFORMATION: 332: target regions in region 1+2+2-3 of homo sapiens numb exon 9

<400> SEQUENCE: 332
caugugcuug cuaagccagc c 21

<210> SEQ ID NO 333
<211> LENGTH: 21
<212> TYPE: RNA
<213> ORGANISM: Homo sapiens
<220> FEATURE:
<223> OTHER INFORMATION: 333: target regions in region 1+2+2-3 of homo sapiens numb exon 9

<400> SEQUENCE: 333
augugcuugc uaagccagcc c 21

<210> SEQ ID NO 334
<211> LENGTH: 21
<212> TYPE: RNA
<213> ORGANISM: Homo sapiens
<220> FEATURE:
<223> OTHER INFORMATION: 334: target regions in region 1+2+2-3 of homo sapiens numb exon 9

<400> SEQUENCE: 334
ugugcuugcu aagccagccc a 21

<210> SEQ ID NO 335
<211> LENGTH: 21
<212> TYPE: RNA
<213> ORGANISM: Homo sapiens
<220> FEATURE:
<223> OTHER INFORMATION: 335: target regions in region 1+2+2-3 of homo sapiens numb exon 9

<400> SEQUENCE: 335
gugcuugcua agccagccca u 21

<210> SEQ ID NO 336
<211> LENGTH: 21
<212> TYPE: RNA
<213> ORGANISM: Homo sapiens
<220> FEATURE:
<223> OTHER INFORMATION: 336: target regions in region 1+2+2-3 of homo sapiens numb exon 9

<400> SEQUENCE: 336
ugcuugcuaa gccagcccau a 21

<210> SEQ ID NO 337
<211> LENGTH: 21
<212> TYPE: RNA
<213> ORGANISM: Homo sapiens
<220> FEATURE:
<223> OTHER INFORMATION: 337: target regions in region 1+2+2-3 of homo sapiens numb exon 9

<400> SEQUENCE: 337
gcuugcuaag ccagcccaua c 21

<210> SEQ ID NO 338
<211> LENGTH: 21
<212> TYPE: RNA
<213> ORGANISM: Homo sapiens
<220> FEATURE:
<223> OTHER INFORMATION: 338: target regions in region 1+2+2-3 of homo sapiens numb exon 9

<400> SEQUENCE: 338
cuugcuaagc cagcccauac u 21

<210> SEQ ID NO 339
<211> LENGTH: 14
<212> TYPE: RNA
<213> ORGANISM: Homo sapiens
<220> FEATURE:
<223> OTHER INFORMATION: 339: Antisense oligonucleotide targeting Region 1 of Homo sapiens Numb exon 9 - 14 nt long, targeting second part of region defined by SEQ ID NO:44

<400> SEQUENCE: 339
aggcugaguc agug 14

<210> SEQ ID NO 340
<211> LENGTH: 14
<212> TYPE: RNA
<213> ORGANISM: Homo sapiens
<220> FEATURE:
<223> OTHER INFORMATION: 340: Antisense oligonucleotide targeting Region 1 of Homo sapiens Numb exon 9 - 14 nt long, targeting firstpart of region defined by SEQ ID NO:44

<400> SEQUENCE: 340
gucagugcca uuag 14

<210> SEQ ID NO 341
<211> LENGTH: 14
<212> TYPE: RNA
<213> ORGANISM: Homo sapiens
<220> FEATURE:
<223> OTHER INFORMATION: 341: Homo sapiens Numb exon 9 sequence targeted by antisense oligonucleotide of SEQ ID NO: 339

<400> SEQUENCE: 341
cacugacuca gccu 14

<210> SEQ ID NO 342
<211> LENGTH: 14
<212> TYPE: RNA
<213> ORGANISM: Homo sapiens
<220> FEATURE:
<223> OTHER INFORMATION: 342: Homo sapiens Numb exon 9 sequence targeted by antisense oligonucleotide of SEQ ID NO: 340

<400> SEQUENCE: 342
cuaauggcac ugac 14

<210> SEQ ID NO 343
<211> LENGTH: 14
<212> TYPE: RNA
<213> ORGANISM: Artificial Sequence
<220> FEATURE:
<223> OTHER INFORMATION: 343: Random oligonucleotide - 14 nt long

<400> SEQUENCE: 343
aaaccgcgcg uacg 14

<210> SEQ ID NO 344
<211> LENGTH: 7
<212> TYPE: RNA
<213> ORGANISM: Homo sapiens
<220> FEATURE:
<223> OTHER INFORMATION: 344: Antisense oligonucleotide targeting SEQ ID NO:59 in Region 1 of Homo sapiens Numb exon 9 - 7 nt long

<400> SEQUENCE: 344 aggcuga 7

<210> SEQ ID NO 345
<211> LENGTH: 7
<212> TYPE: RNA
<213> ORGANISM: Homo sapiens
<220> FEATURE:
<223> OTHER INFORMATION: 345: Antisense oligonucleotide targeting SEQ ID NO:56 in Region 1 of Homo sapiens Numb exon 9 - 7 nt long

<400> SEQUENCE: 345 cugaguc 7

<210> SEQ ID NO 346
<211> LENGTH: 7
<212> TYPE: RNA
<213> ORGANISM: Homo sapiens
<220> FEATURE:
<223> OTHER INFORMATION: 346: Antisense oligonucleotide targeting SEQ ID NO: 52 in Region 1 of Homo sapiens Numb exon 9 - 7 nt long

<400> SEQUENCE: 346 gucagug 7

<210> SEQ ID NO 347
<211> LENGTH: 7
<212> TYPE: RNA
<213> ORGANISM: Homo sapiens
<220> FEATURE:
<223> OTHER INFORMATION: 347: Antisense oligonucleotide targeting SEQ ID NO:49 in Region 1 of Homo sapiens Numb exon 9 - 7 nt long

<400> SEQUENCE: 347 agugcca 7

<210> SEQ ID NO 348
<211> LENGTH: 7
<212> TYPE: RNA
<213> ORGANISM: Homo sapiens
<220> FEATURE:
<223> OTHER INFORMATION: 348: Antisense oligonucleotide targeting SEQ ID NO: 45 in Region 1 of Homo sapiens Numb exon 9 - 7 nt long

<400> SEQUENCE: 348 ccauuag 7

<210> SEQ ID NO 349
<211> LENGTH: 21
<212> TYPE: RNA
<213> ORGANISM: Artificial Sequence
<220> FEATURE:
<223> OTHER INFORMATION: 349: Random oligonucleotide - 21 nt long

<400> SEQUENCE: 349
aaccgcgcgu acgaaaccgu c 21

<210> SEQ ID NO 350
<211> LENGTH: 21
<212> TYPE: RNA
<213> ORGANISM: Homo sapiens
<220> FEATURE:
<223> OTHER INFORMATION: 350: Antisense oligonucleotide targeting SEQ ID NO: 117 in Region 1+2+2-3 of Homo sapiens Numb exon 9 - 21 nt long

<400> SEQUENCE: 350
caagcacaug gaaggcugag u 21

<210> SEQ ID NO 351
<211> LENGTH: 21
<212> TYPE: RNA
<213> ORGANISM: Homo sapiens
<220> FEATURE:
<223> OTHER INFORMATION: 351: Antisense oligonucleotide targeting SEQ ID NO: 121 in Region 1+2+2-3 of Homo sapiens Numb exon 9 - 21 nt long

<400> SEQUENCE: 351
uuagcaagca cauggaaggc u 21

<210> SEQ ID NO 352
<211> LENGTH: 21
<212> TYPE: RNA
<213> ORGANISM: Homo sapiens
<220> FEATURE:
<223> OTHER INFORMATION: 352: Antisense oligonucleotide targeting SEQ ID NO: 331 in Region 1+2+2-3 of Homo sapiens Numb exon 9 - 21 nt long

<400> SEQUENCE: 352
gcuggcuuag caagcacaug g 21

<210> SEQ ID NO 353
<211> LENGTH: 21
<212> TYPE: RNA
<213> ORGANISM: Homo sapiens
<220> FEATURE:
<223> OTHER INFORMATION: 353: Antisense oligonucleotide targeting SEQ ID NO: in Region 2+3 of Homo sapiens Numb exon 9 - 21 nt long

<400> SEQUENCE: 353
gagcaguaug ggcuggcuua g 21

<210> SEQ ID NO 354
<211> LENGTH: 21
<212> TYPE: RNA
<213> ORGANISM: Homo sapiens
<220> FEATURE:
<223> OTHER INFORMATION: 354: Region of Homo sapiens Numb exon 9
targeted by SEQ ID NO:353

<400> SEQUENCE: 354
cuaagccagc ccauacugcu c 21

<210> SEQ ID NO 355
<211> LENGTH: 21
<212> TYPE: RNA
<213> ORGANISM: Homo sapiens
<220> FEATURE:
<223> OTHER INFORMATION: 355: Antisense oligonucleotide targeting a in
Region 2+3 of Homo sapiens Numb exon 9 - 21 nt long

<400> SEQUENCE: 355 gcuagagcagu augggcugg c 21

<210> SEQ ID NO 356
<211> LENGTH: 21
<212> TYPE: RNA
<213> ORGANISM: Homo sapiens
<220> FEATURE:
<223> OTHER INFORMATION: 356: Region of Homo sapiens Numb exon 9
targeted by SEQ ID NO:355

<400> SEQUENCE: 356
gccagcccau acugcucuag c 21

<210> SEQ ID NO 357
<211> LENGTH: 21
<212> TYPE: RNA
<213> ORGANISM: Artificial Sequence
<220> FEATURE:
<223> OTHER INFORMATION: 357: Random oligonucleotide - 21 nt long

<400> SEQUENCE: 357
ugauucgugc ggcgcguaua u 21

<210> SEQ ID NO 358
<211> LENGTH: 21
<212> TYPE: DNA
<213> ORGANISM: Homo sapiens
<220> FEATURE:
<223> OTHER INFORMATION: NUMB exon 9 target sequence SUPERLONG

<400> SEQUENCE: 358
ctaatggcac tgactcagcc t 21

<210> SEQ ID NO 359
<211> LENGTH: 14
<212> TYPE: DNA
<213> ORGANISM: Homo sapiens
<220> FEATURE:
<223> OTHER INFORMATION: NUMB exon 9 target sequence LONG2

<400> SEQUENCE: 359
ctaatggcac tgac 14

<210> SEQ ID NO 360
<211> LENGTH: 14
<212> TYPE: DNA

<213> ORGANISM: Homo sapiens
<220> FEATURE:
<223> OTHER INFORMATION: NUMB exon 9 target sequence LONG1

<400> SEQUENCE: 360
cactgactca gcct 14

<210> SEQ ID NO 361
<211> LENGTH: 7
<212> TYPE: DNA
<213> ORGANISM: Homo sapiens
<220> FEATURE:
<223> OTHER INFORMATION: NUMB exon 9 target sequence LNA2-3

<400> SEQUENCE: 361 tggcact 7

<210> SEQ ID NO 362
<211> LENGTH: 7
<212> TYPE: DNA
<213> ORGANISM: Homo sapiens
<220> FEATURE:
<223> OTHER INFORMATION: NUMB exon 9 target sequence LNA1-2

<400> SEQUENCE: 362 gactcag 7

<210> SEQ ID NO 363
<211> LENGTH: 7
<212> TYPE: DNA
<213> ORGANISM: Homo sapiens
<220> FEATURE:
<223> OTHER INFORMATION: NUMB exon 9 target sequence LNA3

<400> SEQUENCE: 363 ctaatgg 7

<210> SEQ ID NO 364
<211> LENGTH: 7
<212> TYPE: DNA
<213> ORGANISM: Homo sapiens
<220> FEATURE:
<223> OTHER INFORMATION: NUMB exon 9 target sequence LNA2

<400> SEQUENCE: 364 cactgac 7

<210> SEQ ID NO 365
<211> LENGTH: 7
<212> TYPE: DNA
<213> ORGANISM: Homo sapiens
<220> FEATURE:
<223> OTHER INFORMATION: NUMB exon 9 target sequence LNA1

<400> SEQUENCE: 365 tcagcct 7

<210> SEQ ID NO 366
<211> LENGTH: 19
<212> TYPE: DNA
<213> ORGANISM: Homo sapiens
<220> FEATURE:
<223> OTHER INFORMATION: 3'SS

<400> SEQUENCE: 366
ctgctcccgt tgtagctaa 19

-continued

<210> SEQ ID NO 367
<211> LENGTH: 21
<212> TYPE: DNA
<213> ORGANISM: Homo sapiens
<220> FEATURE:
<223> OTHER INFORMATION: NUMB exon 9 target sequence AON3

<400> SEQUENCE: 367
cagcccatac tgctctagca c 21

<210> SEQ ID NO 368
<211> LENGTH: 86
<212> TYPE: DNA
<213> ORGANISM: Homo sapiens
<220> FEATURE:
<223> OTHER INFORMATION: exon 9 3'

<400> SEQUENCE: 368
ctgctcccgt tgtagctaat ggcactgact cagccttcca tgtgcttgct aagccagccc 60
atactgctct agcacccgta gcaatg 86

<210> SEQ ID NO 369
<211> LENGTH: 21
<212> TYPE: DNA
<213> ORGANISM: Homo sapiens
<220> FEATURE:
<223> OTHER INFORMATION: NUMB exon 9 target sequence AON1

<400> SEQUENCE: 369
ctaatggcac tgactcagcc t 21

<210> SEQ ID NO 370
<211> LENGTH: 21
<212> TYPE: DNA
<213> ORGANISM: Homo sapiens
<220> FEATURE:
<223> OTHER INFORMATION: NUMB exon 9 target sequence AON2-3

<400> SEQUENCE: 370
cttgctaagc cagcccatac t 21

<210> SEQ ID NO 371
<211> LENGTH: 21
<212> TYPE: DNA
<213> ORGANISM: Homo sapiens
<220> FEATURE:
<223> OTHER INFORMATION: NUMB exon 9 target sequence AON2

<400> SEQUENCE: 371
ccttccatgt gcttgctaag c 21

<210> SEQ ID NO 372
<211> LENGTH: 21
<212> TYPE: DNA
<213> ORGANISM: Homo sapiens
<220> FEATURE:
<223> OTHER INFORMATION: NUMB exon 9 target sequence AON1-2

<400> SEQUENCE: 372
actgactcag ccttccatgt g 21

ANTISENSE OLIGONUCLEOTIDES AND USES THEREOF

CROSS-REFERENCE TO RELATED APPLICATIONS

This application is a § 371 U.S. National Stage Application of International Application No. PCT/EP2019/056889 filed Mar. 19, 2019 and claims priority to EP 18162571.6 filed Mar. 19, 2018, the entire disclosures of which are incorporated herein by reference.

FIELD OF THE INVENTION

This invention relates to antisense nucleotides that promote the exclusion of NUMB exon 9. In particular, the invention relates to oligonucleotides comprising a sequence that is complementary to a target region of a NUMB transcript, the target region being comprised in exon 9. The oligonucleotides of the invention are particularly useful in the treatment of proliferative diseases.

SEQUENCE LISTING

Applicant incorporates by reference a CRF sequence listing submitted herewith having file name Sequence List FCD0001PA.txt (77 KB), created on Mar. 19, 2019. The nucleic acid and/or amino acid sequences listed in the accompanying sequence listing are shown using standard abbreviations as defined in 37 C.F.R. 1.822.

BACKGROUND OF THE INVENTION

Alternative splicing is a major regulatory mechanism in eukaryotic gene expression, and its alterations have been linked with various diseases. For example, increased inclusion of a specific exon (exon 9) within the Open Reading Frame of a protein called NUMB has been reported as one of the most common splicing alterations in lung cancer (Misquitta-Ali et al. 2011; Sebestyén et al., 2015). Increased NUMB exon 9 inclusion has further been shown to increase the proliferative capacity of cancer cells in vitro (Bechara et al., 2013). The NUMB protein is known to play a role in regulation of at least the Notch pathway: isoforms of NUMB that exclude exon 9 act as repressors of the pathway and of cell proliferation, whereas isoforms of NUMB including exon 9 correlate with reduced NUMB protein levels and activation of the NOTCH pathway (Misquitta-Ali et al., 2011; Westhoff et al., 2009).

Because of the known correlation between NUMB alternative splicing of exon 9 and cell proliferation, as well as data indicating that increased NUMB exon 9 inclusion is amongst the most frequent tumour-associated alternative splicing changes that have been observed in lung cancer, the alternative splicing of exon 9 of NUMB represents a potential target for therapy. However, although some studies of alternative splicing have been conducted (see Bechara et al., 2013), the mechanisms involved are poorly understood and there is still a need for new and more effective ways of promoting the skipping of exon 9 in the NUMB pre-mRNA splicing process.

One potential strategy for regulating alternative splicing is the use of antisense oligonucleotides (AONs). AONs are short synthetic nucleotides which can bind to a complementary target sequence. Therapies based on AONs have been developed and an AON that targets an intronic splicing enhancer site of the pre-mRNA corresponding to the protein SMN2 (resulting in increased inclusion of exon 7), has been approved by the FDA and the EMA for the treatment of spinal muscular atrophy (Hua et al., 2010; Hua et al., 2011). However, efficient regulation of exon 9 inclusion/exclusion in NUMB has not been achieved using AONs or other methods.

The present invention seeks to provide compounds that can efficiently regulate NUMB alternative splicing.

SUMMARY OF THE INVENTION

In general terms, the present invention provides new compounds comprising oligonucleotides capable of regulating the alternative splicing of exon 9 of NUMB.

In one aspect, therefore, the invention provides an antisense oligonucleotide for reducing inclusion of NUMB exon 9 in a population of mature NUMB transcripts, the antisense oligonucleotide comprising a sequence of at least 7 nucleotides that is complementary to a target region within exon 9 (SEQ ID NO: 2 or homologues thereof) of a NUMB transcript.

In a second aspect, the invention provides an antisense oligonucleotide for reducing inclusion of NUMB exon 9 in a population of NUMB mRNAs, the antisense oligonucleotide comprising a sequence of at least 7 nucleotides that is complementary to a target region within exon 9 (SEQ ID NO: 2 or homologues thereof) of a NUMB pre-mRNA.

According to a third aspect, an antisense oligonucleotide is disclosed comprising a sequence of at least 7 nucleotides that is complementary to a target region of a NUMB transcript, wherein the target region comprises at least 7 nucleotides and is comprised in exon 9 (SEQ ID NO: 2) or homologues thereof, and wherein, in use, the oligonucleotide reduces inclusion of exon 9 in the mature NUMB transcript.

According to a fourth aspect, there is provided an oligonucleotide comprising 7 consecutive nucleotides of SEQ ID NO: 12, 22 or 24, wherein the oligonucleotide binds to a target region of a NUMB transcript which is comprised within NUMB exon 9, and wherein, in use, the oligonucleotide reduces inclusion of exon 9 in the mature NUMB transcript.

In embodiments of any aspect, the antisense oligonucleotide comprises a sequence selected from SEQ ID NO: 12, 13, 15-17 and 19-24, or homologues thereof.

In embodiments, the target region is comprised within the sequence of SEQ ID NO: 45-77, 306-316, 124-159 or 212-247 In embodiments, the target region is comprised within the sequence of SEQ ID NO: 78-104, 317-327, 160-189, or 248-277. In embodiments, the target region is comprised within the sequence of SEQ ID NO: 105-123, 328-338, 190-211 or 278-299.

In embodiments, the target region consists of the sequence of SEQ ID NO: 45-77, 306-316, 124-159 or 212-247. In embodiments, the target region consists of the sequence of SEQ ID NO: 78-104, 317-327, 160-189, or 248-277. In embodiments, the target region consists of the sequence of SEQ ID NO: 105-123, 328-338, 190-211 or 278-299.

In embodiments, the target region is comprised within the sequence CUAAUGGCACUGACUCAGCCUUCCAUGUGCUUGCUAAGC (SEQ ID NO: 9), CUAAUGGCACUGACUCAGCCUUCCAUGUGCUUGCUAAGCCAGCCCAUACU (SEQ ID NO:305), CCGUAGCAAUGCCUGUGCGUGAAACCAACCCUUGGGCCCAUG (SEQ ID NO: 10), or CCCCUGAUGCUGCUAACAAGGAAAUUGCAGCCACAUGUUCGG (SEQ ID NO: 11), or homologues thereof. In some such embodiments, the oligonucleotide is fully complementary to a polynucleotide sequence comprised in SEQ ID NO: 9, SEQ ID NO: 305, SEQ ID NO: 10, or SEQ ID NO: 11.

In embodiments, the target region is comprised within the sequence CUAAUGGCACUGACUCAGCCU (SEQ.ID NO: 44), CCUGUGCGUGAAACCAACCCU (SEQ ID NO: 31), or GCUAACAAGGAAAUUGCAGCC (SEQ ID NO: 32), or homologues thereof. In some such embodiments, the oligonucleotide is fully complementary to a sequence comprised in SEQ ID NO: 44, SEQ ID NO: 31, or SEQ ID NO: 32. In some embodiments, the oligonucleotide is fully complementary to a polynucleotide sequence comprised in SEQ ID NO: 44, SEQ ID NO: 31, or SEQ ID NO: 32.

In embodiments of any aspect of the invention, the antisense oligonucleotide essentially consists of a nucleotide sequence complementary to a contiguous nucleotide sequence of a NUMB transcript.

In embodiments of any aspect of the invention, the antisense oligonucleotide comprises a nucleotide sequence that is complementary to a target region comprising at least 13 nucleotides, at least 15 nucleotides, at least 18 nucleotides or at least 21 nucleotides of NUMB exon 9.

In embodiments of any aspect of the invention, the antisense oligonucleotide is between 7 and 31 nucleotides long. In embodiments, the antisense oligonucleotide is between 15 and 31 nucleotides long, between 18 and 31 nucleotides long, between 21 and 31 nucleotides long. In embodiments, the oligonucleotide is between 25 and 31 nucleotides long.

In embodiments of any aspect of the invention, the antisense oligonucleotide comprises a nucleotide sequence that is complementary to a target region of between 7 and 31 nucleotides, between 15 and 31 nucleotides, between 18 and 31 nucleotides, between 21 and 31 nucleotides, between 7 and 25 nucleotides, between 15 and 25 nucleotides, between 18 and 25 nucleotides, or between 21 and 25 nucleotides.

In embodiments, the antisense oligonucleotide is between 7 and 31 nucleotides long, between 15 and 31 nucleotides long, between 18 and 31 nucleotides long, between 21 and 31 nucleotides long, between 7 and 25 nucleotides long, between 15 and 25 nucleotides long, between 18 and 25 nucleotides long, or between 21 and 25 nucleotides long. In any of the embodiments of the invention, the oligonucleotide may be an RNA or modified RNA molecule, a DNA or modified DNA molecule, or a mixture of native or modified RNA and native or modified RNA. One or more (e.g. 1, 2, 3, 4, 5, 6 or more) nucleotides of the antisense oligonucleotide of the invention may be modified. For example, the oligonucleotide may comprise a locked nucleic acid, a 2'-O-methyl phosphorothioate ribonucleic acid, a 2'-O-methoxyethyl-modified phosphorothioate ribonucleic acid, and/or one or more methylated cytosine residues.

In embodiments, the oligonucleotide is between 7 and 15 nucleotides long, and the oligonucleotide is a locked nucleic acid.

In embodiments, the oligonucleotide is between 18 and 25 nucleotides long, and the oligonucleotide is a 2'-O-methyl phosphorothioate ribonucleic acid.

In embodiments, the oligonucleotide is between 18 and 25 nucleotides long, and the oligonucleotide is a 2'-O-methoxyethyl-modified phosphorothioate ribonucleic acid. In embodiments, the oligonucleotide is between 18 and 25 nucleotides long, and the oligonucleotide is a 2'-O-methyl-modified phosphorothioate ribonucleic acid.

In some embodiments, at least one cytosine residue within the oligonucleotide is methylated. In embodiments, all cytosine residues within the oligonucleotide are methylated.

In embodiments, the oligonucleotide does not comprise a sequence that is complementary to the 5' and/or 3' exon-intron junction of exon 9. In embodiments, the oligonucleotide is fully complementary to a polynucleotide sequence within exon 9 of a NUMB transcript.

In embodiments, the oligonucleotide comprises a sequence selected from: AGGCUGA (SEQ ID NO: 36), GUCAGUG (SEQ ID NO: 37), CCAUUAG (SEQ ID NO: 38), CUGAGUC (SEQ ID NO: 39), or AGUGCCA (SEQ ID NO: 40).

Suitably, the oligonucleotide may comprise a sequence selected from: AGGCUGAGUCAGUG (SEQ ID NO: 41), or GUCAGUGCCAUUAG (SEQ ID NO: 42).

In embodiments, the oligonucleotide comprises a sequence selected from: AGGCTGAGTCAGTGCCATTAG (SEQ ID NO: 43) or AGGCUGAGUCAGUGCCAUUAG (SEQ ID NO: 12).

In embodiments, the oligonucleotide comprises a sequence selected from: AGGCUGA (SEQ ID NO: 36), GUCAGUG (SEQ ID NO: 37), CCAUUAG (SEQ ID NO: 38), CUGAGUC (SEQ ID NO: 39) or AGUGCCA (SEQ ID NO: 40). In some embodiments, the oligonucleotide consists of a sequence selected from: AGGCUGA (SEQ ID NO: 36), GUCAGUG (SEQ ID NO: 37), CCAUUAG (SEQ ID NO: 38), CUGAGUC (SEQ ID NO: 39) or AGUGCCA (SEQ ID NO: 40).

In embodiments, the oligonucleotide comprises a sequence selected from: AGGCUGAGUCAGUG (SEQ ID NO: 41), or GUCAGUGCCAUUAG (SEQ ID NO: 42). Suitably, the oligonucleotide may consist of a sequence selected from: AGGCUGAGUCAGUG (SEQ ID NO: 41), or GUCAGUGCCAUUAG (SEQ ID NO: 42).

In embodiments, the oligonucleotide comprises a sequence selected from: AGGCTGAGTCAGTGCCATTAG or AGGCUGAGUCAGUGCCAUUAG (SEQ ID NO: 12). Suitably, the oligonucleotide may consist of a sequence selected from: AGGCTGAGTCAGTGCCATTAG or AGGCUGAGUCAGUGCCAUUAG (SEQ ID NO: 12).

The antisense oligonucleotide of any of the embodiments of the invention may be for use as a medicament.

Suitably, the antisense oligonucleotide may be for use in the treatment of a disease or condition associated with elevated levels of NUMB exon 9 inclusion in mature NUMB transcripts. In embodiments, the antisense oligonucleotide may be for use in the treatment of a disease or condition associated with elevated levels of NUMB exon 9 inclusion in mature NUMB transcripts compared to the level of NUMB exon 9 inclusion in a healthy matched tissue.

In embodiments, the antisense oligonucleotide of the invention may be for use in the treatment of a proliferative disease, such as a tumour or a cancer. In some such embodiments, the proliferative disease is a disease in which the numb protein acts as an antitumor agent.

In embodiments, the disease or condition is a proliferative disease in which the activation of the Notch pathway has a pro-proliferative role. In embodiments, the disease or condition is selected from lung adenocarcinoma, lung squamous-cell carcinoma, prostate cancer, cervical cancer, breast cancer, pancreatic cancer, hepatocacinoma, osteosarcoma, neuroblastoma or colon cancer. In embodiments, the disease or condition is lung adenocarcinoma, lung squamous-cell carcinoma, cervical cancer, breast cancer or colon cancer. In embodiments, the disease or condition is selected from lung adenocarcinoma, lung squamous-cell carcinoma, cervical cancer, breast cancer, pancreatic cancer, prostate cancer, hepatocacinoma, or colon cancer.

In embodiments, the antisense oligonucleotide is for use in a method for the treatment of a subject in need thereof, wherein the method comprises administering the oligonucleotide or a composition comprising the oligonucleotide to the subject.

Suitably, the method may further comprise testing a tissue sample obtained from the subject for elevated levels of NUMB exon 9 inclusion compared to a healthy control.

In embodiments, the subject is human.

In embodiments, the subject has a cancer or tumour and the method comprises delivering the oligonucleotide to the site of the cancer or the tumour. In some such embodiments, the subject has lung cancer and the method comprises delivering the oligonucleotide through the respiratory system.

In embodiments, the delivery through the respiratory system is performed intranasally, or via intratracheal administration. In embodiments, the delivery through the respiratory system is performed by nebulisation or via any other direct lung delivery system.

In embodiments, the method comprises injecting a composition comprising the oligonucleotide intravenously.

The invention is also directed, in another aspect, to a method of treating a proliferative disease, the method comprising administering the antisense oligonucleotide of any of the preceding aspects to a subject in need thereof. In embodiments, the subject is human.

In embodiments, the subject has a cancer or tumour. Suitably, the method may further comprise delivering the oligonucleotide to the site of the cancer/tumour.

In embodiments, the subject has lung cancer and the method comprises delivering the oligonucleotide through the respiratory system. In embodiments, the method comprises delivering the oligonucleotide through the respiratory system intranasally or intratracheally. In embodiments, the method comprises delivering the oligonucleotide by nebulisation.

In embodiments, the method comprises injecting a composition comprising the oligonucleotide intravenously.

In embodiments, the method further comprises testing the patient for elevated levels of NUMB exon 9 inclusion compared to a healthy control.

The invention, in another aspect, also encompasses a method of reducing NUMB exon 9 inclusion in a subject in need thereof, the method comprising administering the oligonucleotide of any of the first to fourth aspects to the subject.

In yet another aspect, the invention encompasses a method of reducing NUMB exon 9 inclusion in a population of NUMB mature mRNAs, the method comprising contacting a population of NUMB pre-mRNA with an antisense oligonucleotide according to any of the first to fourth aspects.

According to a further aspect, the invention provides a pharmaceutical composition comprising one or more antisense oligonucleotides according to any of the first to fourth aspects.

In embodiments, the pharmaceutical composition further comprises one or more excipients.

It will be appreciated that any features of one aspect or embodiment of the invention may be combined with any combination of features in any other aspect or embodiment of the invention, unless otherwise stated, and such combinations are envisaged and are intended to be directly and unambiguously disclosed herein, and to fall within the scope of the present invention.

BRIEF DESCRIPTION OF THE DRAWINGS

The invention is further illustrated by way of the accompanying drawings in which:

FIG. 3A shows the relevant region of the polyacrylamide gels following electrophoretic separation of the PCR amplified products, and FIG. 3B shows the percent splice in (PSI) that correspond to the data;

FIG. 7A illustrates Western blot results documenting increased expression of QKI; and FIG. 7B shows PSI (percent of spliced in—fraction of exon inclusion) values of NUMB exon 9 from a NUMB minigene in which the binding site of QKI in the target sequence of AON1 has been modified;

DETAILED DESCRIPTION OF THE INVENTION

Figure 1:
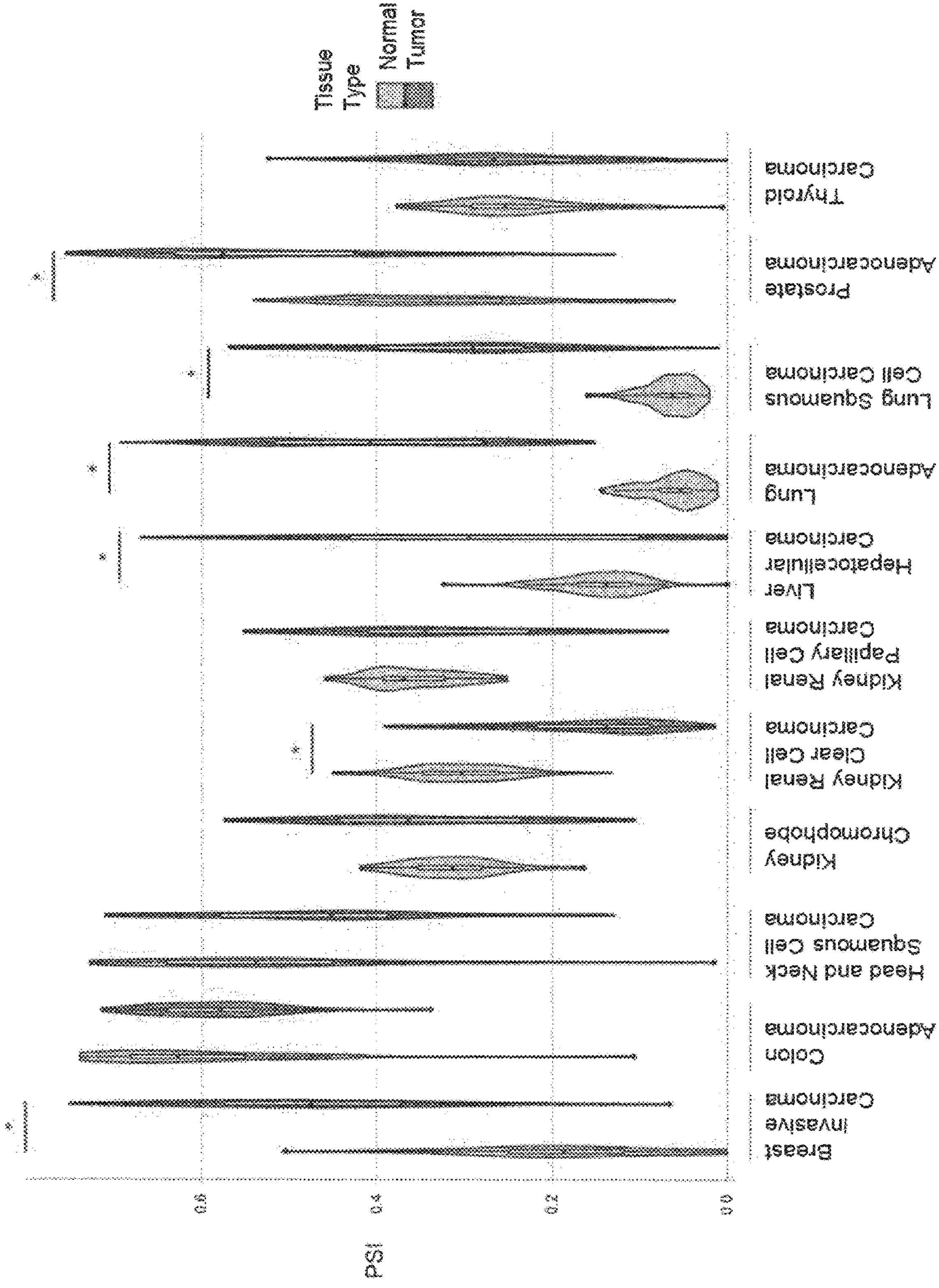
FIG. 1 shows the results of an investigation of the levels of NUMB exon 9 inclusion in different tumors compared to matched healthy tissues.

All references cited herein are incorporated by reference in their entirety. Unless otherwise defined, all technical and scientific terms used herein have the same meaning as commonly understood by one of ordinary skill in the art to which this invention belongs.

Unless otherwise indicated, the practice of the present invention employs conventional techniques in chemistry and chemical methods, biochemistry, pharmaceutical formulation, and delivery and treatment regimes for patients, which are within the capabilities of a person of ordinary skill in the art. Such techniques are also described in the literature cited herein, each of which is herein incorporated by reference.

Prior to setting forth the detailed description of the invention, a number of definitions are provided that will assist in the understanding of the invention.

The term 'antisense oligonucleotide' (AON) refers to a short oligonucleotide or modified oligonucleotide which is antisense to and binds to (i.e. hybridises to) a target region of a polynucleotide, such as a gene transcript, pre-mRNA, mRNA or RNA fragment. According to the invention, the target region for an AON is preferably in a pre-mRNA, i.e. the AON binds to a target region on a transcript before the splicing process takes place. The AONs of the invention may comprise native or modified RNA, DNA, or mixtures thereof. Any modification may be naturally occurring or non-naturally occurring. Any references to an AON sequence provided as an RNA sequence is intended to also encompass the equivalent DNA sequence. In particular, any sequence comprising U bases is intended to refer equally to the corresponding sequence in which T bases are present in place of one or more (e.g. all) of the Us. In embodiments, the oligonucleotides according to the invention may comprise nucleotides comprising inosine. In particular, any AON sequence disclosed herein is intended to encompass nucleotide sequences where one or more of the T, G or As are replaced with I, as far as this is compatible with the function of the AON. The AONs according to the invention have an effect on the regulation of alternative splicing. In particular, the AONs according to the invention advantageously promote the skipping of a specific exon, resulting in a decreased inclusion of the exon in the mature transcript resulting from splicing of the pre-mRNA. As the skilled person would understand, the range of lengths of AONs that are suitable will depend on the desired specificity (where longer AONs are expected to bind to their target sequence with higher specificity) and efficacy of the in vivo delivery (where longer AONs are expected to be more difficult to efficiently deliver to the target cells). The AON's of the invention preferably have a length of at most 35 nucleotides, at most 25 nucleotides, at most 24 nucleotides, at most 21 nucleotides, or at most 18 nucleotides. An oligonucleotide as used herein may have a length of at least 7 nucleotides, at least 10 nucleotides, at least 13 nucleotides, at least 14 nucleotides, or at least 17 nucleotides.

As known in the art, the AONs of the invention may be chemically modified, for example to increase their stability, reduce their immunogenicity, increase their binding affinity to a target sequence, reduce their non-specific binding to unintended targets (see e.g. Mou & Gray, 2002) and/or enhance their delivery, etc. Chemical modification of an oligonucleotide refers to a chemical difference compared to the native form of ribo or deoxyribonucelotides (i.e. nucleotides comprising the naturally occurring nucleobases of RNA or DNA, including (deoxy)adenosine, (deoxy)guanosine, (deoxy)thymidine, (deoxy)cytidine, 5-methyl (deoxy) cytidine and uridine; and a phosphate linking group). Chemical modifications may be applied to the sugar moiety of a nucleoside, the nucleobase moiety of a nucleoside and/or the phosphate backbone. Examples of modified chemically modified nucleotides or analogues that may be used in the present invention include locked nucleic acids, the use of a phosphorothioate backbone, 2'-O-methylated nucleotides, 2'-O-methoxyethyl modified (2'MOE) nucleotides, methylated cytosine, constrained ethyl (cET) nucleic acids, bridged nucleic acids (BNAs), phosphorodiamidate morpholino oligomers (PMOs), peptide nucleic aids (PNAs), cyclohexene nucleic acids (CeNAs), tricycle-DNA (tcDNA), N3'-P5' phosphoroamidates (NPs), 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-fluoro-2'-deoxythymidine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, 2'-O-methylinosine-5'-triphosphate, 2'-O-methyl-2-aminoadenosine-5'-triphosphate, 2'-O-methylpseudouridine-5'-triphosphate, 2'-O-methyl-5-methyluridine-5'-triphosphate etc. Chemical modifications may be applied to one or more nucleotides of an oligonucleotide and, as such, reference to a 'modified (antisense) oligonucleotide' or 'modified AON' relates to oligonucleotides comprising at least one modified nucleotide. In embodiments, 2'-O modified nucleotides may be used to surround (i.e. flank) a central sequence, thereby forming a gapmer, as known in the art. Such compounds may be particularly resistant to nuclease degradation. As the skilled person would understand, multiple modifications may be present on the same nucleotide. Further, different modifications may be present on different nucleotides of the same oligonucleotide. As known in the art, the optimal length of an AON may depend on the modifications (or absence thereof) that may be present on the AON.

A 'locked nucleic acid' (LNA) as used herein refers to a ribonucleic acid where at least one of the nucleotides has the ribose moiety modified with a methylene bridge connecting the 2' oxygen and the 4' carbon. Without wishing to be bound by theory, it is believed that this locks the ribose ring in an ideal conformation for Watson-Crick base-pairing, making the pairing of a locked nucleotide with a complementary nucleotide strand more rapid and more stable. A locked nucleic acid may comprise a mixture of locked nucleotides and ribonucleic acids. In embodiments, all of the nucleotides of the oligonucleotides according to the invention are locked nucleotides. In embodiments where the AON is an LNA, the length of the AON may be between 7 and 21 nucleotides. In some embodiments, the length of the AON may be between 7 and 17 nucleotides. In some such embodiments, the length of the AON is 13 or 14 nucleotides.

As used herein a 'phosphorothioate (ribo)nucleic acid' (or oligonucleotide phosphorothioate) refers to a modified (ribo)nucleic acid in which one of the oxygen atoms in the phosphate moiety is replaced by sulphur, wherein the oxygen that is replaced by sulphur is at a non-bridging position. Without wishing to be bound by theory, it is believed that because phosphorothioate (ribo)nucleic acids are non-natural analogs of nucleic acids, oligonucleotide phosphorothioates are substantially more stable with respect to hydrolysis by nucleases, the class of enzymes that destroy nucleic acids by breaking the bridging P—O bond of the phosphodiester moiety. An oligonucleotide phosphorothioate may comprise a mixture of modified and unmodified nucleotides. In embodiments, the whole backbone of the oligonucleotide of the invention is modified, and each nucleotide may be a phosphorothioate nucleotide.

AONs according to the invention may comprise 2'-O-methylated ribonucleotides. 2'-O-methylated ribonucleotides comprise a methyl group added to the 2' hydroxyl of the ribose moiety of the nucleotide, producing a methoxy group. In embodiments, AONs according to the invention may comprise one or more 2'-O-methylated ribonucleotides. In embodiments, all of the nucleotides of the AON may be 2'-O-methylated ribonucleotides.

AONs according to the invention may comprise 2'-O-methoxyethyl ribonucleotides. 2'-O-methoxyethyl ribonucleotides comprise a methoxyethyl group ($—CH_2CH_2OCH_3$) added to the 2' hydroxyl of the ribose moiety of the nucleotide. In embodiments, AONs according to the invention may comprise one or more 2'-O-methoxyethyl ribonucleotides. In embodiments, all of the nucleotides of the AON may be 2'-O-methoxyethyl ribonucleotides.

In some embodiments the AONs according to the invention may comprise a mixture of one or more ribonucleotides modified with a methyl group (e.g. 2'-O-methylated ribonucleotides) and one or more ribonucleotides modified with a methoxyethyl group (e.g. 2'-O-methoxylethyl ribonucleotides).

In embodiments, the oligonucleotides may have the same or similar chemical modifications as the AON therapy Spinraza (Nusinersen, RNA, (2'-O-(2-METHOXYETHYL))(P-THIO)(M5U-C-A-C-M5U-M5U-M5U-C-A-M5UA-A-M5 U-G-C-M5U-G-G), CAS1258984-36-9).

In embodiments, the oligonucleotides according to the invention may comprise one or more conjugate groups, for example, in order to modify the properties of the compound, such as the pharmacodynamics, distribution, stability, binding and/or absorption etc. of the compound, as known in the art. In embodiments, the one or more conjugate groups may comprise a ligand that targets the compound, for example to a specific type of cells. Thus, in embodiments, the invention encompasses compounds comprising one or more oligonucleotides according to the invention fused to another chemical entity, such as a pharmaceutical drug. The conjugated entity (or group) may comprise nucleotides or may be a non-nucleotide based molecule. In embodiments, the conjugated entity may comprise a splicing modifying drug. Examples of splicing modifying drugs are provided in Vigevani, L., & Valcárcel, J. (2012). In embodiments, the drug is selected from the group comprising sudemycins, spliceostatin, pladienolides and meayamycins, or derivatives thereof.

References to a reduction in exon 9 inclusion or promotion of exon 9 skipping throughout this disclosure are equivalent and refer to a reduced percentage of NUMB transcript spliced to include exon 9 (expressed as 'percent spliced in'/'percentage splicing index' PSI) compared to a control condition. Conversely, references to an increase in exon 9 inclusion, or inhibition/reduction of exon 9 skipping, refer to an increased percent spliced in (PSI) of exon 9 compared to a control condition. PSI may be obtained using methods known in the art, including reverse transcription—polymerase chain reaction (RT-PCR), mRNA sequencing (RNA-seq), etc.

The inventors have surprisingly discovered that NUMB exon 9 inclusion can be efficiently down-regulated by targeting specific regions within exon 9 of NUMB with AONs. Specific regions within exon 9 of NUMB were identified as targets for AONs, and the AONs of the invention beneficially result in reduced inclusion of exon 9 in NUMB transcripts. Further, the inventors have surprisingly discovered that targeting specific regions within exon 9 of NUMB with AONs can result in more efficient down-regulation of exon 9 inclusion than is possible by targeting the splice sites of exon 9.

As used herein, references to exon 9 of NUMB relate to positions 1417 to 1560 (SEQ ID NO: 2) of Human Numb mRNA transcript variant 1 (NM_001005743) or equivalent positions in other transcript variants encoded by the NUMB gene (Entrez Gene ID 8650), or homologues thereof (such as the mouse homolog of SEQ ID NO: 1 (positions 1115 to 1261 of NM_001136075.2 —*Mus Musculus* Numb mRNA transcript variant 1).

The inventors have discovered that targeting specific regions within exon 9 of the NUMB transcript with AONs resulted in a significant decrease in the inclusion of exon 9 in mature transcripts of NUMB. In particular, AONs according to the invention may comprise a sequence that is complementary to a target sequence in specific regions within NUMB exon 9, the target sequence being at least 7 nucleotides long and being located within the regions defined by SEQ ID NO: 9, 305, 10 or 11; or homologues thereof. In other words, the AONs according to the invention may comprise a sequence that is complementary to at least 7 contiguous nucleotides located within one of the regions underlined in the sequences below, or homologues thereof.

Human NUMB exon 9 (positions 1417...1560 of NM_001005743; SEQ ID NO: 2):

ctaatggcac tgactcagcc ttccatgtgc ttgctaagcc agcccatact gctctagcac ccgtagcaat gcctgtgcgt gaaaccaacc cttgggccca tg cccctgat gctgctaacaa ggaaattgca gccacatgtt cgg

Mouse NUMB exon 9 (positions 1115 to 1261 of NM_001136075.2; SEQ ID NO: 1):

ctaatggcac tgactcagcc tcccatgtgc ttactgctaa gccagccaata ctgctctagc acacgtagca atgcctgtcc gtgaaaccaa cccctgggcc catgtccctg atgctgctaa caaggaaatt gcagccatac atccgg

In embodiments, the target sequence may be located within subregions of the regions underlined above. In particular, in embodiments the target region may be located within the region defined by sequence SEQ.ID NO: 44. In other embodiments, the target regions may be located within the region defined by sequence SEQ.ID NO: 31. In embodiments the target region may be located within the region defined by sequence SEQ.ID NO: 32. In other words, the AONs according to embodiments of the invention may comprise a sequence that is complementary to at least 7 nucleotides located within one of the regions in bold in the sequences above, or homologues thereof.

In embodiments, the target sequence (also referred to herein as "target region") may be 7 nucleotides long and may be defined by SEQ ID NO: 45-77, 306-316, 124-159 or 212-247. In embodiments, the target sequence may be 13 nucleotides long and may be defined by SEQ ID NO: 78-104, 317-327, 160-189, or 248-277. In embodiments, the target sequence may be 21 nucleotides long and may be defined by SEQ ID NO: 105-123, 328-338, 190-211 or 278-299.

In embodiments, the target sequence (also referred to herein as "target region") may be located within any of the regions defined by sequence SEQ ID NO: 45-77, 306-316, 124-159 or 212-247. In embodiments, the target sequence may be located within any of the regions defined by sequence SEQ ID NO: 78-104, 317-327, 160-189, or 248-277. In embodiments, the target sequence may be located within any of the regions defined by sequence SEQ ID NO: 105-123, 328-338, 190-211 or 278-299.

In embodiments, AONs according to the invention may comprise 7 nucleotides that are complementary to any of the sequences of SEQ ID NO: 45-77, 306-316, 124-159 or 212-247. In embodiments, AONs according to the invention may comprise 13 nucleotides that are complementary to any of the sequences of SEQ ID NO: 78-104, 317-327, 160-189, or 248-277. In embodiments, AONs according to the invention may comprise 21 nucleotides that are complementary to any of the sequences of SEQ ID NO: 105-123, 328-338, 190-211 or 278-299.

In embodiments, the target region may comprise 7 nucleotides; or more than 7 nucleotides, such as 8, 9, 10, 11, 12, 13, 14, 15, 16, 17, 18, 19, 20 or 21 nucleotides that are located within any of the regions underlined and optionally those regions shown in bold above. For example, the target region may comprise 13 nucleotides located within the regions defined by any of sequences SEQ ID NO: 9, 10, 11, 305, 44, 31 or 32. In other embodiments, the target region may comprise 18 to 21 nucleotides located within the regions defined by any of sequences SEQ ID NO: 9, 10, 11, 305, 44, 31 or 32. In other words, AONs according to the invention may comprise 7, 8, 9, 10, 11, 12, 13, 14, 15, 16, 17, 18, 19, 20 or 21 nucleotides that are complementary to 7, 8, 9, 10, 11, 12, 13, 14, 15, 16, 17, 18, 19, 20 or 21 nucleotides located within any of the regions underlined/in bold above. For example, AONs according to the invention may comprise 13 nucleotides that are complementary to 13 nucleotides located within the regions defined by any of sequences SEQ ID NO: 9, 10, 11, 305, 44, 31 or 32. In other embodiments AONs according to the invention may comprise 18 to 21 nucleotides that are complementary to 18 to 21 nucleotides located within any of sequences SEQ ID NO: 9, 10, 11, 305, 44, 31 or 32.

In embodiments, the AONs of the invention are suitably complementary to a portion of the sequence of a NUMB transcript. In such embodiment, the AONs may comprise a portion of sequence that is complementary to a target region of at least 7 nucleotides as explained above, and a portion of sequence that is complementary to a region of the NUMB transcript that does not lie within the regions described above. For example, an AON according to the invention may comprise a sequence that is complementary to the last 7 nucleotides of sequence SEQ ID NO:9 (or SEQ ID NO: 10, 11, 44, 31, 32), and additional nucleotides complementary with the part of the sequence of exon 9 that follows SEQ ID NO: 9 (i.e. SEQ ID NO: 4). Alternatively, the AONs may have a sequence such that every nucleotide of the AON is complementary with a nucleotide that lies within one of the regions identified above. For example, the AONs may have a sequence such that every nucleotide of the AON is complementary with a nucleotide of SEQ ID NO: 9 (or SEQ ID NO: 10, 11, 44, 305, 31, 32 or 33). Suitably, the sequences of the AONs of the invention are complementary to a sequence that is comprised within NUMB exon 9 (SEQ ID NO: 1, 2) or homologues thereof.

In embodiments, the target sequence may be located within subregions of the regions underlined above. In particular, in embodiments the target region may be located within the region defined by sequence SEQ.ID NO: 44, 3, 5-7, 9, 31-35. In embodiments, the antisense oligonucleotides according to the invention comprises a sequence selected from SEQ ID NO: 12, 13, 15-17 and 19-24, or homologues thereof.

Without wishing to be bound by theory, it is believed that the AONs of the invention will be particularly useful in the treatment of diseases or conditions that are associated with elevated levels of NUMB exon 9 inclusion compared to a healthy matched tissue. In particular, it is believed that the AONs of the invention will be particularly useful in the treatment of proliferative diseases where the NUMB protein acts to reduce cellular proliferation, since the isoform of NUMB that excludes exon 9 is associated with higher expression levels and reduced cellular proliferation, potentially via reduced activation of the Notch pathway or other cellular proliferation pathways. For example, the AONs of the invention have been shown (see Examples below) to have a beneficial effect in preventing cellular proliferation in multiple cancer cell lines, and to have beneficial effects on tumour progression (such as for example reversing tumour progression) in vivo and/or in vitro in multiple cancers. In particular, the AONs of the invention may be useful in the treatment of lung cancers (in particular lung adenocarcinomas), cervical cancer, breast cancer, colon cancer, brain glioblastoma, pancreatic cancer, acute monocytic leukemia, kidney cancer, colorectal cancer, liver cancer (e.g. hepatocarcinoma), and glioblastoma. The AONs of the invention may also be useful in the treatment of skin cancer (e.g. melanoma), stomach cancer, thyroid cancer and bone cancer. As such, the invention provides compounds and compositions for use in medicine and, in particular, for use in the treatment of cancers selected from lung cancers (in particular lung adenocarcinomas or lung squamous carcinoma), bladder cancer, cervical cancer, breast cancer, colon cancer, brain glioblastoma, pancreatic cancer, acute monocytic leukemia, kidney cancer, colorectal cancer, skin cancer (e.g. melanoma), stomach cancer, thyroid cancer and bone cancer. Methods for the treatment of such diseases are also provided. The uses and methods may comprise administering the AONs according to the invention to a patient in need thereof.

In embodiments, the invention provides pharmaceutical compositions comprising one or more AONs according to the invention. In embodiments, the compositions may comprise one or more pharmaceutically acceptable excipients. For example, the compositions according to the invention may comprise one or more AONs according to the invention and a buffer, such as water or a saline buffer (e.g. phosphate-buffered saline, PBS, preferably pharmaceutical grade PBS). In embodiments, the compositions may comprise solid or gel excipients, such as flavouring agents, thickeners, stabilisers, carriers, diluents, surfactants, penetration enhancers, emulsifiers and the like. For example, compositions according to the invention may comprise polyethylene glycol, gelatin, lactose, talc, silic acid, hydroxymethylcellulose, sodium carboxymethylcellulose, sorbitol, dextran, etc. In embodiments, a pharmaceutical composition according to the invention may comprise a delivery system, such as a liposome.

In embodiments, a pharmaceutical composition according to the invention may comprise one or more excipients selected from the group comprising: NaCl and/or HCl aqueous solutions; tartaric acid in aqueous solution, methyl parahydroxybenzoate in aqueous solution; polysorbate 20 (polyoxyethylene (20) monolaurate sorbitan monolaurate); dihydrated monosodic phosphate; anhydrous disodic phosphate in aqueous solution; sodium methylparahydroxybenzoate; propylparahydroxybenzoate in aqueous solution; EDTA/NaOH at pH 6.5 in aqueous solution; EDTA/NaOH at pH 7.5 in aqueous solution; EDTA, NaCl, polysorbate 80, citric acid, Na citrate in aqueous solution; NaCl and CaCl in aqueous solution; NaCl, $H_2SO_4$ and NaOH at pH 7 in aqueous solution; trometamol, ethanol 96%, NaCl, HCl in aqueous solution; trometamol, ethanol 96%, NaCl, HCl in aqueous solution; sorbitan trioleate; menthol; norflurane (HFA-134a), Oleic acid, citric acid, HFA-134a, glycerol; cetylpyridinium chloride, sorbitan trioleate; norflurane; HFA-227; polyvinylpyrrolidone K30, polyethylene glycol 600; norflurane sorbitan; trioleate, magnesium stearate; sugars (e.g. lactose, glucose, mannitol, trehalose, etc.); Mg stearate, lipids (such as DPPC, DSPC, DMPC, cholesterol, etc.); amino acids (e.g. leucine, trileucine); surfactants (e.g. poloxamer); bile salts; absorption enhancers (e.g. hydroypropylated-β-CD, natural γ-CD); chitosan; trimethylchitosan; and biodegradable polymers (e.g. PLGA).

In embodiments, a pharmaceutical composition according to the invention may comprise one or more solvents or cosolvants, such as organic solvents (acetone, acetic acid, acetonitrile, benzene, carbon tetrachloride, methylene chloride etc.) and inorganic solvents(liquid ammonia, liquid sulfur dioxide, sulfuryl chloride and sulfuryl chloride fluoride, phosphoryl chloride, dinitrogen tetroxide, antimony trichloride, bromine pentafluoride, hydrogen fluoride, pure sulfuric acid etc.) In embodiments, a pharmaceutical composition according to the invention may comprise one or more propellants, such as trichloromonofluoromethane, dichlorodifluoromethane, dichlorotetrafluoroethane, or other chlorofluorocarbon propellants; chlorodifluoromethane, trifloromonofluoroethane, chlorodifluoroethane, difluoroethane, heptafluoropropane, or other hydrochlorofluorocarbon and hydrofluorocarbon propellants; propane, isobutene, butane, pentane or other hydrocarbon propellants; nitrogen, nitrous oxide, carbon dioxide, compressed air or other compressed gases propellants. In embodiments, a pharmaceutical composition according to the invention may comprise one or more preservatives, such as benzalkonium chloride, cetrimonium bromide, benzethoniun chloride, alkyltrimethylannonium bromide, EDTA/Benzalkonium chloride, benzoic acid, soric acid, potassium sorbate, propylene glycol, ethanol, sodium benzoate, thimerosal, benzyl alcohol, chlorhexidine, chloroactamide, trichlorocarban, 4-chlorocresol, 4-chloroxylenol, dichlorophene, hexachlorophene; methyl, ethyl, propyl, butyl Parabens and combinations thereof. In embodiments, a pharmaceutical composition according to the invention may comprise one or more humectants, such as propylene glycol, glycerol, polyethylene glycol. In embodiments, a pharmaceutical composition according to the invention may comprise one or more anti-foaming agents, such as insoluble oils, polymethylsiloxanes and other silicones, stearates, glycols or polydimethylsiloxane-silicon dioxide. In embodiments, a pharmaceutical composition according to the invention may comprise one or more wetting agents, such polysorbates (e.g. Tweens), sorbitan esters (Spans), polysorbates, polysorbates, poloxamers, lecithin, soya lecithin, sodium lauryl sulphate, or hydrophilic colloids such as bentonite, tragacant, alginates, and cellulose derivatives. In embodiments, a pharmaceutical composition may comprise a nanoparticle-based drug formulation/delivery mechanism.

As the skilled person would understand, the appropriate mode of administration of the compounds and compositions of the invention may vary depending on whether local or systemic administration is desired, as well as depending on the area to be treated. In embodiments, administration may be topical, pulmonary, oral or parenteral. In embodiments, the compounds and compositions of the invention may be administered orally, ophthalmically, intranasally (e.g. via an inhaler, insufflation of powders or aerosols, using a nebuliser), intratracheally, by injection (e.g. intravenous, intraarterial, subcutaneous, intramuscular, intraperitoneal, intramuscular, intracranial, etc.), topically or transmucosally (e.g. using transdermal patches, ointments, lotions, suppositories, sprays, liquids, powders or gels). In embodiments, a pharmaceutical composition according to the invention comprises one or more AONs in a therapeutically effective amount. Similarly, methods of treatment of a disease or condition according to the invention may comprise administering the compounds or compositions of the invention in a therapeutically effective amount. In embodiments, a therapeutically effective amount is sufficient to prevent or alleviate the symptoms of a disease, reduce the size or the rate of progression of a tumour or cancer, and/or prolong the survival of the subject being treated. Determination of a therapeutically effective amount can be performed as known in the art, and may depend on the AON used, the method and frequency of administration, the disease treated, and/or the subject treated, etc.

In embodiments, methods of treatment of a subject using the compounds and compositions of the invention may comprise repeated administration of the compounds and compositions of the invention, as known in the art. In embodiments, methods of treatment of a subject using the compounds and composition of the invention may comprise administration of an antiproliferative drug in combination with the compounds and compositions of the invention, either sequentially, simultaneously or separately. In embodiments, methods of treatment of a subject using the compounds and compositions of the invention may comprise administration of a splicing modifying drug in combination with the compounds and compositions of the invention. 'In combination with', in the context of the invention, may mean that the two (or more) compounds may be administered either sequentially, simultaneously or separately, as desired.

In embodiments, methods of treatment of a subject using the compounds and composition of the invention may comprise testing the subject for elevated levels of NUMB exon 9 inclusion compared to a healthy subject and/or healthy tissue. For example, the methods of treatment according to the invention may comprise the steps of obtaining a sample (e.g. by biopsy) of a diseases tissue (e.g. a tumour), and quantifying the inclusion of NUMB exon 9 compared to a matched tissue from a healthy sample. Healthy and/or diseased samples may be liquid biopsy samples. In embodiment, the healthy sample may have been obtained from healthy tissue of the subject. In other embodiments, the healthy sample may have been obtained from healthy tissue of another subject. In yet other embodiments, the healthy sample may be a reference sample (e.g. a cell line). Quantifying the inclusion of NUMB exon 9 may be performed as known in the art, for example by performing RT-PCR, RNA sequencing, etc. and calculating the PSI for NUMB exon 9. The methods may further comprise administering the compounds or compositions of the invention if the data obtained at the previous step indicate that the diseased tissue shows elevated levels of NUMB exon 9 inclusion.

The invention will now be further illustrated by way of the following non-limiting examples.

EXAMPLES

Unless otherwise indicated, commercially available reagents and standard techniques in biology, chemistry and biochemistry were used.

Example 1: Exon 9 Inclusion is Increased in Many Different Types of Tumors

FIG. 1 shows the results of an investigation of the level of NUMB exon 9 inclusion (PSI=percent spliced in, i.e. proportion of transcripts where exon 9 is present compared to total number of transcripts for a given gene) in paired tumour/healthy samples for 11 tumour types using data from the TCGA consortium. The data shows that in at least Breast Invasive Carcinoma, Liver Hepatocellular Carcinoma, Lung Adenocarcinoma, Lung Squamous Cell Carcinoma and Prostate Adenocarcinoma, the distribution of PSI for exon 9 of NUMB across samples is significantly higher in the tumour samples than in the healthy samples (Mann Whitney U test, corrected for multiple testing using the Benjamini-Hochberg method). This indicates that regulation of NUMB exon 9 inclusion may be a potential avenue for therapy for many cancer types, in addition to lung adenocarcinoma.

Example 2: Identification of AONs Inducing NUMB Exon 9 Skipping

Having previously established that NUMB exons 9 inclusion could be modulated on lung cancer A549 cells using 2'-O-methyl phosphothioate-modified antisense oligonucleotides (AONs) complementary to a region of the pre-mRNA encompassing the 5' splice site (SS) (Bechara et al., 2013), the present inventors set out to identify new target regions that could be targeted by AONs to promote exon 9 skipping more efficiently.

A systematic scanning of NUMB exon 9 was performed using 21 nucleotide AONs complementary to consecutive, overlapping regions of the exon: a total of 24 AONs covering the 144 nucleotide exon were used in this study. AONs complementary to regions of the pre-mRNA encompassing the 3' SS or the 5' SS, the branch point (BP) region or a random sequence (RND) were included as controls.

Figure 2:
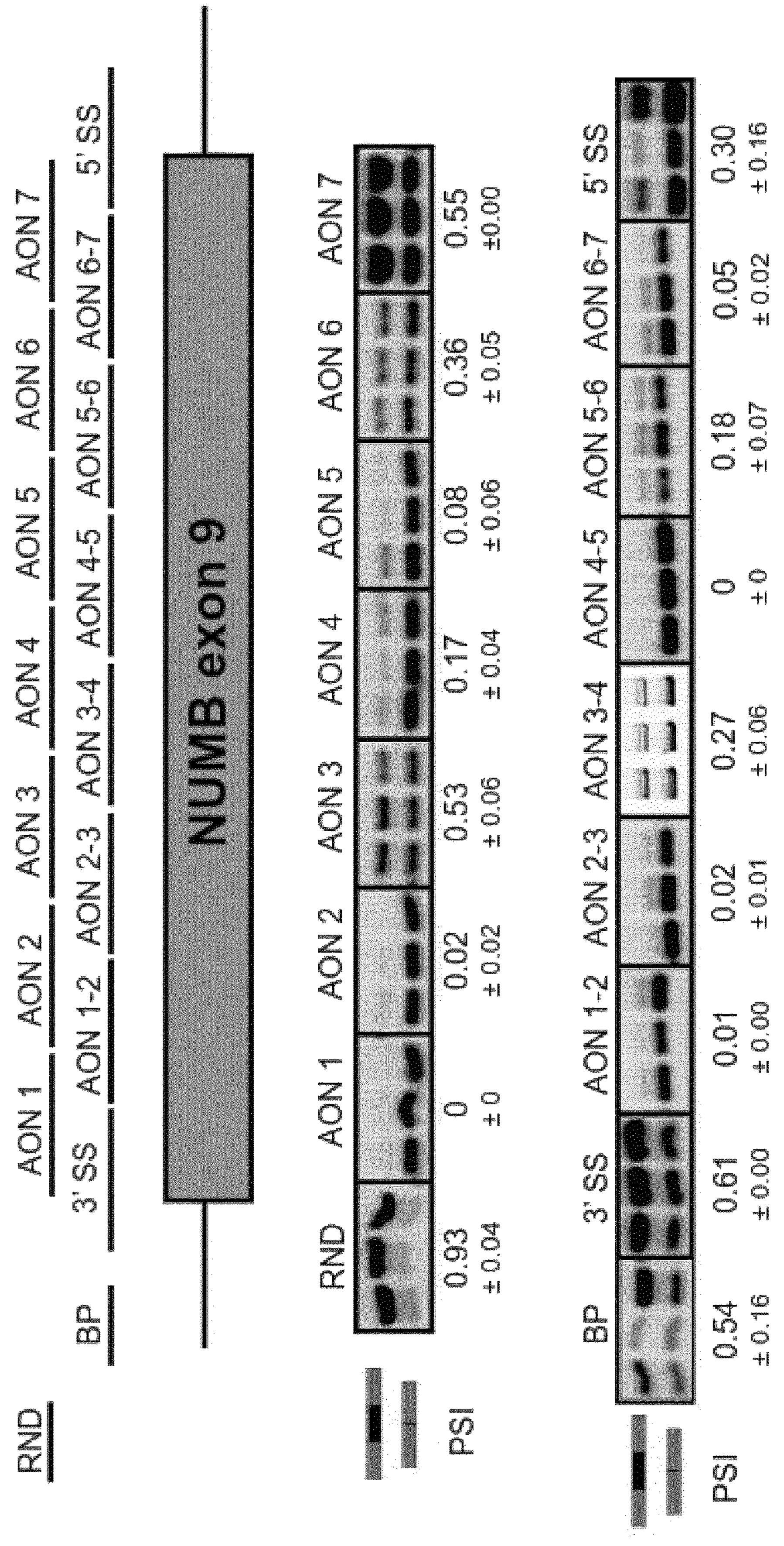
FIG. 2 shows the design (top) and results (middle and bottom) of a systematic scanning of NUMB exon 9 using 21 nt long AONs; cells expressing a reporter exon 9 minigene were transfected with AONs according to the top panel, their RNA was collected after 24 hours and RT-PCR was performed with primers specific for detecting NUMB exon 9 inclusion/skipping in the minigene; the middle and bottom panels show the relevant region from polyacrylamide gels following electrophoretic separation of the PCR amplified products, and the percent splice in (PSI) that correspond to the data.

FIG. 2 shows the results of this analysis. As can be seen in FIG. 2, cells transfected with the random AON show almost full exon 9 inclusion (PSI=0.93). Targeting the branch point region with the AON of SEQ ID NO: 29 also had a very limited effect. By contrast, transfection with any of the AONs complementary to exon 9 (AON1 to AON7, which correspond to SEQ ID NO:12 to 18, respectively, and AON1-2, 2-3, 3-4, 4-5, 5-6 and 6-7 corresponding to SEQ ID NO:19 to 24) resulted in significant exon 9 skipping. In some cases, surprisingly, the level of exon skipping that can be obtained by targeting sequences within exon 9—in accordance with the invention—is higher than that which can be obtained using AONs that target the splice sites of exon 9 (i.e. AONs of SEQ ID NO: 25 and 26, respectively for the 5' and 3' splice sites—targeting the sequences of SEQ ID NOs: 27 and 28, respectively).

In particular, three regions of exon 9 were identified which, when targeted by AONs of the invention, resulted in particularly efficient exon 9 skipping: these three regions are the combined regions targeted by AON1, AON2, AON1-2 and AON2-3 (i.e. the region of exon 9 having the sequence of SEQ ID NO: 305), and in particular the combined regions targeted by AON1 and AON2 (also including the region targeted by AON1-2; i.e. the region of exon 9 having the sequence of SEQ ID NO: 9); the combined regions targeted by AON4, AON5 and AON4-5 (i.e. the region of exon 9 having the sequence of SEQ ID NO:10); and the combined regions targeted by AON6 and AON6-7 (i.e. the region of exon 9 having the sequence of SEQ ID NO: 11). When each of these regions was targeted by AONs, the PSI for exon 9 was reduced to 0-0.02 for the region of exon 9 having the sequence of SEQ ID NO: 305 (targeted by AON1, AON2, AON1-2 and AON2-3; i.e. SEQ ID NO: 12, 13, 19 and 20); 0-0.17 (region of exon 9 having the sequence of SEQ ID NO:10 (targeted by AON4, AON5 AON4-5; i.e. SEQ ID NO:14, 15 and 22); and 0.05-0.55 (region of exon 9 having the sequence of SEQ ID NO: 11 (targeted by AON6, AON7, AON6-7; i.e. SEQ ID NO: 16, 17 and 24). Within those regions, subregions targeted by AON1 (SEQ ID NO: 12), AON1-2 (SEQ ID NO: 19), AON4-5 (SEQ ID NO: 22) and AON6-7 (SEQ ID NO: 24) in particular—respectively the regions of exon 9 having the sequences of SEQ ID NO: 30, 31 and 32—resulted in almost complete exon 9 skipping when targeted by AONs.

This data indicates that the targeting of specific regions within exon 9 of NUMB with AONs results in effective skipping of exon 9 in full length NUMB transcripts.

Example 3: AONs According to the Invention are Efficacious at Low Concentration and on Endogeneous NUMB Transcripts Investigations were carried out to determine whether the beneficial regions identified in the studies of Example 2 could be used to regulate exon 9 inclusion in endogeneous NUMB transcripts in a lung adenocarcinoma cell line (A549), and whether any such regulation would be concentration-dependent. The A549 lung adenocarcinoma cell line displays high levels of NUMB exon 9 inclusion and NUMB splicing is known to control cell proliferation in this cell line (Bechara et al., 2013).

Three different concentrations (5, 10 and 50 nM) of AON 1 (SEQ ID NO: 12) and AON 4-5 (SEQ ID NO: 22) were transfected into A549 cells and, 24 hours after transfection, RNA was isolated and the endogenous levels of NUMB exon 9 inclusion/skipping were measured by RT-PCR. A random AON (RND) was used as a control.

Figure 3A:
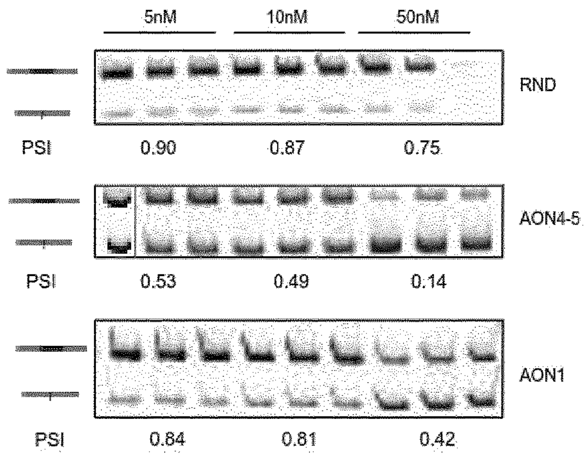
FIGS. 3A and 3B show the effect on endogenous NUMB exon 9 inclusion in A549 lung adenocarcinoma cell line following transfection with three different concentrations of two AONs according to the invention alongside a control AON based on a randomised sequence of 21 nts; separate lung adenocarcinoma cell populations were transfected with one of two AONs of the invention at three different concentrations; RNA was collected after 24 hours and RT-PCR was performed with primers specific for detecting NUMB exon 9 inclusion/skipping.
Figure 3B:
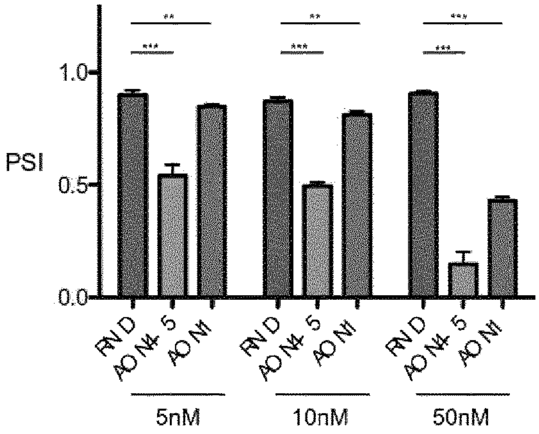

FIGS. 3A and 3B show the results of this analysis. The data of FIG. 3A (polyacrylamide gels following electrophoretic separation of the RT-PCR products above, quantified on FIG. 3B) shows that titrable effects on exon skipping can be detected for both AON1 and AON 4-5 even at 5 nM, which progressively increases at higher AON concentrations. By contrast, no effect was detected using the random AON negative control. Note that at 50 nm, NUMB transcripts without exon 9 represent the majority of the NUMB transcripts in cell culture (i.e. PSI <0.5). These differences in PSI are significant (Students t-test, *P-value <0.05, P-value<0.005, *P-value<0.001) despite the fact that the transfections are extremely unlikely to result in 100% of the cells being transfected. As such, some of the cells in the culture would be non-transfected and so the PSI in cells that were transfected is expected to be lower than the global PSI that was measured here.

Example 4: AONs According to the Invention Reduce Exon 9 Inclusion in Lung Adenocarcinoma Mouse Models and a Human Lung Adenocarcinoma Cell Line The effect of AON1 (SEQ ID NO: 12), which targets a sequence of NUMB exon 9, which is conserved between human and mouse, was tested in four different lung adenocarcinoma KRAS-G12V-derived mice cell lines (KLC1 to 4, Ambrogio et al., 2014).

Figure 4A:
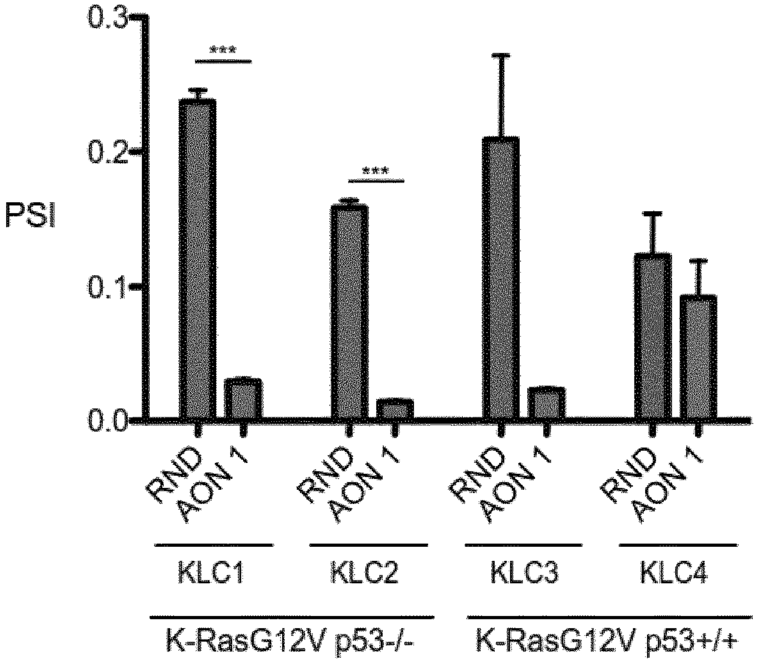
FIGS. 4A and 4B show the effect of an AON according to the invention on NUMB exon 9 skipping in lung adenocarcinoma mouse model cell lines. Four different lung adenocarcinoma KRAS-G12V-derived mice cell lines with different p53 status were used (FIG. 4A) along with a human lung adenocarcinoma cell line (FIG. 4B)

AON1 or a random control was transfected at a concentration of 50 nM in each of the four cell lines. RNA was isolated 24 hours after transfection, NUMB mRNA was PCR amplified and the levels of NUMB exon 9 inclusion/skipping were measured by capillary electrophoresis. The results of this analysis are shown on FIG. 4A. This figure demonstrates that although NUMB exon 9 skipping is very prominent in these cells, the AONs further significantly decrease PSI values in almost all cell lines (apart from KLC4). However, the effect is more prominent in p53−/− cells compared to p53+/+ cells (compare KLC1, KLC2 vs KLC3, KLC4). These data show that the effect is reproducible in mouse lung adenocarcinoma models, even when the level of exon 9 inclusion is lower, and also that the effect is not p53 dependent, although a stronger effect is observed in cells deficient for p53.

Figure 4B:
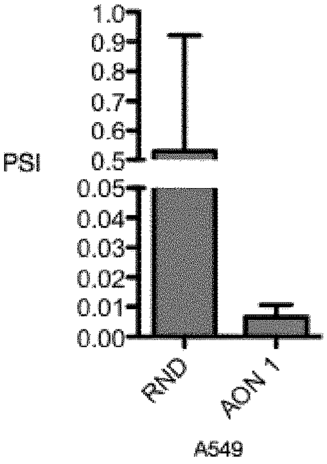

Similar results were obtained with a human lung adenocarcinoma cell line (A549), as shown on FIG. 4B.

Figure 5:
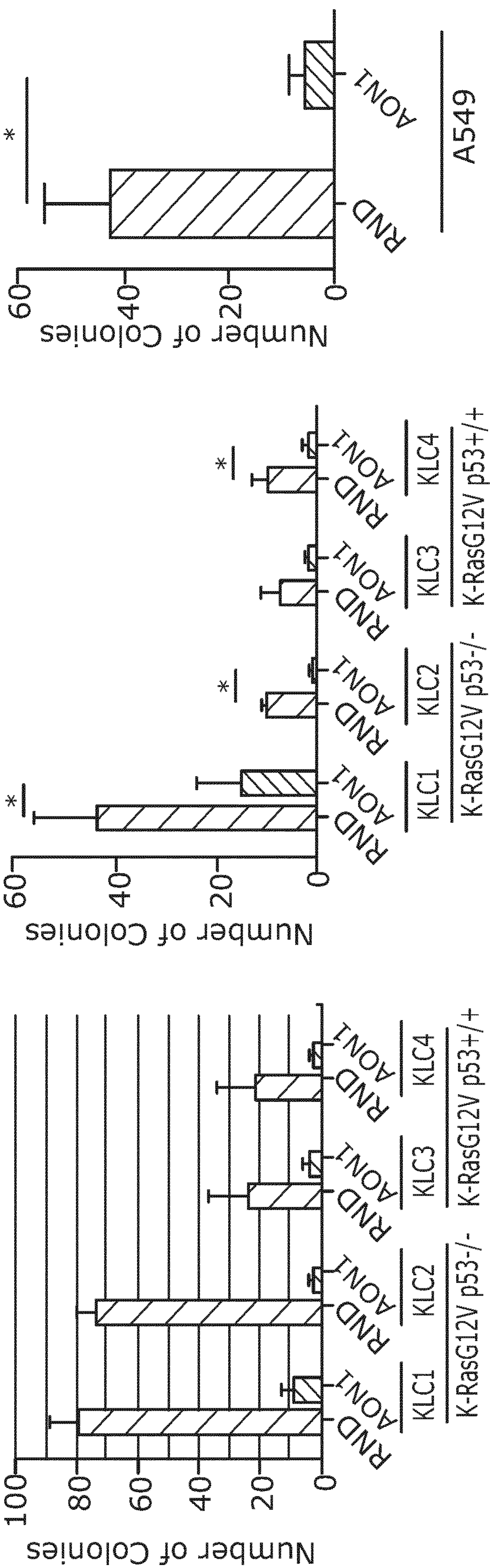
FIG. 5 shows the effect of an AON according to the invention on colony formation in lung adenocarcinoma mouse model cell lines (four different lung adenocarcinoma KRAS-G12V-derived mice cell lines with different p53 status were used) and a human lung adenocarcinoma cell line, at two different concentrations: 100 nM (left), and 50 nM (middle) in the mouse model cell lines, and a concentration of 100 nM in the human cell line (right)

Example 5: AONs According to the Invention Reduce Colony Formation in Lung Adenocarcinoma Mouse Models and Human Cell Lines The colony formation potential after transfection with AON1 was tested on the same cell lines as in Example 4, as well as the human lung adenocarcinoma cell line A549. Two concentrations of AON1 were tested: 100 nM (left panel and right panel on FIG. 5), and 50 nM (middle panel on FIG. 5) in biological triplicates. The results of this analysis are shown in FIG. 5. Note that the KCL4 cell line has limited clonogenic capacity even under control conditions. The results indicate that the reduction in NUMB exon 9 inclusion correlates with a reduced potential for colony formation.

Example 6: Predictive Analysis of Regulatory Binding Sites within Exon 9

Figure 6:
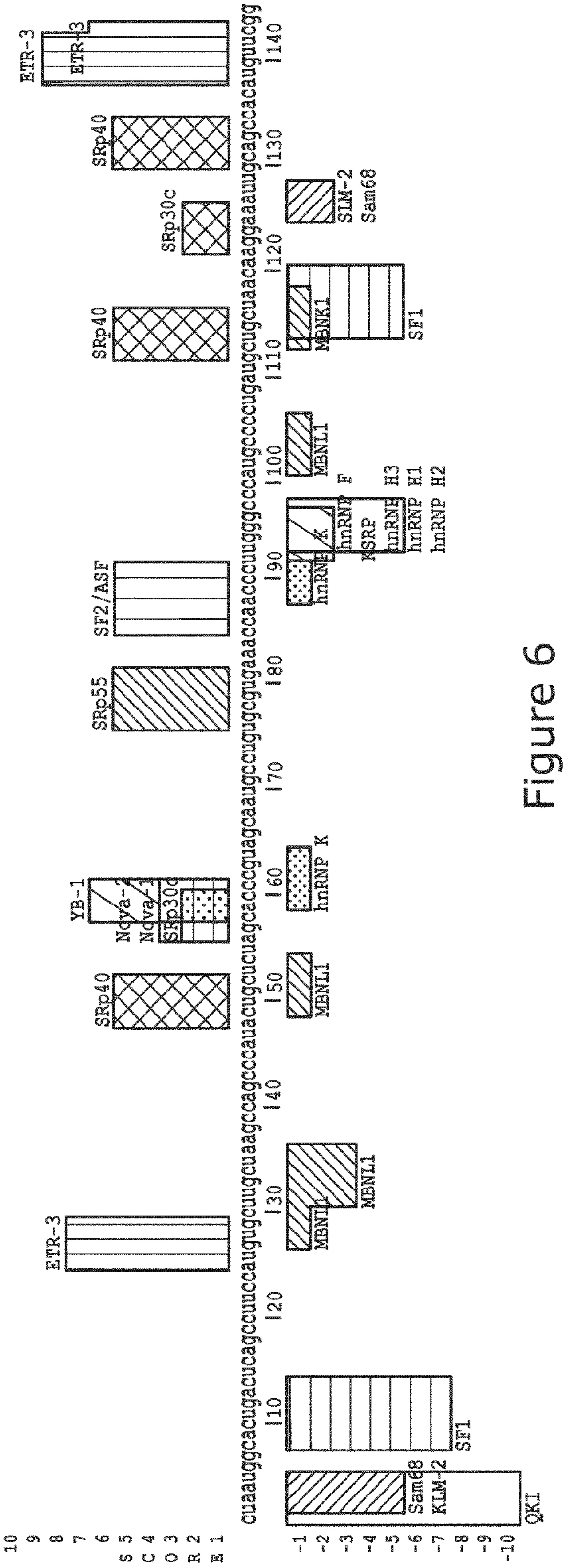
FIG. 6 shows the results of a computational prediction of potential binding sites for known endogenous splicing regulators in the human NUMB exon 9 nucleotide sequence.

A bioinformatics analysis was performed to identify potential binding motifs for splicing regulators. In particular, algorithms that predict binding sites for human splicing regulatory factors on the basis of the nucleotide sequence preferences obtained experimentally through various approaches (SpliceAid web tool, see http://www.introni.it/splicing.html) were used to identify potential binding sites for these factors within the sequence of exon 9. The whole human NUMB exon 9 sequence was used. The results are shown on FIG. 6. The analysis revealed a potential binding site for SF1/BBP (Branchpoint Binding Protein) in the region spanning +8 to +16 of NUMB exon 9 (GGCACTGACTC, SEQ ID NO: 300). Three mutants of the RG6-NUMB minigene were produced, as well as the wild type sequence (WT: GGCACTGACTC, SEQ ID NO: 301):

Mut3, which is predicted to disrupt the SF1/BBP binding site (GGCACTGACTCCTC>GGCACTCACCTC, SEQ ID NO: 302); and Mut4 (GGCACTGACTCCTC>GGCACCGACTC, SEQ ID NO: 303) and Mut1 (GGCACTGACTCCTC>GGTACTGACCTC, SEQ ID NO: 304), which are predicted to have a milder effect. The four minigenes (wild-type, Mut1, Mut3 and Mut4) were co-transfected in HEK-293 cells at constant concentrations with increasing concentrations of a SF1/BBP expression vector. 48 hours after transfection, RNA and protein samples were collected and the fraction of exon 9 inclusion (PSI) was quantified by RT-PCR and capillary electrophoresis, while the levels of SF1/BBP overexpression were estimated by western blot using a specific antibody. While mutant Mut1 slightly increased exon 9 skipping, Mut2 did not show any effect (data not shown). Overexpression of SF1/BBP showed a slight tendency towards increased exon 9 inclusion for the three reporter minigenes, but the effects were not quantitatively significant. It was therefore concluded that SF1/BBP (and in particular, inhibition of SF1/BBP binding by action of the AONs of the invention) is unlikely to mediate the effects of the target regions identified.

Figure 7A:
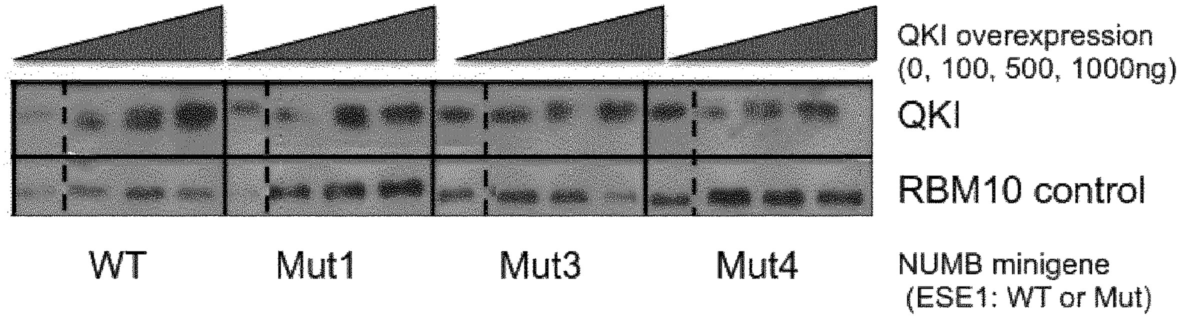
FIGS. 7A and 7B show the results of an analysis of the relationship between QKI expression and exon 9 inclusion.
Figure 7B:
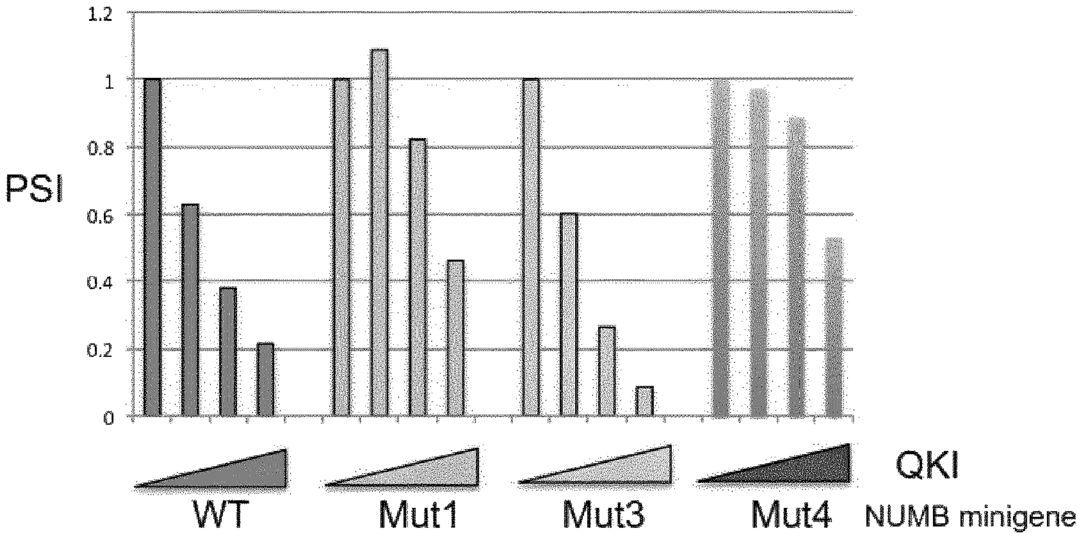

As the SF1/BBP motif (ACUNAC) is very similar to the consensus QKI binding site (ACUAAY), which has been described to regulate NUMB alternative splicing in lung cancer (Zong et al., 2014), it was decided to test the effect of QKI overexpression in the minigene reporter constructs above. The results of this analysis are shown on FIGS. 7A and 7B.

These results show that QKI overexpression (see FIG. 7A) led to increased levels of exon 9 skipping in the wild-type reporter (FIG. 7B), which is consistent with previous results (Zong et al., 2014). Given that excess QKI causes NUMB exon 9 skipping, it is also unlikely that QKI would be the transacting factor that promotes NUMB exon 9 inclusion as a result of the targeting of NUMB exon 9 by AON1. Indeed, the presence of AON1 would likely compete for the binding site of QKI. In other words, the fact that both AON1 and QKI promote exon skipping indicates that AON1 is unlikely to act by blocking QKI.

Example 7: AONs According to the Invention Reduce Exon 9 Inclusion and Tumour Progression In Vivo In order to demonstrate that the AONs of the invention can be effective in vivo, 100 μl of AON1 at a concentration of 3,100 ng/μl in PBS (an approximate concentration of 12 μg of AON1/gram of mouse weight) were administered intratracheally to a wild-type BL6 adult male mice. 78 hours after the administration the animals were sacrificed and lung and liver samples were collected. RNA was isolated from the tissues and endogenous NUMB exon 9 PSI values were measured by RT-PCR. The results of this analysis are shown on FIG. 8.

Figure 8:
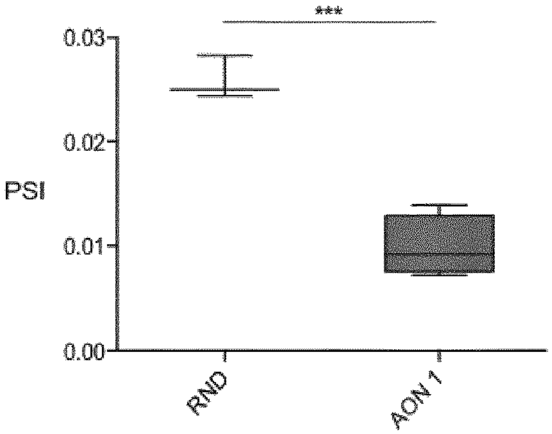
FIG. 8 shows the result of an analysis of the effect of intratracheal administration of an AON of the invention to healthy mice; a significant reduction in NUMB exon 9 inclusion is observed in the lung 78 hours after administration.

As shown, the administration of AON1 into the lung of healthy mice led to a significant (Student's t-test, p.value<0.001) reduction in NUMB PSI values (FIG. 8 shows the results over 4 mice compared to a control of 3 mice administered with random AON), while it did not have detectable effects in the liver (data not shown).

This assay shows that despite the fact that the levels of exon 9 inclusion in endogeneous NUMB transcripts in the lungs of healthy mice are very low, AON1 was capable, when administered directly to the lung, of inducing a significant further increase in exon skipping. This data further indicates that a potent effect may be expected in tumours that display higher levels of NUMB exon 9 inclusion.

Figure 9A:
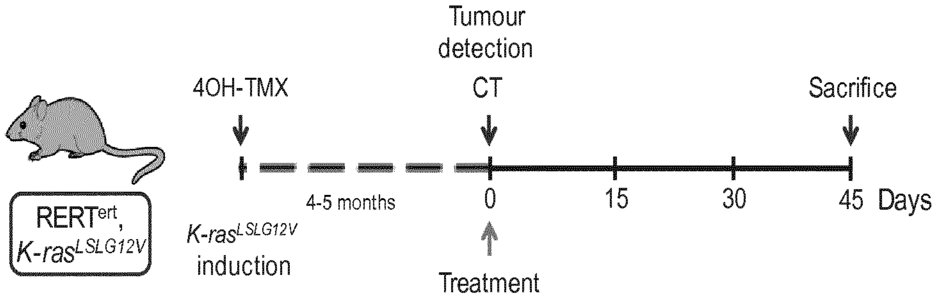
FIGS. 9A and 9B show an experimental design (FIG. 9A) for testing the effect of an AON of the invention on NUMB exon 9 inclusion in a genetic mouse model of KRAS-G12V driven non-small cell lung carcinoma, where the AON is administered intratracheally (FIG. 9A); and the results thereof (FIG. 9B)
Figure 9B:
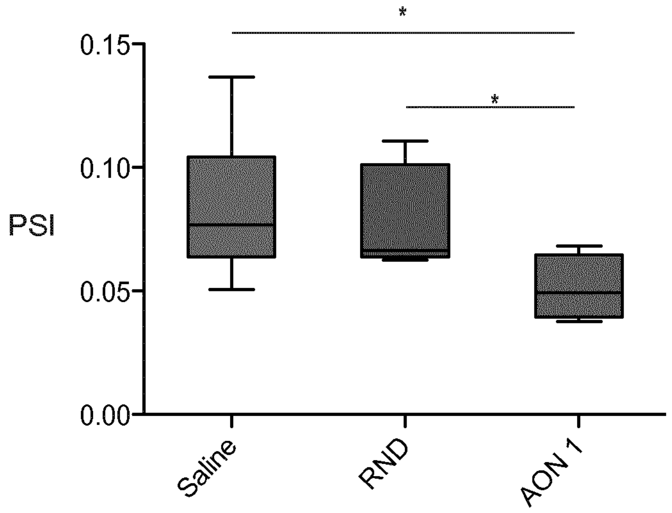

The inventors then went on to test whether AON1 could modulate NUMB alternative splicing in lung tumours. A genetic mouse model of KRAS-G12V-driven non-small cell lung carcinoma (Guerra et al., 2003) was used for this purpose. As illustrated on FIG. 9A, young adult mice were treated with tamoxifen around 6 months of age to induce the activation of Cre, which by removing an engineered premature STOP codon before the oncogenic KRAS-G12V, leads to expression of the oncogenic version of the protein. 6 to 8 months after the administration of tamoxifen, mice started to develop lung adenomas. At that point mice were treated with a single intratracheal administration of AON1, a random AON-RND (using an approximate concentration of 12 μg of AON1-RND/gram of weight of the mice) or a saline buffer and sacrificed 3 weeks after. Lung samples were extracted and tumors were microdissected. Non-tumoral lung samples were also collected. Samples were processed as above with healthy mice. The results of this analysis are shown on FIG. 9B (results obtained for 4 tumors coming from 2 AON1 treated mice, 5 tumors coming from 3 mice treated with AON RND and 6 tumors coming from 2 saline treated mice). These results indicate that the levels of NUMB exon 9 inclusion in tumors treated with control AONs or saline buffer were more than 3-fold higher than in healthy tissue (compare PSI values of RND between FIGS. 8 and 9B). The PSI values of non-tumoral tissue in KRAS-G12V-activated mice were also higher and comparable to the tumors (data not shown), which may be explained by the existence of premalignant lesions induced by oncogenic KRAS activation in the apparently non-tumoral tissue. Further, the administration of AON1 was able to reduce significantly the levels of NUMB exon 9 inclusion in the treated tumors (see FIG. 9B). No significant differences between administrating saline buffer or the RND AON were observed, indicating that the control AON does not alter the ratios of the NUMB isoforms.

Taken together, the results suggest that a single intratracheal administration of AON1 is capable of significantly reducing NUMB exon 9 inclusion in KRASG12V derived tumors, which suggests that it could also have an impact on the growth of these tumours. The change in NUMB splicing was maintained at least during 3 weeks after the administration (see FIG. 9B), suggesting the possibility of long-term effects.

Figure 10A:
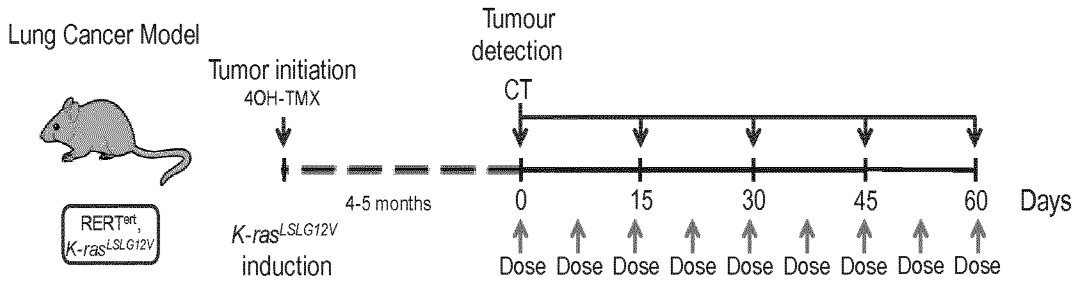
FIGS. 10A, 10B and 10C show an experimental design for testing the effect of an AON of the invention on tumour progression in a genetic mouse model of KRAS-G12V driven non-small cell lung carcinoma, where the AON is administered intranasaly (FIG. 10A); and the results thereof (FIGS. 10B and 10C)

The effect of AON1 on tumour progression was also analysed, as explained on FIG. 10A. The same lung cancer mouse model described above (KRAS-G12V) was used and 4-5 months after the tamoxifen administration, when the tumors were detectable by micro CT, mice were treated with either AON1 or a random AON, RND. Weekly intranasal administrations of 100 μl of AON (at a concentration of 3,100 ng/μl) were performed to each mouse (regardless of their weight). Tumor growth was followed every two weeks by micro CT.

Figure 10B:
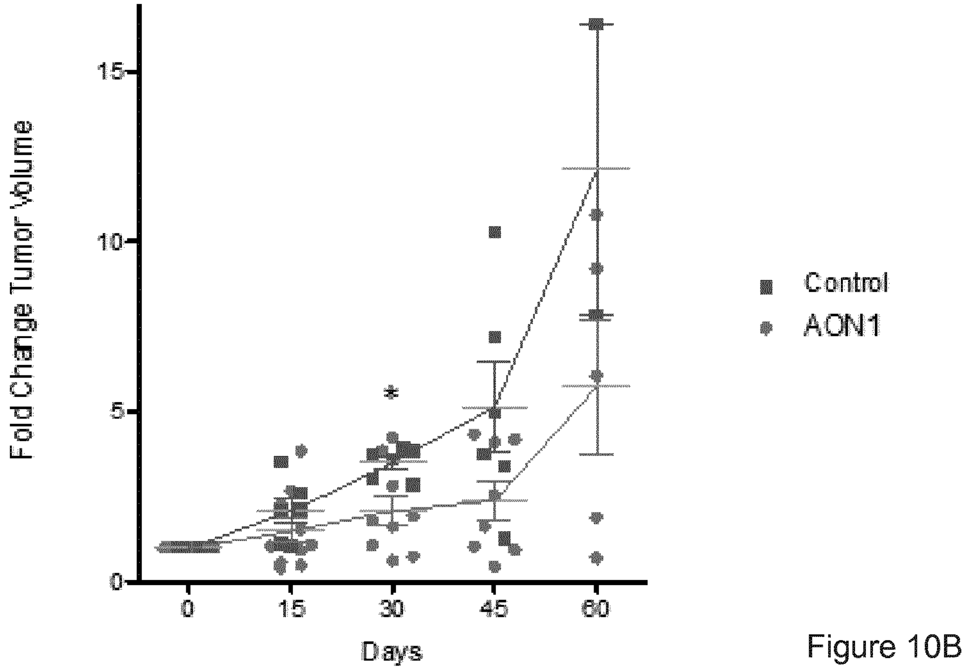
Figure 10C:
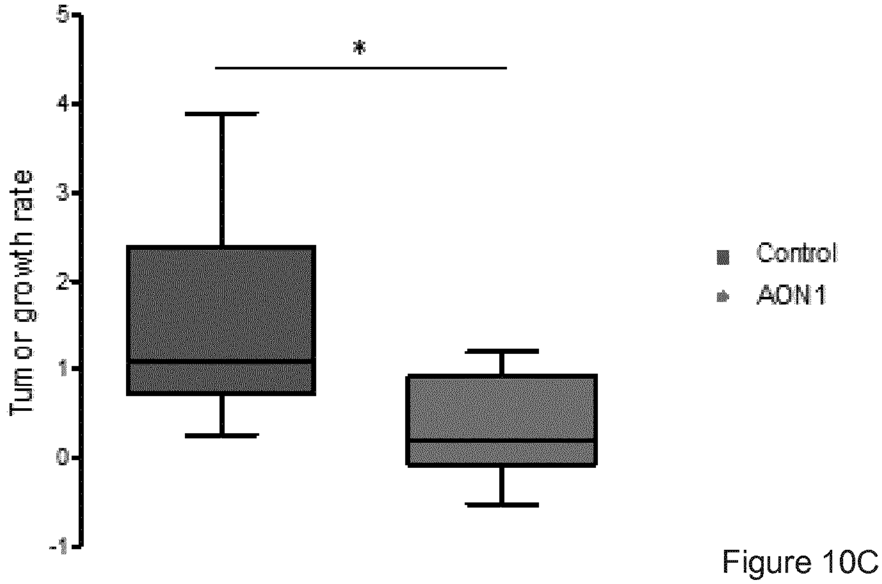

The results of the follow-up on tumor growth are summarised in FIGS. 10B and 10C (3 mice treated with the RND AON and 2 with AON1). These data suggest that the treatment of lung tumors in a KRAS-V12D mouse with AON1 can have therapeutic effects for preventing tumor growth. 45 days after starting the treatment, the size of the AON1-treated tumors was significantly reduced while the control tumors continue to grow.

The effect of AONs according to the invention (in particular AON4-5, SEQ ID NO: 22) was analysed after intravenous injection to an adult (3 months old) healthy mice.

Figure 11A:
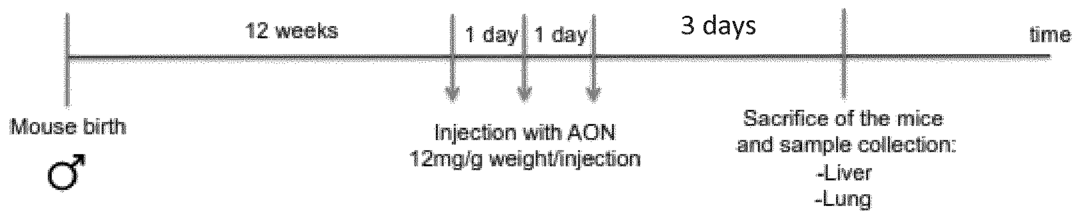
FIGS. 11A, 11B and 11C show an experimental design for testing the effect of an AON of the invention on NUMB exon 9 inclusion in a healthy adult mouse, where the AON is injected intravenously (FIG. 11A); and the results thereof (FIGS. 11B and 11C, respectively showing the effect in the liver and the lung)
Figure 11B:
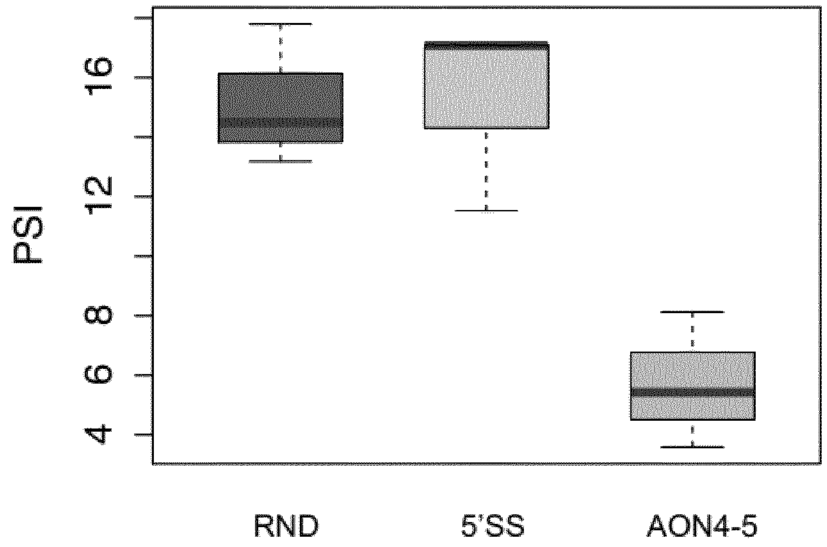
Figure 11C:
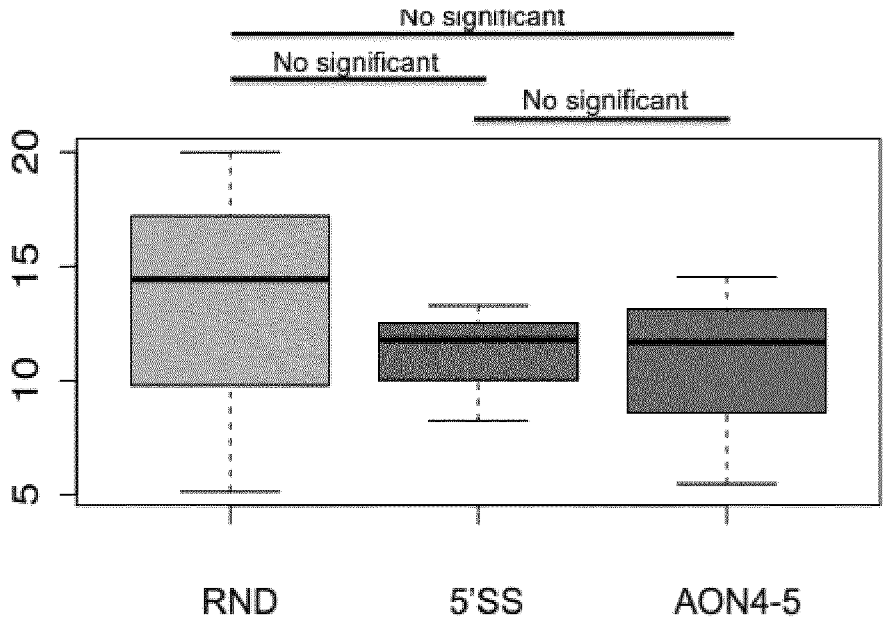

100 μl of AON4-5 (SEQ ID NO:22), a random AON (RND) or an AON (SEQ ID NO: 25) targeting the 5'SS (SEQ ID NO: 27) at a concentration of 3,100 ng/μl in PBS (an approximate concentration of 12 μg of AON1/gram of mouse weight) were administered intravenously (by retro orbital sinus injection) to a wild-type BL6 adult male mice, as shown on FIG. 11A. Three once-daily injections were performed (i.e. an injection was performed every 24 hours up to a total of 72 hours). 78 hours after the last administration the animals were sacrificed and lung and liver samples were collected. RNA was isolated from the tissues and endogenous NUMB exon 9 PSI values were measured by RT-PCR. The results of this analysis are shown in FIGS. 11B and 11C (3 mice per condition), respectively for the liver and lung.

These data indicate that the effect associated with the AONs or the invention may be dependent on the administration mode. For example, in order to target the liver, intravenous administration may be appropriate, whereas for administration to the lung administration to the respiratory system may be more appropriate.

Figure 12A:
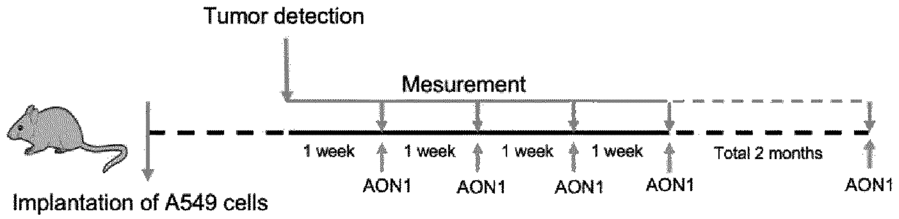
FIGS. 12A and 12B show an experimental design for testing the effect of intranasal administration of two different AONs of the invention in an orthotopic model of lung adenocarcinoma (FIG. 12A); and the results thereof (FIG. 12B)
Figure 12B:
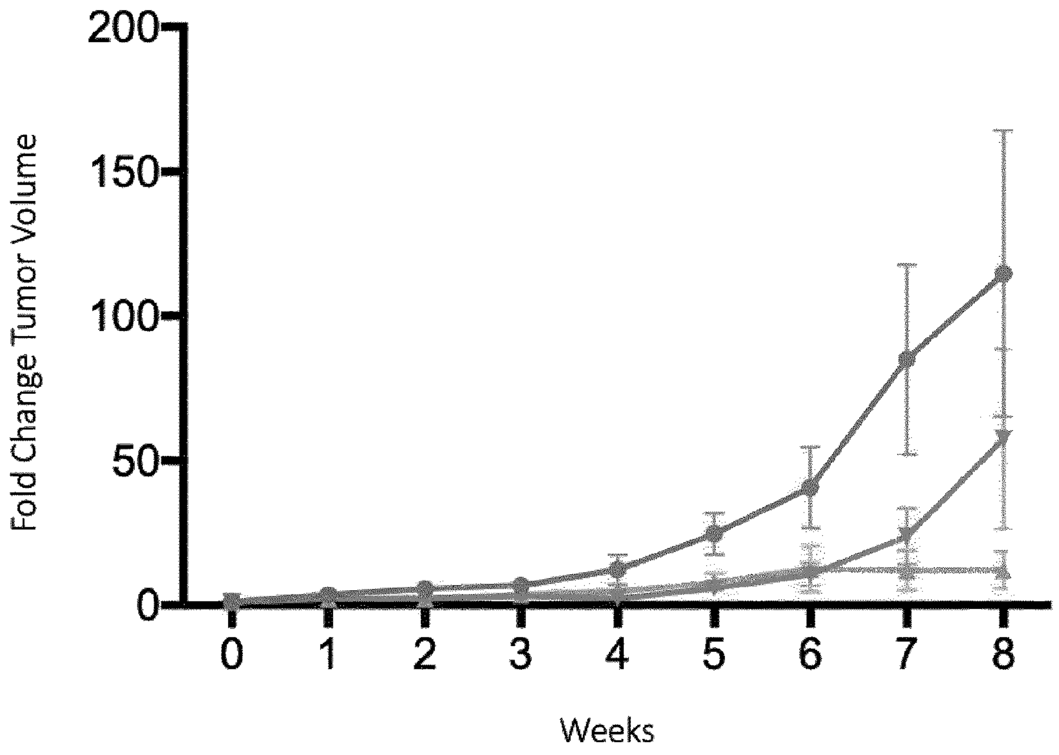

Finally, the effect of AON1 (SEQ ID NO:12) and AON6-7 (SEQ ID NO: 24) on tumour growth in vivo was further tested using an orthotopic mouse model of lung cancer, in which SCID-BEIGE mice of approximately 6 weeks are intratracheally inoculated with human A549 lung cancer cells that stably express luciferase, as explained in FIG. 12A. The proper inoculation of the cells was verified by an in vivo analysis of the luminescent signal. Starting a month after the intratracheal inoculation, the tumour growth was monitored weekly. The mice were anesthetized and 100 μl of a solution of luciferine in sterile PBS (100 mg/Kg concentration) was injected intreaperitoneally; 10 minutes after injection the luminescent signal was measured using an In Vivo Imaging System (IVIS) by Perkin Elmer®. Once the tumoral mass reached a certain volume, the treatment was started. Mice were intranassally instillated with 100 μl of the AON (AON1 (SEQ ID NO: 12) or AON6-7 (SEQ ID NO: 24)) resuspended in sterile PBS at a concentration of 3,100 ng/μl. Tumor growth (fold change tumor volume was monitored) and the probabilities of differential tumor growth between the groups was estimated using a log-linear random effects model, as explained in Bates et al., 2015. The data shown on FIG. 12B (the continuous lines on FIG. 12B indicating averages of the respective data sets, the control data being identified with circles (n=15 mice), the AON1 data being identified by with triangles pointing down (n=11), and the AON6-7 data being identified with triangles pointing up (n=11)) indicates that the AONs according to the invention reduce growth of lung cancer tumours in vivo (probability that the tumor growth is reduced in each of the treatment groups compared to the control>0.99, where the probability calculation is performed as explained above).

Figure 13:
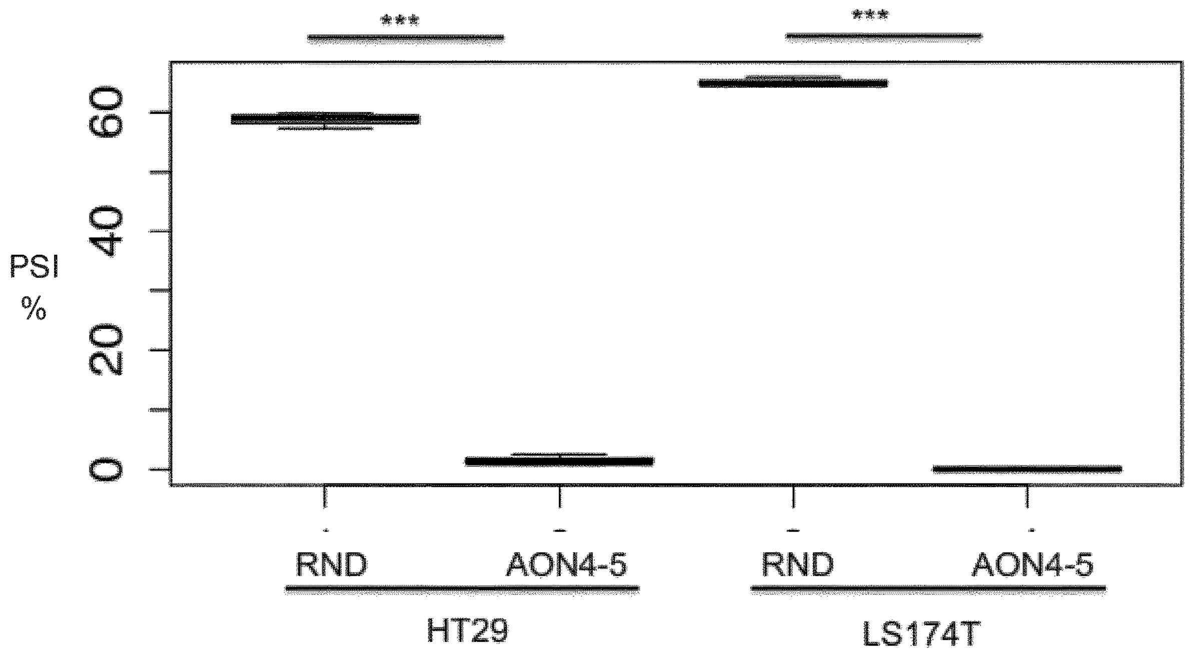
FIG. 13 shows the effect of treatment with an AON according to the invention on NUMB exon 9 inclusion in two different colon cancer cell lines (HT29 and LS174T)

Example 8: AONs According to the Invention Reduce Exon 9 Inclusion in Multiple Types of Cancer The effect of in vitro treatment of two different colon cancer cell lines (HT29 and LS174T) with an AON according to the invention (AON4-5, SEQ ID NO: 22) was tested to show the wide applicability of the AONs of the invention. Populations of 250,000 HT29 cells and 250,000 LS147T cells were cultured in 6-well plates 24 h prior to the transfection. The cells were transfected using Lipofectamine® RNAiMax from ThermoFisher, as explained below, with 100 nM final concentration of the indicated AONs. Cells were collected 24 h after the transfection, RNA was extracted and NUMB alternative splicing was analysed by RT-PCR and capilar electrophoresis. The results are shown in FIG. 13, which demonstrates that a significant (Students t-test, ***P-value<0.001) reduction in PSI of NUMB exon 9 can be observed compared to a control in which a random AON was transfected.

Figure 14:
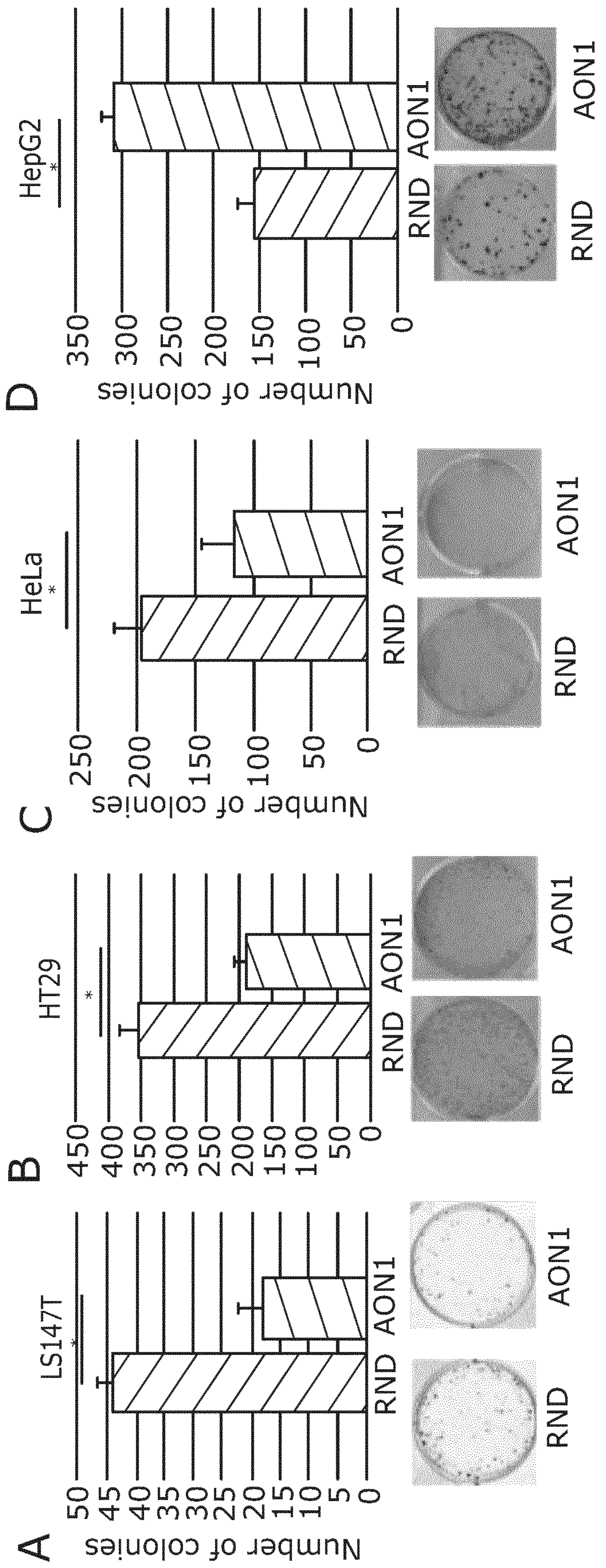
FIGS. 14A, 14B, 14C and 14D show the result of an analysis of the effect of an AON of the invention on colony formation in two different colon cancer cell lines (FIGS. 14A and 14B), a cervical cancer cell line (FIG. 14C), and a hepatocarcinoma cell line (FIG. 14D)

The effect of in vitro treatment on colony formation of the two different colon cancer cell lines (HT29 and LS174T), a cervix cancer cell line (HeLa), and a hepatocarcinoma cell line (HeG2) with another AON according to the invention (AON1, SEQ ID NO: 12) was then tested. The results of this analysis are shown in FIG. 14. This data indicates that transfection with AON1 results in a significant (Student's t-test, *P-value <0.05) reduction in the number of colonies of LS147T (FIG. 14A), HT29 (FIG. 14B), and HeLA (FIG. 14C). By contrast, transfection with AON1 results in a significant (Student's t-test, *P-value <0.05) increase in the number of colonies for HepG2 (FIG. 14D), in line with the understanding that NUMB protein plays a protumoral role in HepG2 (see e.g. Xie, C. et al., 2015).

The inventors then went on to investigate the effect of in vitro treatment with AON1 (SEQ ID NO: 12) on colony formation and exon 9 inclusion in a variety of cancer cell lines, compared to a random 21 nt long oligonucleotide (2'-O-Methyl phosphorotiotated RNA of sequence SEQ ID NO: 357). All cell lines were transfected at least in technical triplicates. Different concentrations of AON were used, depending on the cell line (either 10 nM, 50 nM or 100 nM, as indicated in Table 1 below). The number of colonies was normalised to the number of colonies of the same cell line transfected with the same concentration of random AON. Statistical significance was calculated using Student's t-test (*P-value<0.001, P-value<0.01, *P-value<0.05). The results of the colony counting experiments can be seen in FIG. 21. The levels of endogeneous NUMB transcript with or without exon 9 were quantified by capillary electrophoresis in order to calculate the PSI in each condition, and a DPSI value was calculated by subtracting the PSI value for the control (random AON) from the PSI values for the cells treated with AON1. The results of this analysis can be found in Table 1 below.

TABLE 1

Numb exon 9 inclusion values for various cell lines treated with AON1 vs. control

| Cell line | DPSI | AON concentration [nM] |
|---|---|---|
| A549 | −0.47 | 100 |
| H1395 | −0.41 | 10 |
| H1666 | −0.13 | 10 |
| H1975 | −0.34 | 50 |
| KLC1 | −0.20 | 100 |
| KLC2 | −0.14 | 100 |
| KLC3 | −0.12 | 100 |
| KLC4 | −0.03 | 100 |
| H226 | −0.08 | 10 |
| MCF7 | −0.14 | 100 |
| LS147 | −0.44 | 50 |
| HT29 | −0.64 | 5 |
| Pc3 | −0.40 | 5 |
| DU145 | −0.64 | 50 |
| QGP1 | NA | 100 |
| Capan2 | −0.81 | 50 |
| HeLa | NA | 100 |
| Saos2 | −0.32 | 50 |
| SK4SN | NA | 100 |
| Huh7 | −0.20 | 50 |

TABLE 1-continued

| Numb exon 9 inclusion values for various cell lines treated with AON1 vs. control | | |
|---|---|---|
| Cell line | DPSI | AON concentration [nM] |
| FTO-2B | NA | 100 |
| HepG2 | −0.39 | 100 |

Figure 21:
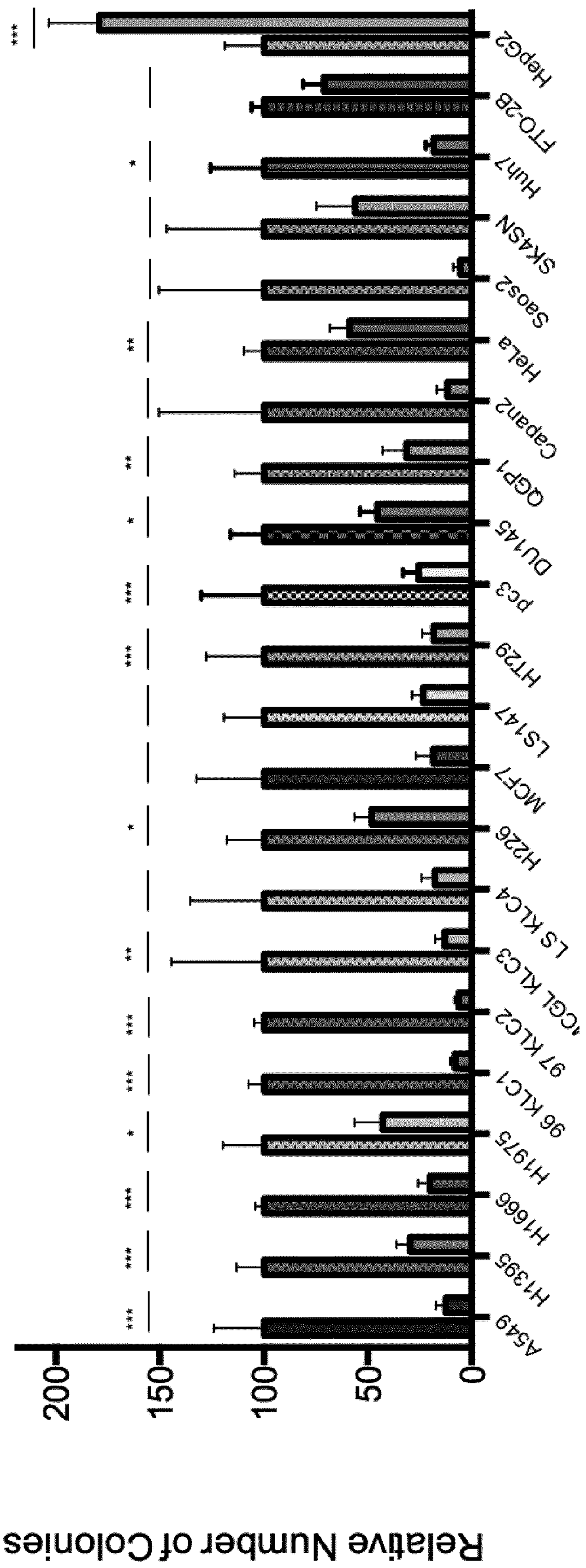
FIG. 21 shows the result of an analysis of the effect of an AON of the invention (AON1) on colony formation in different cancer cell lines.

The results shown in FIG. 21 indicate that a statistically significant reduction in the number of colonies formed upon treatment with AON1 (plain bars on FIG. 21) compared to a control oligonucleotide (Random oligonucleotide, bars with dotted fill on FIG. 21) is obtained in four different human lung adenocarcinoma (LUAD) cell lines (A549, H1395, H1666, H1975) and four different mouse LUAD cell lines (96 KLC1, 97 KLC2, MCGL KLC3, LS KLC4), at least one lung squamous cell carcinoma (LSCC) cell line (H226), at least one colon cancer cell line (HT29), two human prostate cancer cell lines (pc3, DU145), at least one pancreatic cancer cell line (QGP1), a human cervical cancer cell line (HeLa), and at least one hepatocarcinoma cell line (Huh7). A large but non statistically significant reduction of colony numbers was observed in breast cancer (MCF7), neuroblastoma (SK4SN) and osteosarcoma (Saos2), as well as pancreatic cancer cell line Capan2, colon cancer cell line LS147 and rat hepatocarcinoma cell line FTO-2B. However, the lack of statistical significance in these cell lines appears to be attributable to large variability in the control conditions for these particular samples, rather than a lack of effect of the AON of the invention. Further, the data shows that in HepG2, where NUMB is described as having a pro-tumoral activity, the treatment with AON1 has a proliferative effect. By contrast, in other hepatocarcinoma cell lines such as Huh7, where NUMB is anti-tumoral, the treatment with AON1 results in a reduction of the number of colonies.

Therefore, the data show on FIG. 21 indicates that treatment an AON according to the invention (in particular AON1, SEQ ID NO: 12) can reduce cellular proliferation in a variety of cancers, and in particular in cancers for which the NUMB protein has an antitumoral role.

Figure 22:
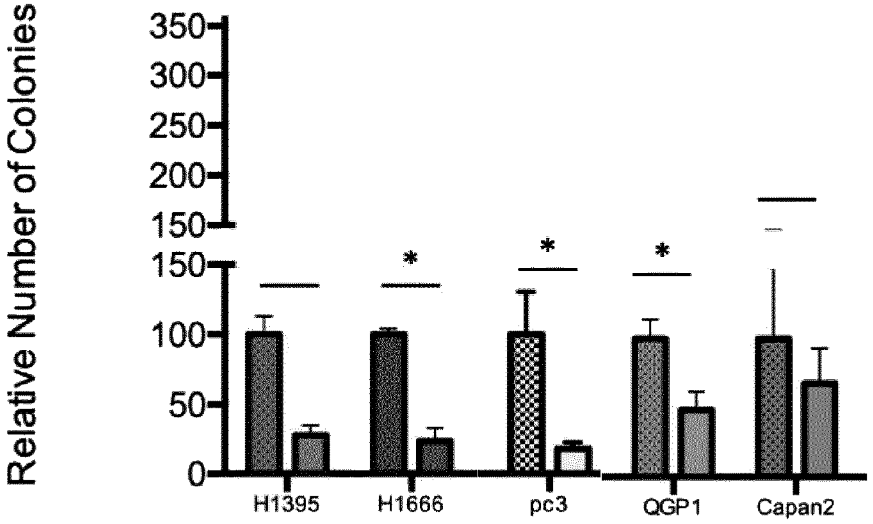
FIG. 22 shows the result of an analysis of the effect of an AON of the invention (AON6-7) on colony formation and exon 9 inclusion in different cancer cell lines.

The effect of in vitro treatment with a different AON according to the invention, in particular AON6-7 (SEQ ID NO: 24) on colony formation and exon 9 inclusion in a subset of the cancer cell lines tested above was additionally investigated, using a similar protocol. The results of these experiments are shown in FIG. 22. The data of FIG. 22 indicates that a different AON according to the invention can also reduce cell proliferation in a variety of cancer cell lines. Indeed, significant results (Student's t-test, *P-value<0.05) were obtained for H1666, pc3 and QGP1 cell lines, and large but non-statistically significant results were obtained for H1395 and Capan2 cell lines (presumably due to high variability in the control condition).

These results indicate that the AONs according to the invention may be useful in the treatment of any cancer for which NUMB protein has an antitumoral role, such as e.g. lung adenocarcinoma, lung squamous cell carcinoma, cervical cancer, breast cancer, colon cancer, prostate cancer, pancreatic cancer, osteosarcoma, neuroblastoma, and some hepatocarcinomas. Similar results are expected to be obtained with brain glioblastoma (e.g. T98G cell line), acute monocytic leukemia (e.g THP-1 cell line), as well as kidney and colorectal cancers.

Example 9: AONs According to the Invention can be Modified

The experiments above were performed using 2'-O-methyl phosphothioate-modified antisense oligonucleotides of 21 nucleotides in length. Similar effects on NUMB exon 9 splicing are expected to be obtained with AONs with lengths of between 18 and 25 nucleotides.

Further, similar effects on NUMB exon 9 splicing are expected to be obtained using AONs having different chemistries. For example, locked nucleid acids (LNAs, also known as 'inaccessible RNA') are expected to be useful in the context of the invention. In particular, the following LNAs (or AONs comprising such sequences) are expected to show an effect on NUMB exon 9 skipping: AGGCUGA (SEQ ID NO: 36), GUCAGUG (SEQ ID NO: 37), CCAUUAG (SEQ ID NO: 38), CUGAGUC (SEQ ID NO: 39), AGUGCCA (SEQ ID NO: 40), AGGCUGAGUCAGUG (SEQ ID NO: 41), GUCAGUGCCAUUAG (SEQ ID NO: 42), or AGGCUGAGUCAGUGCCAUUAG (SEQ ID NO: 44). The AONs of sequence AGGCUGAGUCAGUG (SEQ ID NO: 41) and GUCAGUGCCAUUAG (SEQ ID NO: 42) may be particularly beneficial in promoting NUMB exon 9 skipping, and the AON of sequence AGGCUGAGUCAGUGCCAUUAG (SEQ ID NO: 44) may be especially beneficial in promoting NUMB exon 9 skipping. Any DNA version of the above sequences (i.e. with Ts replacing Us) would also be expected to show an effect on exon 9 skipping, and the sequences provided above are intended to encompass such DNA versions.

Figure 15A:
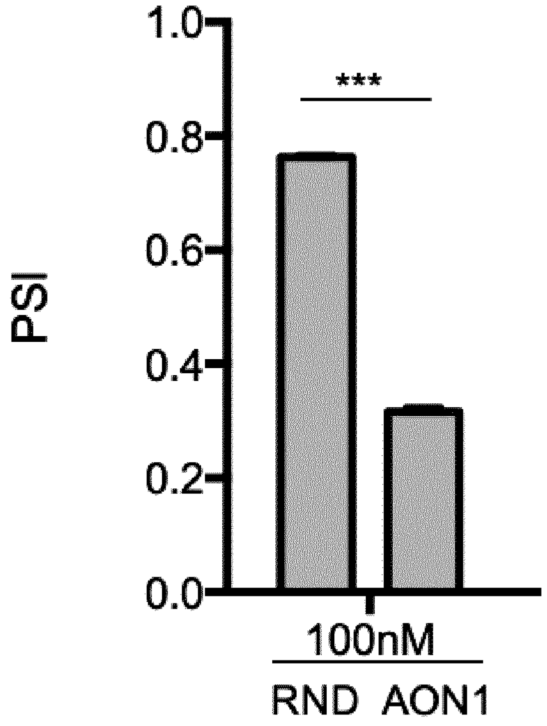
FIGS. 15A and 15B show the effect on endogenous NUMB exon 9 inclusion (FIG. 15A) and colony formation (FIG. 15B) in A549 lung adenocarcinoma cell line following transfection with an AON according to the invention alongside a control AON based on a randomised sequence of 21 nts, wherein both the AON according to the invention and the control have a modified chemistry based on a locked nucleic acid (LNA) backbone.

In order to verify this, the inventors tested whether an antisense oligonucleotide with a locked nucleic acid (LNA) backbone chemistry and the same sequence as AON1 (SEQ ID NO: 12) was capable of promoting NUMB exon 9 skipping in vitro. Technical triplicates of A549 lung adenocarcinoma cell cultures were transfected with 100 nM of: (1) an AON of sequence SEQ ID NO: 12 with a locked nucleic acid backbone; or (2) a random LNA AON of sequence SEQ ID NO: 349. The levels of endogeneous NUMB transcript with or without exon 9 were quantified by capillary electrophoresis in order to calculate the PSI in each condition. The results of these experiments are shown in FIG. 15A, where it can be seen that the modified AON is capable of significantly increasing NUMB exon 9 skipping compared to a control (random AON) condition (Students t-test, ***P-value<0.001).

Figure 15B:
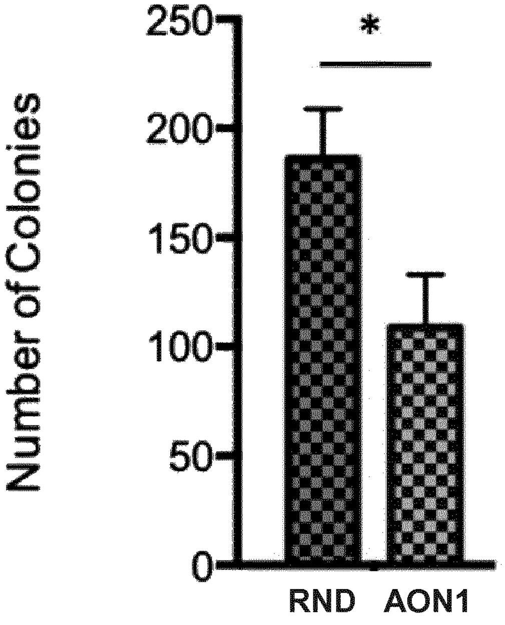

The inventors further verified that the modified AON is also capable of reducing colony formation in cancer cells. In particular, the colony formation capacity of A549 lung adenocarcinoma cell cultures transfected with 100 nM of: (1) an AON of sequence SEQ ID NO: 12 with a locked nucleic acid backbone; or (2) a random AON of sequence SEQ ID NO: 349, was tested. The results of these experiments are shown in FIG. 15B, where it can be seen that modified (LNA) AON is capable of significantly reducing the colony formation capacity of lung adenocarcinoma cells compared to a control (random AON) condition (Students t-test, *P-value<0.05).

Locked Nucleic Acids (LNAs) according to the invention may additionally have a higher affinity for their target sequence compared to a non-modified sequence of the same length. Therefore, LNAs according to the invention may be efficient repressors of NUMB exon 9 inclusion even at shorter lengths than e.g. the 21 nt AONs exemplified above. This hypothesis was tested in Example 11 below.

Further, fully 2'-O-methyl modified AONs with a phosphorothioate backbone are also expected to be useful in the medical treatments and methods of the invention. In particular, an AON with the sequence AGGCTGAGTCAGTGCCATTAG (SEQ ID NO: 43) in which all or some of the cytosine residues are methylated may be expected to show good results in NUMB exon 9 skipping and consequential therapeutic effects.

Figure 16:
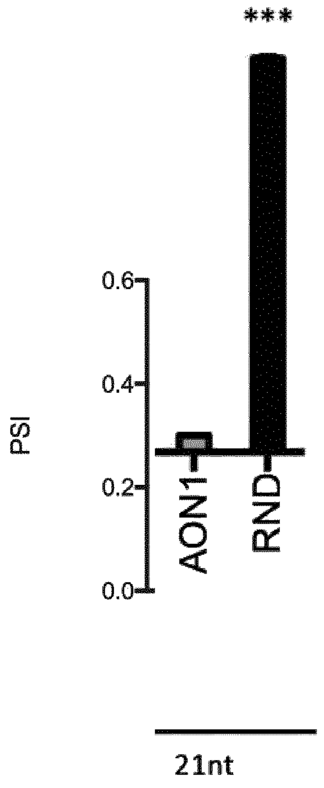
FIG. 16 shows the effect on endogenous NUMB exon 9 inclusion in a HEK-293T cell line following transfection with 100 nM of AON1, according to the invention, alongside a control AON based on a randomised sequence of 21 nts, wherein both the AON according to the invention and the control have a modified chemistry based on a 2'-O-methyl modified AON with a phosphorothioate backbone.

In order to test this, a 2'-O-methyl modified AON with a phosphorothioate backbone with the sequence of AON1 (i.e. an AON of sequence SEQ ID NO: 12) was transfected in HEK-293T cells at a concentration of 100 nM. A control condition in which a random nucleotide sequence 2'-O-methyl modified AON with a phosphorothioate backbone (SEQ ID NO: 357) was transfected in HEK-293T cells at a concentration of 100 nM was tested in parallel. Both conditions were tested in triplicates. The levels of endogeneous NUMB transcript with or without exon 9 were quantified by capillary electrophoresis in order to calculate the PSI in each condition. The results of these experiments are shown on FIG. 16, where it can be seen that the modified AON is capable of significantly increasing NUMB exon 9 skipping compared to a control (random AON) condition (Students t-test, ***P-value<0.001).

Together, these experiments show that AONs according to the invention with modified chemistries also have a beneficial effect on exon 9 skipping and reduction in colony formation, and can be expected to have similar effects in vivo as demonstrated above for the non-modified AONs.

Example 10: AONs Targeting any Part of the Region of SEQ ID NO: 305 Induce NUMB Exon 9 Skipping and Reduce Colony Formation Capacity of Lung Adenocarcinoma Cells One of the regions identified in Example 2, the region having the sequence of SEQ ID NO: 305 (targeted by AON1, AON2, AON1-2, AON2-3; i.e. SEQ ID NO: 12, 13, 19 and 20) was further studied in order to identify whether targeting specific sub-regions of this region of NUMB exon 9 leads to stronger effects on NUMB exon 9 skipping and colony formation.

In particular, very low concentrations (10 nM) of 2'O-Methyl phosphorothioated RNA with the sequence of each of AON1 (SEQ ID NO: 12), AON1-2 (SEQ ID NO: 19), AON2 (SEQ ID NO: 13), AON2-3 (SEQ ID NO: 20), and a random 2'O-Methyl phosphorothioated RNA AON (SEQ ID NO: 357) were transfected in A549 lung adenocarcinoma cells. The levels of NUMB transcript with or without exon 9 were quantified by capillary electrophoresis in order to calculate the endogeneous NUMB exon 9 PSI in each condition, and the number of colonies was counted in each condition.

Figure 17A:
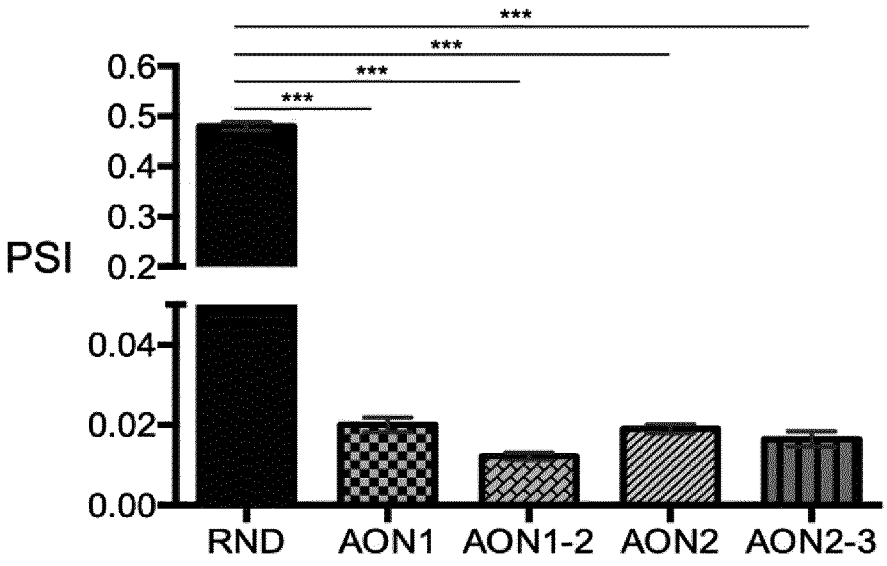
FIGS. 17A and 17B show the effect on endogenous NUMB exon 9 inclusion (FIG. 17A) and colony formation (FIG. 17B) in A549 lung adenocarcinoma cell line following transfection with various AONs according to the invention covering the region of NUMB exon 9 having the sequence of SEQ ID NO: 305, alongside a control AON based on a randomised sequence of 21 nts.
Figure 17B:
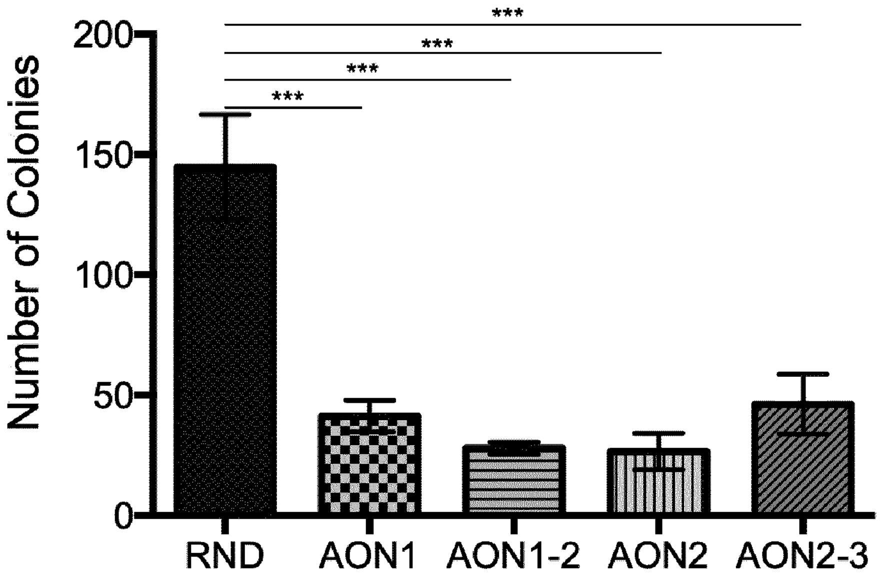

The results of these experiments are shown in FIGS. 17A (endogeneous NUMB exon 9 PSI) and 17B (colony formation), where all statistics were obtained using Student's t-test (***P-value<0.001). These results show that targeting any part of the region of sequence SEQ ID NO: 305 in exon 9 of NUMB results in significant induction of exon 9 skipping and reduction of colony formation capacity, since even at low concentrations (where any differences in potency between the different sub-areas of the region would be expected to appear more prominently) all of the sub-regions are associated with similar levels of potency. As such, the data supports the hypothesis that targeting any part of the entire region of SEQ ID NO: 305 is associated with potent inhibition of exon 9 inclusion.

Example 11: Short AONs Targeting Sub-Regions of Region 1 Induce NUMB Exon 9 Skipping In order to further characterise sub-regions within the region of SEQ ID NO: 305, and in particular within Region 1 (SEQ ID NO: 12), AONs with shorter lengths than AON1 were then produced. These were produced with a locked nucleic acid (LNA) backbone chemistry in order to simultaneously test the hypothesis that such modified AONs may be expected to have high affinity for their target even when using shorter lengths of AONs.

In particular, the inventors designed LNA AONs according to the invention, targeting the region defined by SEQ ID NO: 305 in NUMB exon 9, with lengths of 7 nucleotides, 14 and 21 nucleotides. These were transfected at a concentration of 100 nM in HEK-293T cells. A control AON (2'-O-methyl modified AON with a phosphorothioate backbone with a random sequence of SEQ ID NO: 357) was also transfected at a concentration of 100 nM in HEK-293T cells. The levels of NUMB transcript with or without exon 9 were quantified by capillary electrophoresis in order to calculate the endogeneous NUMB exon 9 PSI in each condition.

The following five 7-nucleotide LNA AONS were tested: LNA1 is an AON of sequence SEQ ID NO: 344, which targets SEQ ID NO: 59; LNA1-2 is an AON of sequence SEQ ID NO: 345, which targets SEQ ID NO: 56; LNA2 is an AON of sequence SEQ ID NO: 346, which targets SEQ ID NO: 52; LNA2-3 is an AON of sequence SEQ ID NO: 347, which targets SEQ ID NO: 49; and LNA3 is an AON of sequence SEQ ID NO: 348, which targets SEQ ID NO: 45. All of the 7 nt AONs target regions also targeted by AON1 (SEQ ID NO: 12), i.e. Region 1 of *Homo sapiens* NUMB exon 9 (SEQ ID NO: 44).

The following 14-nucleotide LNA AONS were tested: LONG1 is an AON of sequence SEQ ID NO: 339, which targets SEQ ID NO: 341; LONG2 is an AON of sequence SEQ ID NO: 340, which targets SEQ ID NO: 342. Both LONG1 and LONG2 target regions also targeted by AON1 (SEQ ID NO: 12), i.e. Region 1 of *Homo sapiens* NUMB exon 9 (SEQ ID NO: 44).

Figure 18A:
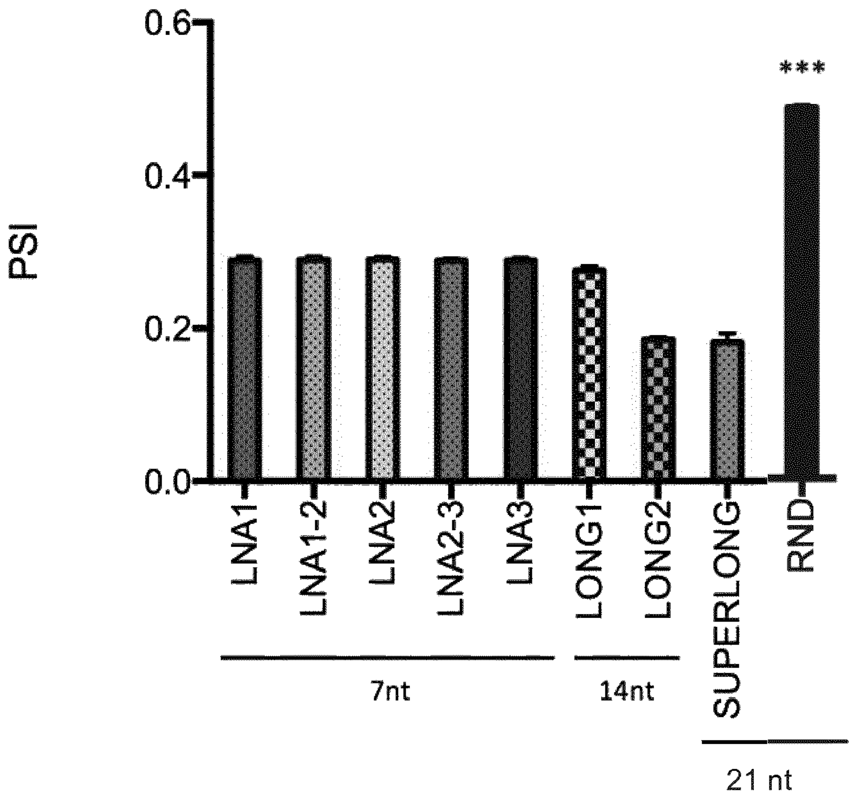
FIGS. 18A and 18B show the effect on endogenous NUMB exon 9 inclusion in HEK-293T following transfection with various AONs of various lengths according to the invention covering different parts of a specific region (Region 1) of NUMB exon 9, alongside a control AON based on a randomised sequence of 21 nts, at a concentration of 100 nM (FIG. 18A) and 1,000 nM (FIG. 18B)

Additionally, a 21 nucleotides long LNA AON with the sequence of AON1 (SEQ ID NO: 12) was also tested (referred to as "SUPERLONG" in FIG. 18A).

The results of these experiments can be seen in FIG. 18A, where all statistics are the result of Student's t-test ((*P-value<0.001). As can be seen in FIG. 18**A, all five of the short LNAs (7 nt long) resulted in similar and significant levels of exon 9 exclusion, regardless of the sub-region of the region of SEQ ID NO:12 that was targeted. Further, both of the 14 nt LNA AONs also resulted in significant levels of exon 9 skipping, which were higher than that observed using the 7 nt long AONs. LONG2 appeared to be slightly more potent than LONG1. The LNA AON of 21 nt shows the strongest effect of all constructs tested.

Figure 18B:
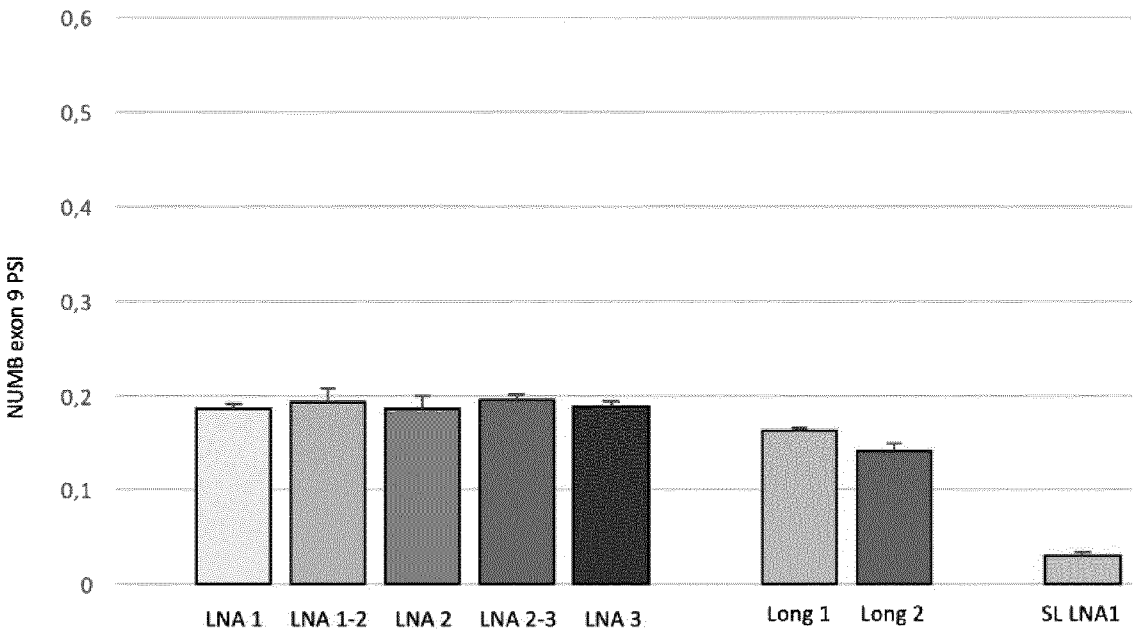

The same experiment was repeated with higher doses of each AON (1,000 nM), and the results can be seen in FIG. 18B (where SL LNA1 is the SUPERLONG LNA AON of FIG. 18A). As can be seen in FIG. 18B, increasing the dose results in slightly lower levers of exon 9 inclusion, but the same patterns as in FIG. 18A can be observed. This may indicate that either the lower concentration of 100 nM already almost saturated the system, or that the two concentrations are associated with different transfection efficacies.

The data in FIGS. 18A and 18B indicates that any sub-region of Region 1 of *Homo Sapiens* exon 9 (SEQ ID NO: 44) can be efficiently targeted by AONs as short as 7 nt, even at concentrations as low as 100 nM, at least when using LNA modified AONs.

The slight difference between LONG1 (LNA AON of SEQ ID NO: 339) and LONG2 (LNA AON of SEQ ID NO: 340) was further investigated by transfecting the constructs in A549 cells at a lower concentration of 50 nM. A comparative random LNA AON of 14 nt (SEQ ID NO: 343) was tested in parallel. The levels of NUMB transcript with or without exon 9 were quantified by capillary electrophoresis in order to calculate the endogeneous NUMB exon 9 PSI in each condition, and the number of colonies was counted in each condition.

Figure 19A:
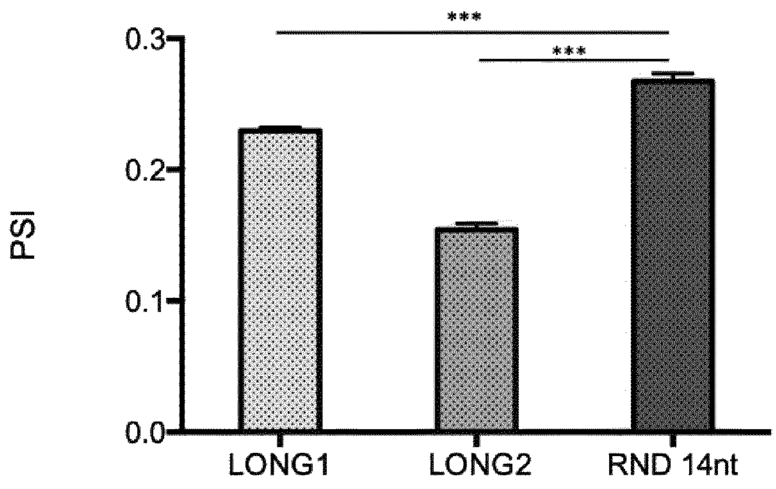
FIGS. 19A and 19B show the effect on endogenous NUMB exon 9 inclusion (FIG. 19A) and colony formation (FIG. 19B) in A549 lung adenocarcinoma cell line following transfection with two AONs according to the invention tested in FIGS. 18A and 18B, alongside a control AON based on a randomised sequence of 14 nts.
Figure 19B:
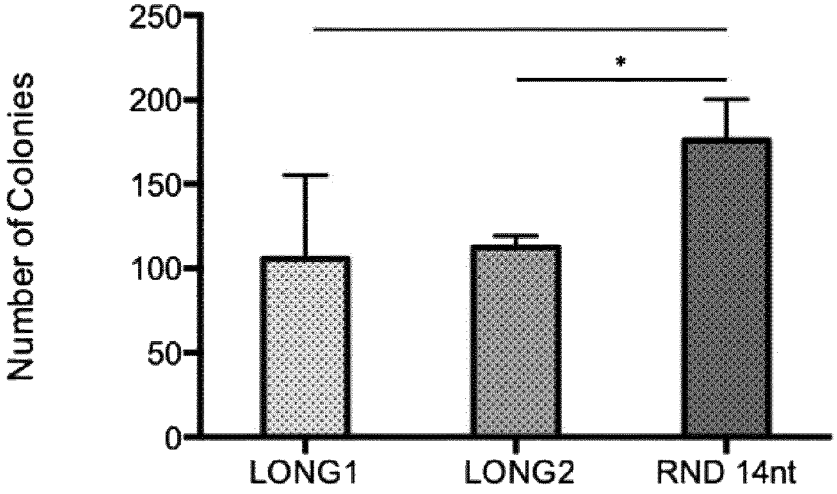

The results of these experiments are shown in FIGS. 19A (endogeneous NUMB exon 9 PSI) and 19B (colony formation), where all statistics were obtained using Student's t-test (***P-value<0.001, *P-value<0.05). This data shows that the slightly stronger effect on exon 9 inclusion seen with LONG2 compared to LONG1 in FIGS. 18A and 18B is still apparent at this lower concentration, although both constructs resulted in significant inhibition of exon 9 inclusion compared to the random control. The difference between LONG1 and LONG2 was less visible with respect to colony formation, although LONG2 appears to reduce the number of colonies in a more consistent fashion than LONG1. Together, these results indicate that the first 14 nt sequence of Region 1 (SEQ ID NO: 12) may contain regulatory elements that are particularly important in inducing exon 9 skipping. However, the data in FIGS. 18A and 18B indicates that targeting Region 1 outside of this first 14 nt sequence (see the results obtained with LNA1 and LNA1-2) still results in significant inhibition of exon 9 inclusion.

Figure 20:
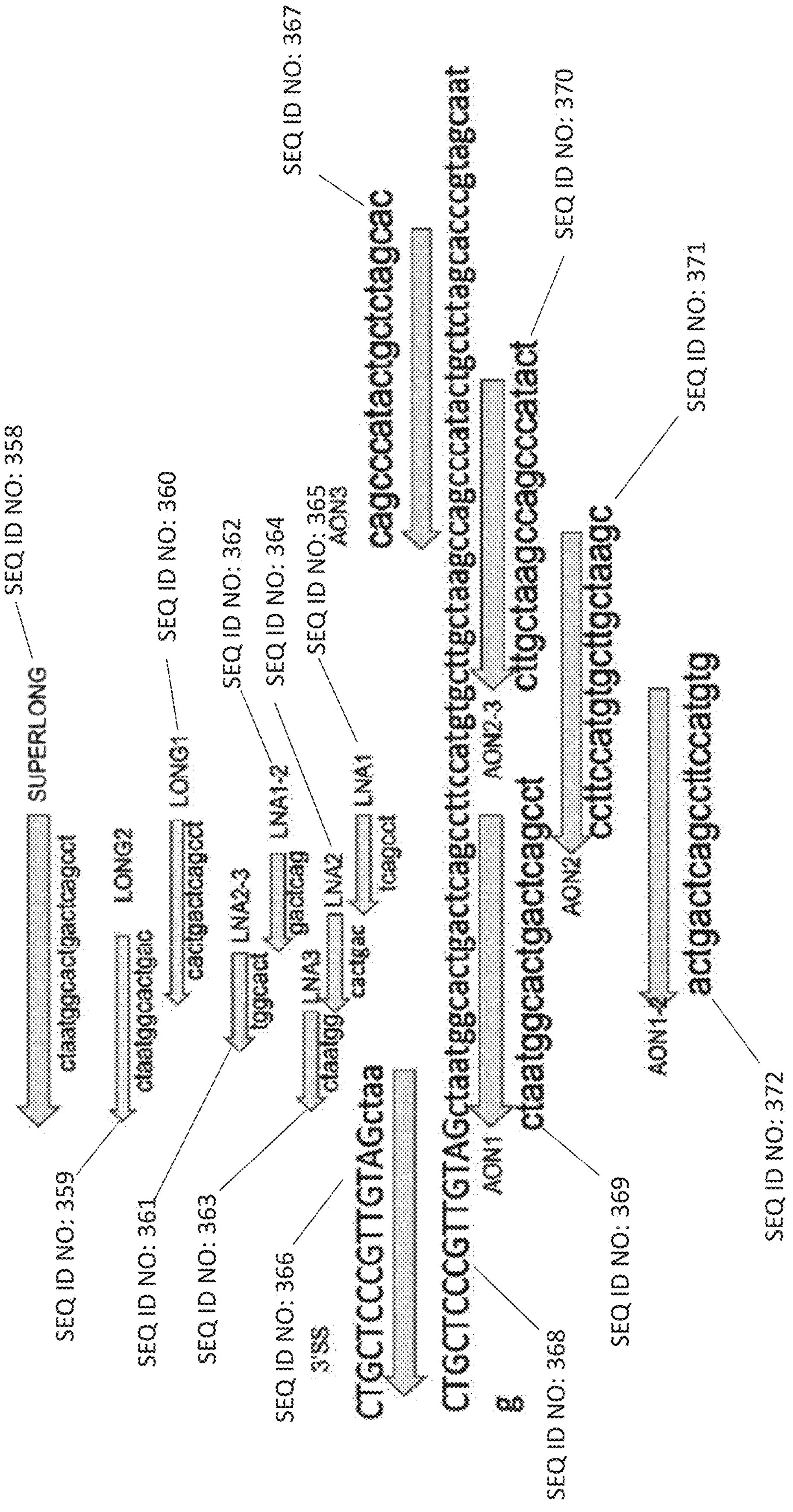
FIG. 20 shows schematically the sequences of the 3' end of exon 9 of human Numb, together with the nucleic acid binding/target sequences within the NUMB gene of the AONs tested in FIGS. 17 to 19 (SEQ ID NO: 358-372)

FIG. 20 summarises the AONs that were tested in the experiments of Examples 10 and 11, in which the naming of any AON also tested in Example 2 (as shown in FIG. 2), is consistent with the naming used in Example 2/FIG. 2.

Materials and Methods

Study of NUMB Exon 9 Inclusion in Different Tumours:

The analysis of NUMB exon 9 PSI distribution in cancer samples was derived from (Sebestyen et al. 2015). NUMB exon 9 PSI was compared across 11 different tumor types using only paired tumor/non-tumor samples from the TCGA consortium. Mann Whitney U test was used to assess differences in PSI distribution between of healthy and tumor samples; correction of multiple testing was performed with Benjamini-Hochberg.

Scanning of NUMB Exon 9 with AONS:

2'-O-methyl phosphothioate-modified antisense oligonucleotides of 21 nucleotides in length and reverse-complementary to NUMB exon 9 sequence were designed, with sequences SEQ ID NO: 12 to 24. The compounds were synthesised by Sigma-Aldrich. Two batches of AONs were ordered, one of 8 mg and one of 16 mg. AONs were ordered dry, resuspended in PBS and stored at −20° C.

A stably transformed HEK-293T cell line expressing a reporter NUMB exon 9 minigene (RG6-NUMB, (Bechara et al., 2013; Hernandez et al., 2016)) was transfected with 100 nM of individual AONs 24 hours after transfection, RNA was isolated, retro-transcribed and amplified with primers specific for detecting NUMB exon 9 inclusion/skipping in the minigene. The results of NUMB exon 9 inclusion (PSI) was calculated for three technical replicates for each AON.

Cell Culture and Transfection:

All cell lines were cultured in Dulbecco's Modified Eagle Medium (DMEM) supplemented with 10% Fetal Bovine Serum (FBS, Gibco) and antibiotics (50 units/ml penicillin and 50 ml/ml streptomycin).

Cell transfection, RNA extraction and processing (including reverse-transcription, PCR amplification and isoform quantification by capillary electrophoresis) were performed as in (Hernandez et al. 2016). PSI quantification was performed either by capillary electrophoresis (Hernandez et al. 2016) or by electrophoretic separation of the PCR products in 6% acrylamide gels. In the latter case, SyberGreen was used for band detection, images were acquired with Geldoc (Biorad) and the band quantification was performed with FIJI software (Schindelin et al., 2012).

For clonogenic assays, 20,000 mice cells were cultured in 6-well plates (2000 A549 cells) and transfected using Lipofectamine RNAiMAX (Invitrogen) with 100 nM of AONs, following the manufacturer's instructions. Cells were maintained in culture for at least 7 days, then media was removed and cells were fixed with 1 ml methanol and stained with crystal violet overnight. Afterwards, the wells were washed with water and left to dry. Colony quantification was performed using FIJI software and a custom-made R script.

Prediction of Splicing Factor Binding Sites:

SpliceAid2 web tool was used for predicting splicing factor binding sites across NUMB exon 9 (Piva et al., 2012; (http://193.206.120.249/splicing_tissue.html).

Mice Experiments:

Wild-type BL6 male mice, older than 12 weeks were used for testing the effect of AONs in vivo in healthy lungs. AONs were resuspended at a concentration of 3,100 ng/μl, and a volume of 100 μl was intratracheally administered to the mice (regardless of their weight). 3 days after the administration, mice were sacrificed and samples were collected. Tissue was disaggregated using glass-beads (Glass-beads acid-washed, 425 to 600 μm, Sigma) and a beadbeater (Mini-Beadbeater, Biospec Products), then resuspended in homogenisation buffer from Maxwell 16 LEV simple RNA tissue kit (Promega). After tissue disruption, RNA was isolated from the samples using Maxwell robot following Maxwell 16 LEV simple RNA tissue kit manufacturer's instructions.

RERTert, K-rasLSLG12V mice (Guerra et al. 2003) were used for testing the effect of AONs on tumors. 22 week old mice were injected intraperitoneally with tamoxifen (1 mg/mice) to induce tumor formation. Once tumors could be detected by micro-CT (6 to 8 months) a single administration of AON was performed (3,100 ng/μl AONs in saline buffer, 100 μl/mice) intratracheally. After 3 weeks, mice were sacrificed and tissue samples were collected. Lung tumors were micro-dissected and healthy and tumor tissues were processed in parallel as explained for healthy mice tissue (see above).

For experiments relating to tumor progression, the same mouse model (RERTert, K-rasLSLG12V mice) and protocol was used. Once mice displayed tumors, they were administered the same dose of AON once a week for two months via intranasal administration. Tumor growth was followed by micro-CT every other week for two months.

For the orthotopic mouse model, SCID-Beige mice of at least 6 weeks of age where deeply anesthesised and inoculated, intratracheally with 1,500,000 A549 cells with a plasmid encoding luciferase. One month after the inoculation the mice were monitored weekly for the detection of luminescents signal: a read out of the presence of the cancerous cells. Mice were anestesised and injected, intraperitoneally with 100 μl of luciferine (100 mg/kg concentration, resuspended in PBS), and 10 minutes later, the luminescent signal was quantified with the In Vivo Imaging System (IVIS) by Perkin Elmer®. Once the tumors were determined to have grown to a given size, mice were treated once a week with the oligonucleotide of the invention for two months. 100 μl of 3,100 ng/μl (resuspended in sterile PBS) of AON were delivered to the mice intranasally.

REFERENCES

Douglas Bates, Martin Maechler, Ben Bolker, Steve Walker (2015). Fitting Linear Mixed-Effects Models Using Ime4. Journal of Statistical Software, 67(1), 1-48.<doi: 10.18637/jss.v067.i01>

Bechara, E. G., Sebestyen, E., Bernardis, I., Eyras, E. & Valcarcel, J. (2013). RBM5, 6, and 10 Differentially Regulate NUMB Alternative Splicing to Control Cancer Cell Proliferation. *Molecular Cell,* 52(5), 720-733. doi: 10.1016/j.molcel.2013.11.010

Guerra, C., Mijimolle, N., Dhawahir, A., Dubus, P., Barradas, M., Serrano, M. & Barbacid, M. (2003). Tumor induction by an endogenous K-ras oncogene is highly dependent on cellular context. *Cancer Cell,* 4(2), 111-120.

Hernandez, J., Bechara, E., Schlesinger, D., Delgado, J., Serrano, L., & Valcarcel, J. (2016). Tumor suppressor properties of the splicing regulatory factor RBM10. *RNA biology,* 13(4), 466-472. doi:10.1080/15476286.2016.1144004

Hua, Y., Sahashi, K., Hung, G., Rigo, F., Passini, M. a., Bennett, C. F., & Krainer, A. R. (2010). Antisense correction of SMN2 splicing in the CNS rescues necrosis in a type III SMA mouse model. *Genes & Development,* 24(15), 16341644. doi:10.1101/gad.1941310

Hua, Y., Sahashi, K., Rigo, F., Hung, G., Horev, G., Bennett, C. F., & Krainer, A. R. (2011). Peripheral SMN restoration is essential for long-term rescue of a severe spinal muscular atrophy mouse model. *Nature,* 478(7367), 123-126. doi:10.1038/nature10485

Misquitta-Ali, C. M., Cheng, E., O'Hanlon, D., Liu, N., McGlade, C. J., Tsao, M. S., & Blencowe, B. J. (2011). Global profiling and molecular characterization of alternative splicing events misregulated in lung cancer. *Molecular and Cellular Biology,* 31(1), 138-150. doi: 10.1128/MCB.00709-10

Mou, T-C and Gray, D. M. (2002). The high binding affinity of phosphorothioate-modified oligomers for Ff gene 5 protein is moderated by the addition of C-5 propyne or 2'-O-methyl modifications. Nucleic Acids Research, 30(3), 749-758.

Sebestyen, E., Singh, B., Miñana, B., Pagés, A., Mateo, F., Pujana, M. A., . . . Eyras, E. (2015). Large-scale analysis of genome and transcriptome alterations in multiple tumors unveils novel cancer-relevant splicing networks. *bioRxiv,* 023010-023010. doi:10.1101/023010

Piva, F., Giulietti, M., Burini, A. B., & Principato, G. (2012). SpliceAid 2: a database of human splicing factors expression data and RNA target motifs. *Human Mutation,* 33(1), 81-85. doi: 10.1002/humu.21609

Vigevani, L., & Valcarcel, J. (2012). The spliceosome as a target of novel antitumour drugs. *Nature reviews Drug discovery,* 11(11), 847.

Westhoff B., Colaluca, I N., D'Ario G., Donzelli M., Tosoni D., Volorio S., Pelosi G., Spaggiari L., Mazzarol G., Viale G., Pece S., & Di Fiore PP (2009). Alterations of the Notch pathway in lung cancer. Proc Natl Acad Sci USA.; 106(52):22293-8. doi: 10.1073/pnas.0907781106.

Xie, C., Lu, Z., Liu, G., Fang, Y., Liu, J., Huang, Z. & Zhang, Y. (2015). Numb downregulation suppresses cell growth and is associated with a poor prognosis of human hepatocellular carcinoma. International journal of molecular medicine, 36(3), 653-660.

Zong, F. Y., Fu, X., Wei, W. J., Luo, Y. G., Heiner, M., Cao, L. J., Hui, J. (2014). The RNA-Binding Protein QKI Suppresses Cancer-Associated Aberrant Splicing. *PLoS Genetics,* 10(4). doi:10.1371/journal.pgen.1004289

SEQUENCES

In the antisense oligonucleotide sequences provided, any U can be read as a T in alternative embodiments which are explicitly intended to be encompassed within the scope of the claimed invention.

| SEQ ID NO: | Sequence Type | Sequence |
|---|---|---|
| 1 | Mouse NUMB exon 9 (NM_001136075.2 - Numb mRNA transcript variant 1 - 1115 . . . 1261) | ctaatggcac tgactcagcc tcccatgtgc ttactgctaa gccagccaata ctgctctagc acacgtagca atgcctgtcc gtgaaaccaa cccctgggcc catgtccctg atgctgctaa caaggaaatt gcagccatac atccgg |
| 2 | Human NUMB exon 9 (NM_001005743 - Numb mRNA transcript variant 1 - 1417 . . . 1560) | ctaatggcac tgactcagcc ttccatgtgc ttgctaagcc agcccatact gctctagcac ccgtagcaat gcctgtgcgt gaaaccaacc cttgggccca tgcccctgat gctgctaacaa ggaaattgca gccacatgtt cgg |
| 44 | Region 1 of *Homo sapiens* Numb exon 9 (targeted by AON1 - SEQ ID NO: 12) | CUAAUGGCACUGACUCAGCCU |
| 3 | Region 2 of *Homo sapiens* Numb exon 9 (targeted by AON2 - SEQ ID NO: 13) | CCUUCCAUGUGCUUGCUAAGC |
| 4 | Region 3 of *Homo sapiens* Numb exon 9 (targeted by AON3 - SEQ ID NO: 14) | CAGCCCAUACUGCUCUAGCAC |
| 5 | Region 4 of *Homo sapiens* Numb exon 9 (targeted by AON4 - SEQ ID NO: 15) | CCGUAGCAAUGCCUGUGCGUG |
| 6 | Region 5 of *Homo sapiens* Numb exon 9 (targeted by AON5 - SEQ ID NO: 16) | AAACCAACCCUUGGGCCCAUG |
| 7 | Region 6 of *Homo sapiens* Numb exon 9 (targeted by AON6 - SEQ ID NO: 17) | CCCCUGAUGCUGCUAACAAGG |
| 8 | Region 7 of *Homo sapiens* Numb exon 9 (targeted by AON7 - SEQ ID NO: 18) | AAAUUGCAGCCACAUGUUCGG |
| 9 | Region 1 + 2 of *Homo sapiens* Numb exon 9 (targeted by AON1 - SEQ ID NO: 12; AON2 - SEQ ID NO: 13; and AON1-2 - SEQ ID NO: 19) | CUAAUGGCACUGACUCAGCCUUCCAUGU GCUUGCUAAGC |

-continued

| SEQ ID NO: | Sequence Type | Sequence |
|---|---|---|
| 10 | Region 4 + 5 of *Homo sapiens* Numb exon 9 (targeted by AON4 - SEQ ID NO: 15; AON5 - SEQ ID NO: 16; and AON4-5 - SEQ ID NO: 22) | CCGUAGCAAUGCCUGUGCGUGAAACCAA CCCUUGGGCCCAUG |
| 11 | Region 6 + 7 of *Homo sapiens* Numb exon 9 (targeted by AON6 - SEQ ID NO: 17; AON7 - SEQ ID NO: 18 and AON6-7 - SEQ ID NO: 24) | CCCCUGAUGCUGCUAACAAGGAAAUUGC AGCCACAUGUUCGG |
| 12 | Antisense oligonucleotide targeting Region 1 of *Homo sapiens* Numb exon 9 (AON1) | AGGCUGAGUCAGUGCCAUUAG |
| 13 | Antisense oligonucleotide targeting Region 2 of Homo sapiens Numb exon 9 (AON2) | GCUUAGCAAGCACAUGGAAGG |
| 14 | Antisense oligonucleotide targeting Region 3 of *Homo sapiens* Numb exon 9 (AON3) | GUGCUAGAGCAGUAUGGGCUG |
| 15 | Antisense oligonucleotide targeting Region 4 of *Homo sapiens* Numb exon 9 (AON4) | CACGCACAGGCAUUGCUACGG |
| 16 | Antisense oligonucleotide targeting Region 5 of *Homo sapiens* Numb exon 9 (AON5) | CAUGGGCCCAAGGGUUGGUUU |
| 17 | Antisense oligonucleotide targeting Region 6 of *Homo sapiens* Numb exon 9 (AON6) | CCUUGUUAGCAGCAUCAGGGG |
| 18 | Antisense oligonucleotide targeting Region 7 of *Homo sapiens* Numb exon 9 (AON7) | CCGAACAUGUGGCUGCAAUUU |
| 19 | Antisense oligonucleotide targeting Region 1-2 of *Homo sapiens* Numb exon 9 (AON1-2) | CACAUGGAAGGCUGAGUCAGU |
| 20 | Antisense oligonucleotide targeting Region 2-3 of *Homo sapiens* Numb exon 9 (AON2-3) | AGUAUGGGCUGGCUUAGCAAG |
| 21 | Antisense oligonucleotide targeting Region 3-4 of *Homo sapiens* Numb exon 9 (AON3-4) | CAUUGCUACGGGUGCUAGAGC |
| 22 | Antisense oligonucleotide targeting Region 4-5 of *Homo sapiens* Numb exon 9 (AON4-5) | AGGGUUGGUUUCACGCACAGG |
| 23 | Antisense oligonucleotide targeting Region 5-6 of *Homo sapiens* Numb exon 9 (AON5-6) | AGCAUCAGGGGCAUGGGCCCA |
| 24 | Antisense oligonucleotide targeting Region 6-7 of *Homo sapiens* Numb exon 9 (AON6-7) | GGCUGCAAUUUCCUUGUUAGC |
| 25 | Antisense oligonucleotide targeting the 5' splice site of Numb exon 9 | AUCUGUGGCCACCUUACCCGA |
| 26 | Antisense oligonucleotide targeting the 3' splice site of *Homo sapiens* Numb exon 9 | UUAGCUACAACGGGAGCAGAC |
| 27 | *Homo sapiens* Numb exon 9 sequence targeted by antisense oligonucleotide of SEQ. ID NO: 25 | UCGGGUAAGGUGGCCACAGAU |
| 28 | *Homo sapiens* Numb exon 9 sequence targeted by antisense oligonucleotide of SEQ. ID NO: 26 | GTCTGCTCCCGTTGTAGCTAA |
| 29 | Antisense oligonucleotide targeting the branching point of *Homo sapiens* Numb exon 9 | CAACAUCAAUGGAGUUAAUUCAU |
| 30 | Region of *Homo sapiens* Numb exon 9 targeted by SEQ. ID NO: 19 (AON1-2) | ACUGACUCAGCCUUCCAUGUG |
| 31 | Region of *Homo sapiens* Numb exon 9 targeted by SEQ. ID NO: 22 (AON4-5) | CCUGUGCGUGAAACCAACCCU |
| 32 | Region of *Homo sapiens* Numb exon 9 targeted by SEQ. ID NO: 24 (AON6-7) | GCUAACAAGGAAAUUGCAGCC |
| 33 | Region of *Homo sapiens* Numb exon 9 targeted by SEQ. ID NO: 20 (AON2-3) | CUUGCUAAGCCAGCCCAUACU |

-continued

| SEQ ID NO: | Sequence Type | Sequence |
|---|---|---|
| 34 | Region of *Homo sapiens* Numb exon 9 targeted by SEQ. ID NO: 21 (AON3-4) | GCUCUAGCACCCGUAGCAAUG |
| 35 | Region of *Homo sapiens* Numb exon 9 targeted by SEQ. ID NO: 23 (AON5-6) | UGGGCCCAUGCCCCUGAUGCU |
| 36 | Antisense oligonucleotide targeting Region 1 of *Homo sapiens* Numb exon 9 | AGGCUGA |
| 37 | Antisense oligonucleotide targeting Region 1 of *Homo sapiens* Numb exon 9 | GUCAGUG |
| 38 | Antisense oligonucleotide targeting Region 1 of *Homo sapiens* Numb exon 9 | CCAUUAG |
| 39 | Antisense oligonucleotide targeting Region 1-2 of *Homo sapiens* Numb exon 9 | CUGAGUC |
| 40 | Antisense oligonucleotide targeting Region 2-3 of *Homo sapiens* Numb exon 9 | AGUGCCA |
| 41 | Antisense oligonucleotide targeting Region 1 of *Homo sapiens* Numb exon 9 | AGGCUGAGUCAGUG |
| 42 | Antisense oligonucleotide targeting Region 1 of *Homo sapiens* Numb exon 9 | GUCAGUGCCAUUAG |
| 43 | Antisense oligonucleotide targeting Region 1 of *Homo sapiens* Numb exon 9 | AGGC$^{Me}$UGAGUC$^{Me}$AGUGC$^{Me}$C$^{Me}$AUUAG |
| 45-77 | Target regions in Region 1 + 2 of *Homo sapiens* Numb exon 9 | CUAAUGG<br>UAAUGGC<br>AAUGGCA<br>AUGGCAC<br>UGGCACU<br>GGCACUG<br>GCACUGA<br>CACUGAC<br>ACUGACU<br>CUGACUC<br>UGACUCA<br>GACUCAG<br>ACUCAGC<br>CUCAGCC<br>UCAGCCU<br>CAGCCUU<br>AGCCUUC<br>GCCUUCC<br>CCUUCCA<br>CUUCCAU<br>UUCCAUG<br>UCCAUGU<br>CCAUGUG<br>CAUGUGC<br>AUGUGCU<br>UGUGCUU<br>GUGCUUG<br>UGCUUGC<br>GCUUGCU<br>CUUGCUA<br>UUGCUAA<br>UGCUAAG<br>GCUAAGC |
| 78-104 | Target regions in Region 1 + 2 of *Homo sapiens* Numb exon 9 | CUAAUGGCACUGA<br>UAAUGGCACUGAC<br>AAUGGCACUGACU<br>AUGGCACUGACUC<br>UGGCACUGACUCA<br>GGCACUGACUCAG<br>GCACUGACUCAGC<br>CACUGACUCAGCC<br>ACUGACUCAGCCU<br>CUGACUCAGCCUU<br>UGACUCAGCCUUC |

-continued

| SEQ ID NO: | Sequence Type | Sequence |
|---|---|---|
| | | GACUCAGCCUUCC<br>ACUCAGCCUUCCA<br>CUCAGCCUUCCAU<br>UCAGCCUUCCAUG<br>CAGCCUUCCAUGU<br>AGCCUUCCAUGUG<br>GCCUUCCAUGUGC<br>CCUUCCAUGUGCU<br>CUUCCAUGUGCUU<br>UUCCAUGUGCUUG<br>UCCAUGUGCUUGC<br>CCAUGUGCUUGCU<br>CAUGUGCUUGCUA<br>AUGUGCUUGCUAA<br>UGUGCUUGCUAAG<br>GUGCUUGCUAAGC |
| 105-123 | Target regions in Region 1 + 2 of *Homo sapiens* Numb exon 9 | CUAAUGGCACUGACUCAGCCU<br>UAAUGGCACUGACUCAGCCUU<br>AAUGGCACUGACUCAGCCUUC<br>AUGGCACUGACUCAGCCUUCC<br>UGGCACUGACUCAGCCUUCCA<br>GGCACUGACUCAGCCUUCCAU<br>GCACUGACUCAGCCUUCCAUG<br>CACUGACUCAGCCUUCCAUGU<br>ACUGACUCAGCCUUCCAUGUG<br>CUGACUCAGCCUUCCAUGUGC<br>UGACUCAGCCUUCCAUGUGCU<br>GACUCAGCCUUCCAUGUGCUU<br>ACUCAGCCUUCCAUGUGCUUG<br>CUCAGCCUUCCAUGUGCUUGC<br>UCAGCCUUCCAUGUGCUUGCU<br>CAGCCUUCCAUGUGCUUGCUA<br>AGCCUUCCAUGUGCUUGCUAA<br>GCCUUCCAUGUGCUUGCUAAG<br>CCUUCCAUGUGCUUGCUAAGC |
| 124-159 | Target regions in Region 4 + 5 of *Homo sapiens* Numb exon 9 | CCGUAGC<br>CGUAGCA<br>GUAGCAA<br>UAGCAAU<br>AGCAAUG<br>GCAAUGC<br>CAAUGCC<br>AAUGCCU<br>AUGCCUG<br>UGCCUGU<br>GCCUGUG<br>CCUGUGC<br>CUGUGCG<br>UGUGCGU<br>GUGCGUG<br>UGCGUGA<br>GCGUGAA<br>CGUGAAA<br>GUGAAAC<br>UGAAACC<br>GAAACCA<br>AAACCAA<br>AACCAAC<br>ACCAACC<br>CCAACCC<br>CAACCCU<br>AACCCUU<br>ACCCUUG<br>CCCUUGG<br>CCUUGGG<br>CUUGGGC<br>UUGGGCC<br>UGGGCCC<br>GGGCCCA<br>GGCCCAU<br>GCCCAUG |

-continued

| SEQ ID NO: | Sequence Type | Sequence |
|---|---|---|
| 160-189 | Target regions in Region 4 + 5 of *Homo sapiens* Numb exon 9 | CCGUAGCAAUGCC<br>CGUAGCAAUGCCU<br>GUAGCAAUGCCUG<br>UAGCAAUGCCUGU<br>AGCAAUGCCUGUG<br>GCAAUGCCUGUGC<br>CAAUGCCUGUGCG<br>AAUGCCUGUGCGU<br>AUGCCUGUGCGUG<br>UGCCUGUGCGUGA<br>GCCUGUGCGUGAA<br>CCUGUGCGUGAAA<br>CUGUGCGUGAAAC<br>UGUGCGUGAAACC<br>GUGCGUGAAACCA<br>UGCGUGAAACCAA<br>GCGUGAAACCAAC<br>CGUGAAACCAACC<br>GUGAAACCAACCC<br>UGAAACCAACCCU<br>GAAACCAACCCUU<br>AAACCAACCCUUG<br>AACCAACCCUUGG<br>ACCAACCCUUGGG<br>CCAACCCUUGGGC<br>CAACCCUUGGGCC<br>AACCCUUGGGCCC<br>ACCCUUGGGCCCA<br>CCCUUGGGCCCAU<br>CCUUGGGCCCAUG |
| 190-211 | Target regions in Region 4 + 5 of *Homo sapiens* Numb exon 9 | CCGUAGCAAUGCCUGUGCGUG<br>CGUAGCAAUGCCUGUGCGUGA<br>GUAGCAAUGCCUGUGCGUGAA<br>UAGCAAUGCCUGUGCGUGAAA<br>AGCAAUGCCUGUGCGUGAAAC<br>GCAAUGCCUGUGCGUGAAACC<br>CAAUGCCUGUGCGUGAAACCA<br>AAUGCCUGUGCGUGAAACCAA<br>AUGCCUGUGCGUGAAACCAAC<br>UGCCUGUGCGUGAAACCAACC<br>GCCUGUGCGUGAAACCAACCC<br>CCUGUGCGUGAAACCAACCCU<br>CUGUGCGUGAAACCAACCCUU<br>UGUGCGUGAAACCAACCCUUG<br>GUGCGUGAAACCAACCCUUGG<br>UGCGUGAAACCAACCCUUGGG<br>GCGUGAAACCAACCCUUGGGC<br>CGUGAAACCAACCCUUGGGCC<br>GUGAAACCAACCCUUGGGCCC<br>UGAAACCAACCCUUGGGCCCA<br>GAAACCAACCCUUGGGCCCAU<br>AAACCAACCCUUGGGCCCAUG |
| 212-247 | Target regions in Region 6 + 7 of *Homo sapiens* Numb exon 9 | CCCCUGA<br>CCCUGAU<br>CCUGAUG<br>CUGAUGC<br>UGAUGCU<br>GAUGCUG<br>AUGCUGC<br>UGCUGCU<br>GCUGCUA<br>CUGCUAA<br>UGCUAAC<br>GCUAACA<br>CUAACAA<br>UAACAAG<br>AACAAGG<br>ACAAGGA<br>CAAGGAA<br>AAGGAAA<br>AGGAAAU<br>GGAAAUU |

-continued

| SEQ ID NO: | Sequence Type | Sequence |
|---|---|---|
| | | GAAAUUG<br>AAAUUGC<br>AAUUGCA<br>AUUGCAG<br>UUGCAGC<br>UGCAGCC<br>GCAGCCA<br>CAGCCAC<br>AGCCACA<br>GCCACAU<br>CCACAUG<br>CACAUGU<br>ACAUGUU<br>CAUGUUC<br>AUGUUCG<br>UGUUCGG |
| 248-277 | Target regions in Region 6 + 7 of *Homo sapiens* Numb exon 9 | CCCCUGAUGCUGC<br>CCCUGAUGCUGCU<br>CCUGAUGCUGCUA<br>CUGAUGCUGCUAA<br>UGAUGCUGCUAAC<br>GAUGCUGCUAACA<br>AUGCUGCUAACAA<br>UGCUGCUAACAAG<br>GCUGCUAACAAGG<br>CUGCUAACAAGGA<br>UGCUAACAAGGAA<br>GCUAACAAGGAAA<br>CUAACAAGGAAAU<br>UAACAAGGAAAUU<br>AACAAGGAAAUUG<br>ACAAGGAAAUUGC<br>CAAGGAAAUUGCA<br>AAGGAAAUUGCAG<br>AGGAAAUUGCAGC<br>GGAAAUUGCAGCC<br>GAAAUUGCAGCCA<br>AAAUUGCAGCCAC<br>AAUUGCAGCCACA<br>AUUGCAGCCACAU<br>UUGCAGCCACAUG<br>UGCAGCCACAUGU<br>GCAGCCACAUGUU<br>CAGCCACAUGUUC<br>AGCCACAUGUUCG<br>GCCACAUGUUCGG |
| 278-299 | Target regions in Region 6 + 7 of *Homo sapiens* Numb exon 9 | CCCCUGAUGCUGCUAACAAGG<br>CCCUGAUGCUGCUAACAAGGA<br>CCUGAUGCUGCUAACAAGGAA<br>CUGAUGCUGCUAACAAGGAAA<br>UGAUGCUGCUAACAAGGAAAU<br>GAUGCUGCUAACAAGGAAAUU<br>AUGCUGCUAACAAGGAAAUUG<br>UGCUGCUAACAAGGAAAUUGC<br>GCUGCUAACAAGGAAAUUGCA<br>CUGCUAACAAGGAAAUUGCAG<br>UGCUAACAAGGAAAUUGCAGC<br>GCUAACAAGGAAAUUGCAGCC<br>CUAACAAGGAAAUUGCAGCCA<br>UAACAAGGAAAUUGCAGCCAC<br>AACAAGGAAAUUGCAGCCACA<br>ACAAGGAAAUUGCAGCCACAU<br>CAAGGAAAUUGCAGCCACAUG<br>AAGGAAAUUGCAGCCACAUGU<br>AGGAAAUUGCAGCCACAUGUU<br>GGAAAUUGCAGCCACAUGUUC<br>GAAAUUGCAGCCACAUGUUCG<br>AAAUUGCAGCCACAUGUUCGG |
| 300 | Potential binding site of SF1/BBP in NUMB exon 9 | GGCACTGACTC |

-continued

| SEQ ID NO: | Sequence Type | Sequence |
|---|---|---|
| 301 | RG6-NUMB minigene WT | GGCACTGACTC |
| 302 | RG6-NUMB minigene Mut3 | GGCACTCACCTC |
| 303 | RG6-NUMB minigene Mut 4 | GGCACCGACTC |
| 304 | RG6-NUMB minigene Mut 1 | GGTACTGACCTC |
| 305 | Region 1 + 2 + 2-3 of *Homo sapiens* Numb exon 9 (targeted by by AON1 - SEQ ID NO: 12; AON2 SEQ ID NO: 13; AON1-2 - SEQ ID NO: 19; and AON2-3 - SEQ ID NO: 20) | CUAAUGGCACUGACUCAGCCUUCCAUGU GCUUGCUAAGCCAGCCCAUACU |
| 306-316 | Target regions in Region 1 + 2 + 2-3 of *Homo sapiens* Numb exon 9 | SEQ ID NO: 45-77<br>CUAAGCC<br>UAAGCCA<br>AAGCCAG<br>AGCCAGC<br>GCCAGCC<br>CCAGCCC<br>CAGCCCA<br>AGCCCAU<br>GCCCAUA<br>CCCAUAC<br>CCAUACU |
| 317-327 | Target regions in Region 1 + 2 + 2-3 of *Homo sapiens* Numb exon 9 | SEQ ID NO: 78-104<br>UGCUUGCUAAGCC<br>GCUUGCUAAGCCA<br>CUUGCUAAGCCAG<br>UUGCUAAGCCAGC<br>UGCUAAGCCAGCC<br>GCUAAGCCAGCCC<br>CUAAGCCAGCCCA<br>UAAGCCAGCCCAU<br>AAGCCAGCCCAUA<br>AGCCAGCCCAUAC<br>GCCAGCCCAUACU |
| 328-338 | Target regions in Region 1 + 2 + 2-3 of *Homo sapiens* Numb exon 9 | SEQ ID NO:105-123<br>CUUCCAUGUGCUUGCUAAGCC<br>UUCCAUGUGCUUGCUAAGCCA<br>UCCAUGUGCUUGCUAAGCCAG<br>CCAUGUGCUUGCUAAGCCAGC<br>CAUGUGCUUGCUAAGCCAGCC<br>AUGUGCUUGCUAAGCCAGCCC<br>UGUGCUUGCUAAGCCAGCCCA<br>GUGCUUGCUAAGCCAGCCCAU<br>UGCUUGCUAAGCCAGCCCAUA<br>GCUUGCUAAGCCAGCCCAUAC<br>CUUGCUAAGCCAGCCCAUACU |
| 339 | Antisense oligonucleotide targeting Region 1 of *Homo sapiens* Numb exon 9 - 14 nt long, targeting second part of region defined by SEQ ID NO: 44 | AGGCUGAGUCAGUG |
| 340 | Antisense oligonucleotide targeting Region 1 of *Homo sapiens* Numb exon 9 - 14 nt long, targeting first part of region defined by SEQ ID NO: 44 | GUCAGUGCCAUUAG |
| 341 | *Homo sapiens* Numb exon 9 sequence targeted by antisense oligonucleotide of SEQ ID NO: 339 | CACUGACUCAGCCU |
| 342 | *Homo sapiens* Numb exon 9 sequence targeted by antisense oligonucleotide of SEQ ID NO: 340 | CUAAUGGCACUGAC |
| 343 | Random oligonucleotide - 14 nt long | AAACCGCGCGUACG |
| 344 | Antisense oligonucleotide targeting SEQ ID NO: 59 in Region 1 of *Homo sapiens* Numb exon 9 - 7 nt long | AGGCUGA |

-continued

| SEQ ID NO: | Sequence Type | Sequence |
|---|---|---|
| 345 | Antisense oligonucleotide targeting SEQ ID NO: 56 in Region 1 of *Homo sapiens* Numb exon 9 - 7 nt long | CUGAGUC |
| 346 | Antisense oligonucleotide targeting SEQ ID NO: 52 in Region 1 of *Homo sapiens* Numb exon 9 - 7 nt long | GUCAGUG |
| 347 | Antisense oligonucleotide targeting SEQ ID NO: 49 in Region 1 of *Homo sapiens* Numb exon 9 - 7 nt long | AGUGCCA |
| 348 | Antisense oligonucleotide targeting SEQ ID NO: 45 in Region 1 of *Homo sapiens* Numb exon 9 - 7 nt long | CCAUUAG |
| 349 | Random oligonucleotide - 21 nt long | AACCGCGCGUACGAAACCGUC |
| 350 | Antisense oligonucleotide targeting SEQ ID NO: 117 in Region 1 + 2 + 2-3 of *Homo sapiens* Numb exon 9 - 21 nt long | CAAGCACAUGGAAGGCUGAGU |
| 351 | Antisense oligonucleotide targeting SEQ ID NO: 121 in Region 1 + 2 + 2-3 of *Homo sapiens* Numb exon 9 - 21 nt long | UUAGCAAGCACAUGGAAGGCU |
| 352 | Antisense oligonucleotide targeting SEQ ID NO: 331 in Region 1 + 2 + 2-3 of *Homo sapiens* Numb exon 9 - 21 nt long | GCUGGCUUAGCAAGCACAUGG |
| 353 | Antisense oligonucleotide targeting SEQ ID NO: in Region 2 + 3 of *Homo sapiens* Numb exon 9 - 21 nt long | GAGCAGUAUGGGCUGGCUUAG |
| 354 | Region of *Homo sapiens* Numb exon 9 targeted by SEQ ID NO: 353 | CUAAGCCAGCCCAUACUGCUC |
| 355 | Antisense oligonucleotide targeting a in Region 2 + 3 of *Homo sapiens* Numb exon 9 - 21 nt long | GCUAGAGCAGUAUGGGCUGGC |
| 356 | Region of *Homo sapiens* Numb exon 9 targeted by SEQ ID NO: 355 | GCCAGCCCAUACUGCUCUAGC |
| 357 | 21 nt random oligonucleotide, 2'-O-Methyl Phosphorothioated | UGAUUCGUGCGGCGCGUAUAU |

The invention claimed is:

1. A method of treating a proliferative disease in a subject in need thereof, the method comprising administering to the subject an antisense oligonucleotide comprising at least 7 nucleotides that is complementary to a target region within NUMB exon 9, wherein the target region within NUMB exon 9 is comprised within a sequence selected from the group consisting of SEQ ID NO: 305, SEQ ID NO: 10, SEQ ID NO: 32, and SEQ ID NO: 35.

2. The method of claim 1, wherein the proliferative disease is a disease in which NUMB protein acts as an antitumor agent.

3. The method of claim 1, wherein the proliferative disease is lung adenocarcinoma, non-small cell lung cancer, lung small cell carcinoma, lung squamous cell carcinoma, cervical cancer, breast cancer, pancreatic cancer, prostate cancer, hepatocarcinoma, osteosarcoma, neuroblastoma, or colon cancer.

4. The method of claim 1, wherein the subject has a cancer or tumour and the method comprises delivering the oligonucleotide to the site of the cancer or the tumour.

5. The method of claim 4, wherein the subject has lung cancer and the method comprises delivering the oligonucleotide through the respiratory system.

6. The method of claim 1, wherein the method comprises injecting a composition comprising the oligonucleotide intravenously.

7. The method of claim 3 wherein the method comprises testing a tissue sample obtained from the subject for elevated levels of NUMB exon 9 inclusion compared to a healthy control.

8. The method of claim 1, wherein the antisense oligonucleotide comprises a nucleotide sequence that is complementary to a target region comprising at least 13 nucleotides of NUMB exon 9.

9. The method of claim 1, wherein the antisense oligonucleotide comprises a nucleotide sequence that is complementary to a target region comprising from 7 to 25 nucleotides of NUMB exon 9.

10. The method of claim 1, wherein the oligonucleotide comprises from 7 to 31 nucleotides.

11. The method of claim 1, wherein the oligonucleotide does not comprise a sequence that is complementary to a 5' and/or 3' exon-intron junction of NUMB exon 9.

12. The method of claim 1, wherein the oligonucleotide is an RNA or modified RNA molecule, a DNA or modified DNA molecule, or a mixture of native or modified RNA and native or modified DNA.

13. The method of claim 1, wherein the oligonucleotide comprises from 7 to 15 nucleotides, and wherein the oligonucleotide is a locked nucleic acid.

14. The method of claim 1, wherein the oligonucleotide comprises from 18 to 25 nucleotides, and wherein the oligonucleotide is a 2'-O-methyl phosphorothioate ribonucleic acid or a 2'-O-methoxyethyl-modified phosphorothioate ribonucleic acid.

15. The method of claim 1, wherein at least one cytosine residue within the oligonucleotide is methylated.

16. The method of claim 1, wherein the oligonucleotide comprises a sequence selected from:

(a) AGGCUGA (SEQ ID NO: 36), GUCAGUG (SEQ ID NO: 37), CCAUUAG (SEQ ID NO: 38), CUGAGUC (SEQ ID NO: 39), or AGUGCCA (SEQ ID NO: 40); and/or, (b) AGGCUGAGUCAGUG (SEQ ID NO: 41), or GUCAGUGCCAUUAG (SEQ ID NO: 42); and/or, (c) AGGCUGAGUCAGUGCCAUUAG (SEQ ID NO: 43) or AGGCUGAGUCAGUGCCAUUAG (SEQ ID NO: 12); and/or (d) AGGGUUGGUUUCACGCACAGG (SEQ ID NO: 22) or GGCUGCAAUUUCCUUGUUAGC (SEQ ID NO: 24).

17. The method of claim 1, wherein the target region within NUMB exon 9 is comprised within a sequence selected from the group consisting of SEQ ID NO: 9, SEQ ID NO: 44, or SEQ ID NO: 31.

18. The method of claim 1, wherein the oligonucleotide comprises a sequence selected from CACAUGGAAGGCUGAGUCAGU (SEQ ID NO: 19); GCUUAGCAAGCACAUGGAAGG (SEQ ID NO: 13); and AGUAUGGGCUGGCUUAGCAAG (SEQ ID NO: 20).

* * * * *